US010537312B2

(12) United States Patent
Voss

(10) Patent No.: US 10,537,312 B2
(45) Date of Patent: Jan. 21, 2020

(54) ARTICULATING SUTURING DEVICE

(71) Applicant: Abbott Cardiovascular Systems, Inc., Santa Clara, CA (US)

(72) Inventor: Laveille Kao Voss, Belmont, CA (US)

(73) Assignee: Abbott Cardiovascular Systems, Inc., Santa Clara, CA (US)

(*) Notice: Subject to any disclaimer, the term of this patent is extended or adjusted under 35 U.S.C. 154(b) by 273 days.

(21) Appl. No.: 15/142,106

(22) Filed: Apr. 29, 2016

(65) Prior Publication Data

US 2016/0242749 A1    Aug. 25, 2016

Related U.S. Application Data

(63) Continuation of application No. 13/725,589, filed on Dec. 21, 2012, now Pat. No. 9,364,209.

(51) Int. Cl.
*A61B 17/04* (2006.01)
*A61B 17/00* (2006.01)
*A61B 17/06* (2006.01)

(52) U.S. Cl.
CPC .......... *A61B 17/0057* (2013.01); *A61B 17/04* (2013.01); *A61B 17/0469* (2013.01);
(Continued)

(58) Field of Classification Search
CPC . A61B 17/0057; A61B 17/04; A61B 17/0469; A61B 17/0482; A61B 17/0485;
(Continued)

(56) References Cited

U.S. PATENT DOCUMENTS 287,046 A    10/1883 Norton
438,400 A    10/1890 Brennan
(Continued)

FOREIGN PATENT DOCUMENTS

AU    2003297432    7/2004
CA    2 339 060    2/2000
(Continued)

OTHER PUBLICATIONS https://www.thefreedictionary.com/integral, retrieved Aug. 20, 2018, definition of the term integral.*
(Continued)

*Primary Examiner* — David C Eastwood
(74) *Attorney, Agent, or Firm* — Workman Nydegger; Randy Shen

(57) ABSTRACT

An apparatus for closing an opening in a body tissue. The apparatus includes a shaft, a plurality of arms, and an expander. The arms each extend between a proximal end and a distal end. The distal end of each arm is hingedly attached to or integrally formed with the shaft. The arms are laterally spaced apart from each other. The arms are movable between a retracted configuration, in which the arms are each aligned along the shaft, and a deployed configuration, in which the proximal end of each arm pivots respectively about the distal end of the arm so as to extend laterally away from the shaft. The expander is positioned within the shaft, and movement of the expander causes the arms to move between the retracted and deployed configurations. Methods of using the apparatus are also included.

14 Claims, 57 Drawing Sheets

(52) U.S. Cl.
CPC ...... *A61B 17/0482* (2013.01); *A61B 17/0485* (2013.01); *A61B 2017/00623* (2013.01); *A61B 2017/00663* (2013.01); *A61B 2017/00809* (2013.01); *A61B 2017/00818* (2013.01); *A61B 2017/0472* (2013.01); *A61B 2017/0477* (2013.01); *A61B 2017/0496* (2013.01); *A61B 2017/06042* (2013.01); *A61B 2017/06052* (2013.01)

(58) Field of Classification Search
CPC .......... A61B 17/0491; A61B 2017/047; A61B 2017/0472; A61B 2017/0477; A61B 2017/0496; A61B 2017/06042; A61B 2017/06052; A61B 2017/0623; A61B 2017/00663; D05B 1/00
See application file for complete search history.

(56) References Cited

U.S. PATENT DOCUMENTS

| | | | |
|---|---|---|---|
| 556,082 | A | 3/1896 | Boeddinghaus |
| 1,088,393 | A | 2/1914 | Backus |
| 1,123,290 | A | 1/1915 | Von Herff |
| 1,331,401 | A | 2/1920 | Summers |
| 1,596,004 | A | 8/1926 | De Bengoa |
| 1,647,958 | A | 11/1927 | Ciarlante |
| 1,880,569 | A | 10/1932 | Weis |
| 2,087,074 | A | 7/1937 | Tucker |
| 2,210,061 | A | 8/1940 | Caminez |
| 2,254,620 | A | 9/1941 | Miller |
| 2,316,297 | A | 4/1943 | Southerland et al. |
| 2,371,978 | A | 3/1945 | Perham |
| 2,453,227 | A | 11/1948 | James |
| 2,583,625 | A | 1/1952 | Bergan |
| 2,684,070 | A | 7/1954 | Kelsey |
| 2,755,699 | A | 7/1956 | Forster |
| 2,910,067 | A | 10/1959 | White |
| 2,944,311 | A | 7/1960 | Schneckenberger |
| 2,951,482 | A | 9/1960 | Sullivan |
| 2,969,887 | A | 1/1961 | Darmstadt et al. |
| 3,015,403 | A | 1/1962 | Fuller |
| 3,113,379 | A | 12/1963 | Frank |
| 3,120,230 | A | 2/1964 | Skold |
| 3,142,878 | A | 8/1964 | Santora |
| 3,209,754 | A | 10/1965 | Brown |
| 3,482,428 | A | 12/1969 | Kapitanov et al. |
| 3,494,533 | A | 2/1970 | Green et al. |
| 3,510,923 | A | 5/1970 | Blake |
| 3,517,128 | A | 6/1970 | Hines |
| 3,523,351 | A | 8/1970 | Filia |
| 3,557,794 | A | 1/1971 | Van Patten |
| 3,586,002 | A | 6/1971 | Wood et al. |
| 3,604,425 | A | 9/1971 | Le Roy |
| 3,618,447 | A | 11/1971 | Goins |
| 3,677,243 | A | 7/1972 | Nerz |
| 3,757,629 | A | 9/1973 | Schneider |
| 3,805,337 | A | 4/1974 | Branstetter |
| 3,823,719 | A | 7/1974 | Cummings |
| 3,828,791 | A | 8/1974 | Santos |
| 3,856,016 | A | 12/1974 | Davis |
| 3,874,388 | A | 4/1975 | King et al. |
| 3,908,662 | A | 9/1975 | Razgulov et al. |
| 3,926,194 | A | 12/1975 | Greenberg et al. |
| 3,939,820 | A | 2/1976 | Grayzel |
| 3,944,114 | A | 3/1976 | Coppens |
| 3,960,147 | A | 6/1976 | Murray |
| 3,985,138 | A | 10/1976 | Jarvik |
| 4,007,743 | A | 2/1977 | Blake |
| 4,014,492 | A | 3/1977 | Rothfuss |
| 4,018,228 | A | 4/1977 | Goosen |
| 4,047,533 | A | 9/1977 | Perciaccante et al. |
| 4,064,881 | A | 12/1977 | Meredith |
| 4,112,944 | A | 9/1978 | Williams |
| 4,153,321 | A | 5/1979 | Pombrol |
| 4,162,673 | A | 7/1979 | Patel |
| 4,169,476 | A | 10/1979 | Hiltebrandt |
| 4,192,315 | A | 3/1980 | Hilzinger et al. |
| 4,201,215 | A | 5/1980 | Crossett et al. |
| 4,204,541 | A | 5/1980 | Kapitanov |
| 4,207,870 | A | 6/1980 | Eldridge |
| 4,214,587 | A | 7/1980 | Sakura, Jr. |
| 4,215,699 | A | 8/1980 | Patel |
| 4,217,902 | A | 8/1980 | March |
| 4,273,129 | A | 6/1981 | Boebel |
| 4,274,415 | A | 6/1981 | Kanamoto et al. |
| 4,278,091 | A | 7/1981 | Borzone |
| 4,317,445 | A | 3/1982 | Robinson |
| 4,317,451 | A | 3/1982 | Cerwin et al. |
| 4,318,401 | A | 3/1982 | Zimmerman |
| 4,327,485 | A | 5/1982 | Rix |
| 4,345,606 | A | 8/1982 | Littleford |
| 4,368,736 | A | 1/1983 | Kaster |
| 4,396,139 | A | 8/1983 | Hall et al. |
| 4,407,286 | A | 10/1983 | Noiles et al. |
| 4,411,654 | A | 10/1983 | Boarini et al. |
| 4,412,832 | A | 11/1983 | Kling et al. |
| 4,428,376 | A | 1/1984 | Mericle |
| 4,440,170 | A | 4/1984 | Golden et al. |
| 4,449,531 | A | 5/1984 | Cerwin et al. |
| 4,475,544 | A | 10/1984 | Reis |
| 4,480,356 | A | 11/1984 | Martin |
| 4,485,816 | A | 12/1984 | Krumme |
| RE31,855 | E | 3/1985 | Osborne |
| 4,505,273 | A | 3/1985 | Braun et al. |
| 4,505,274 | A | 3/1985 | Speelman |
| 4,523,591 | A | 6/1985 | Kaplan et al. |
| 4,523,695 | A | 6/1985 | Braun et al. |
| 4,525,157 | A | 6/1985 | Valaincourt |
| 4,526,174 | A | 7/1985 | Froehlich |
| 4,570,633 | A | 2/1986 | Golden |
| 4,586,503 | A | 5/1986 | Kirsch et al. |
| 4,592,498 | A | 6/1986 | Braun et al. |
| 4,596,559 | A | 6/1986 | Fleischhacker |
| 4,607,638 | A | 8/1986 | Crainich |
| 4,610,251 | A | 9/1986 | Kumar |
| 4,610,252 | A | 9/1986 | Catalano |
| 4,635,634 | A | 1/1987 | Santos |
| 4,635,637 | A | 1/1987 | Schreiber |
| 4,644,956 | A | 2/1987 | Morgenstern |
| 4,651,737 | A | 3/1987 | Deniega |
| 4,664,305 | A | 5/1987 | Blake, III et al. |
| 4,665,906 | A | 5/1987 | Jervis |
| 4,687,469 | A | 8/1987 | Osypka |
| 4,693,249 | A | 9/1987 | Schenck et al. |
| 4,719,917 | A | 1/1988 | Barrows et al. |
| 4,724,840 | A | 2/1988 | McVay et al. |
| 4,738,658 | A | 4/1988 | Magro et al. |
| 4,744,364 | A | 5/1988 | Kensey |
| 4,747,407 | A | 5/1988 | Liu et al. |
| 4,759,364 | A | 7/1988 | Boebel |
| 4,771,782 | A | 9/1988 | Millar |
| 4,772,266 | A | 9/1988 | Groshong |
| 4,777,950 | A | 10/1988 | Kees, Jr. |
| 4,789,090 | A | 12/1988 | Blake, III |
| 4,832,688 | A | 5/1989 | Sagae et al. |
| 4,836,204 | A | 6/1989 | Landymore et al. |
| 4,852,568 | A | 8/1989 | Kensey |
| 4,860,746 | A | 8/1989 | Yoon |
| 4,865,026 | A | 9/1989 | Barrett |
| 4,874,122 | A | 10/1989 | Froelich et al. |
| 4,878,915 | A | 11/1989 | Brantigan |
| 4,885,003 | A | 12/1989 | Hillstead |
| 4,886,067 | A | 12/1989 | Palermo |
| 4,887,601 | A | 12/1989 | Richards |
| 4,890,612 | A | 1/1990 | Kensey |
| 4,902,508 | A | 2/1990 | Badylak et al. |
| 4,917,087 | A | 4/1990 | Walsh et al. |
| 4,917,089 | A | 4/1990 | Sideris |
| 4,929,240 | A | 5/1990 | Kirsch et al. |
| 4,934,364 | A | 6/1990 | Green |
| 4,950,258 | A | 8/1990 | Kawai et al. |
| 4,957,499 | A | 9/1990 | Lipatov et al. |
| 4,961,729 | A | 10/1990 | Vaillancourt |

(56) References Cited

U.S. PATENT DOCUMENTS

| | | |
|---|---|---|
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,011,487 A | 4/1991 | Shichman |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,041,129 A | 8/1991 | Hayhurst et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,061,283 A | 10/1991 | Silvestrini |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,259 A | 12/1992 | Inoue |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,610 A | 1/1994 | Eberbach |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,284,488 A | 2/1994 | Sideris |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,322,694 A | 6/1994 | Sixsmith |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Often |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,391,174 A | 2/1995 | Weston |
| 5,392,978 A | 2/1995 | Valez et al. |
| 5,395,030 A | 3/1995 | Kuramoto et al. |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,464,416 A | 11/1995 | Steckel |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,484,420 A | 1/1996 | Russo |
| 5,486,195 A | 1/1996 | Myers et al. |
| 5,496,332 A | 3/1996 | Sierra et al. |
| 5,497,933 A | 3/1996 | DeFonzo et al. |
| 5,507,744 A | 4/1996 | Tay et al. |
| 5,507,755 A | 4/1996 | Gresl et al. |
| 5,510,115 A | 4/1996 | Breillatt, Jr. et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,545,178 A | 8/1996 | Kensey et al. |

(56) References Cited

U.S. PATENT DOCUMENTS

| | | | |
|---|---|---|---|
| 5,547,474 | A | 8/1996 | Kloeckl et al. |
| 5,560,532 | A | 10/1996 | DeFonzo et al. |
| 5,571,120 | A | 11/1996 | Yoon |
| 5,573,784 | A | 11/1996 | Badylak et al. |
| 5,575,771 | A | 11/1996 | Walinsky |
| 5,582,616 | A | 12/1996 | Bolduc et al. |
| 5,584,879 | A | 12/1996 | Reimold et al. |
| 5,591,205 | A | 1/1997 | Fowler |
| 5,593,412 | A | 1/1997 | Martinez et al. |
| 5,601,602 | A | 2/1997 | Fowler |
| 5,609,597 | A | 3/1997 | Lehrer |
| 5,613,974 | A | 3/1997 | Andreas et al. |
| 5,618,291 | A | 4/1997 | Thompson et al. |
| 5,620,452 | A | 4/1997 | Yoon |
| 5,620,461 | A | 4/1997 | Muijs et al. |
| 5,626,614 | A | 5/1997 | Hart |
| 5,634,936 | A | 6/1997 | Linden et al. |
| 5,643,318 | A | 7/1997 | Tsukernik et al. |
| 5,645,565 | A | 7/1997 | Rudd et al. |
| 5,645,566 | A | 7/1997 | Brenneman et al. |
| 5,645,567 | A | 7/1997 | Crainich |
| 5,649,959 | A | 7/1997 | Hannam et al. |
| D383,539 | S | 9/1997 | Croley |
| 5,674,231 | A | 10/1997 | Green et al. |
| 5,674,244 | A | 10/1997 | Mathys |
| 5,676,689 | A | 10/1997 | Kensey et al. |
| 5,676,974 | A | 10/1997 | Valdes et al. |
| 5,681,280 | A | 10/1997 | Rusk et al. |
| 5,681,334 | A | 10/1997 | Evans et al. |
| 5,683,405 | A | 11/1997 | Yacoubian et al. |
| 5,690,674 | A | 11/1997 | Diaz |
| 5,695,504 | A | 12/1997 | Gifford, III et al. |
| 5,695,505 | A | 12/1997 | Yoon |
| 5,695,524 | A | 12/1997 | Kelley et al. |
| 5,697,943 | A | 12/1997 | Sauer et al. |
| 5,700,273 | A | 12/1997 | Buelna et al. |
| 5,709,224 | A | 1/1998 | Behl et al. |
| 5,715,987 | A | 2/1998 | Kelley et al. |
| 5,716,375 | A | 2/1998 | Fowler |
| 5,720,755 | A | 2/1998 | Dakov |
| 5,725,498 | A | 3/1998 | Janzen et al. |
| 5,725,552 | A | 3/1998 | Kotula et al. |
| 5,725,554 | A | 3/1998 | Simon et al. |
| 5,728,110 | A | 3/1998 | Vidal et al. |
| 5,728,114 | A | 3/1998 | Evans et al. |
| 5,728,116 | A | 3/1998 | Rosenman |
| 5,728,122 | A | 3/1998 | Leschinsky et al. |
| 5,728,132 | A | 3/1998 | Van Tassel et al. |
| 5,728,133 | A | 3/1998 | Kontos |
| 5,732,872 | A | 3/1998 | Bolduc et al. |
| 5,735,873 | A | 4/1998 | MacLean |
| 5,746,753 | A | 5/1998 | Sullivan et al. |
| 5,749,826 | A | 5/1998 | Faulkner |
| 5,752,966 | A | 5/1998 | Chang |
| 5,755,726 | A | 5/1998 | Pratt et al. |
| 5,755,727 | A | 5/1998 | Kontos |
| 5,755,778 | A | 5/1998 | Kleshinski |
| 5,766,217 | A | 6/1998 | Christy |
| 5,766,246 | A | 6/1998 | Mulhauser et al. |
| 5,769,870 | A | 6/1998 | Salahieh et al. |
| 5,776,147 | A | 7/1998 | Dolendo |
| 5,779,707 | A | 7/1998 | Bertholet et al. |
| 5,780,807 | A | 7/1998 | Saunders |
| 5,782,844 | A | 7/1998 | Yoon et al. |
| 5,782,860 | A | 7/1998 | Epstein et al. |
| 5,782,861 | A | 7/1998 | Cragg et al. |
| 5,795,958 | A | 8/1998 | Rao et al. |
| 5,797,928 | A | 8/1998 | Kogasaka |
| 5,797,931 | A | 8/1998 | Bito et al. |
| 5,797,933 | A | 8/1998 | Snow et al. |
| 5,797,958 | A | 8/1998 | Yoon |
| 5,797,960 | A | 8/1998 | Stevens et al. |
| 5,810,776 | A | 9/1998 | Bacich et al. |
| 5,810,846 | A | 9/1998 | Virnich et al. |
| 5,810,851 | A | 9/1998 | Yoon |
| 5,817,113 | A | 10/1998 | Gifford, III et al. |
| 5,820,631 | A | 10/1998 | Nobles |
| 5,827,298 | A | 10/1998 | Hart et al. |
| 5,830,125 | A | 11/1998 | Scribner et al. |
| 5,830,217 | A | 11/1998 | Ryan |
| 5,830,221 | A | 11/1998 | Stein et al. |
| 5,833,698 | A | 11/1998 | Hinchliffe et al. |
| 5,843,164 | A | 12/1998 | Frantzen et al. |
| 5,843,167 | A | 12/1998 | Dwyer et al. |
| 5,853,421 | A | 12/1998 | Leschinsky et al. |
| 5,853,422 | A | 12/1998 | Huebsch et al. |
| 5,855,312 | A | 1/1999 | Toledano |
| 5,858,082 | A | 1/1999 | Cruz et al. |
| 5,860,991 | A | 1/1999 | Klein et al. |
| 5,861,003 | A | 1/1999 | Latson et al. |
| 5,861,005 | A | 1/1999 | Kontos |
| 5,865,791 | A | 2/1999 | Whayne et al. |
| 5,868,755 | A | 2/1999 | Kanner et al. |
| 5,868,762 | A | 2/1999 | Cragg et al. |
| 5,868,763 | A | 2/1999 | Spence et al. |
| 5,871,474 | A | 2/1999 | Hermann et al. |
| 5,871,501 | A | 2/1999 | Leschinsky et al. |
| 5,871,525 | A | 2/1999 | Edwards et al. |
| 5,873,876 | A | 2/1999 | Christy |
| 5,873,891 | A | 2/1999 | Sohn |
| 5,879,366 | A | 3/1999 | Shaw et al. |
| 5,891,088 | A | 4/1999 | Thompson et al. |
| 5,897,487 | A | 4/1999 | Ouchi |
| 5,902,310 | A | 5/1999 | Foerster et al. |
| 5,904,696 | A | 5/1999 | Rosenman |
| 5,904,697 | A | 5/1999 | Gifford, III et al. |
| 5,904,703 | A | 5/1999 | Gilson |
| 5,906,631 | A | 5/1999 | Imran |
| 5,907,893 | A | 6/1999 | Zadno-Azizi et al. |
| 5,908,149 | A | 6/1999 | Welch et al. |
| 5,910,155 | A | 6/1999 | Ratcliff et al. |
| 5,919,207 | A | 7/1999 | Taheri |
| 5,922,009 | A | 7/1999 | Epstein et al. |
| 5,928,208 | A | 7/1999 | Chu et al. |
| 5,928,231 | A | 7/1999 | Klein et al. |
| 5,928,251 | A | 7/1999 | Aranyi et al. |
| 5,928,260 | A | 7/1999 | Chin et al. |
| 5,935,147 | A | 8/1999 | Kensey et al. |
| 5,938,667 | A | 8/1999 | Peyser et al. |
| 5,941,890 | A | 8/1999 | Voegele et al. |
| 5,947,999 | A | 9/1999 | Groiso |
| 5,948,001 | A | 9/1999 | Larsen |
| 5,951,518 | A | 9/1999 | Licata et al. |
| 5,951,575 | A | 9/1999 | Bolduc et al. |
| 5,951,576 | A | 9/1999 | Wakabayashi |
| 5,951,589 | A | 9/1999 | Epstein et al. |
| 5,954,732 | A | 9/1999 | Hart et al. |
| 5,957,900 | A | 9/1999 | Ouchi |
| 5,957,936 | A | 9/1999 | Yoon et al. |
| 5,957,938 | A | 9/1999 | Zhu et al. |
| 5,957,940 | A | 9/1999 | Tanner et al. |
| 5,964,782 | A | 10/1999 | Lafontaine et al. |
| 5,972,023 | A | 10/1999 | Tanner et al. |
| 5,976,161 | A | 11/1999 | Kirsch et al. |
| 5,976,174 | A | 11/1999 | Ruiz |
| 5,984,934 | A | 11/1999 | Ashby et al. |
| 5,984,948 | A | 11/1999 | Hasson |
| 5,984,949 | A | 11/1999 | Levin |
| 5,993,468 | A | 11/1999 | Rygaard |
| 5,993,476 | A | 11/1999 | Groiso |
| 6,001,110 | A | 12/1999 | Adams |
| 6,004,341 | A | 12/1999 | Zhu et al. |
| 6,007,563 | A | 12/1999 | Nash et al. |
| 6,007,574 | A | 12/1999 | Pulnev et al. |
| 6,010,517 | A | 1/2000 | Baccaro |
| 6,013,084 | A | 1/2000 | Ken et al. |
| 6,015,815 | A | 1/2000 | Mollison |
| 6,019,779 | A | 2/2000 | Thorud et al. |
| 6,022,372 | A | 2/2000 | Kontos |
| 6,024,750 | A | 2/2000 | Mastri |
| 6,024,756 | A | 2/2000 | Huebsch et al. |
| 6,030,364 | A | 2/2000 | Durgin et al. |
| 6,030,413 | A | 2/2000 | Lazarus |
| 6,033,427 | A | 3/2000 | Lee |

(56) References Cited

U.S. PATENT DOCUMENTS

| | | |
|---|---|---|
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,688 A | 5/2000 | Benderev et al. |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,074,395 A | 6/2000 | Trott et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,102,271 A | 8/2000 | Longo et al. |
| 6,105,217 A | 8/2000 | Caradine et al. |
| 6,110,184 A | 8/2000 | Weadock |
| 6,113,610 A | 9/2000 | Poncet |
| 6,113,611 A | 9/2000 | Allen et al. |
| 6,113,612 A | 9/2000 | Swanson et al. |
| 6,117,125 A | 9/2000 | Rothbarth et al. |
| 6,117,144 A | 9/2000 | Nobles et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,183,775 B1 | 2/2001 | Ventouras |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,210,418 B1 | 4/2001 | Storz et al. |
| 6,217,554 B1 | 4/2001 | Green |
| 6,220,248 B1 | 4/2001 | Voegele et al. |
| 6,221,102 B1 | 4/2001 | Baker et al. |
| 6,231,561 B1 | 5/2001 | Frazier et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,287,335 B1 | 9/2001 | Drasler et al. |
| 6,290,674 B1 | 9/2001 | Roue et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,355,061 B1 | 3/2002 | Quiachon et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,485,504 B1 | 11/2002 | Johnson et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,544,230 B1 | 4/2003 | Flaherty et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,596,013 B2 | 7/2003 | Yang et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,626,930 B1 | 9/2003 | Allen et al. |
| 6,632,197 B2 | 10/2003 | Lyon |
| 6,632,238 B1 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |

(56) References Cited

U.S. PATENT DOCUMENTS

| | | |
|---|---|---|
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,671 B2 | 1/2004 | Robertson et al. |
| 6,676,685 B2 | 1/2004 | Pedros et al. |
| 6,679,894 B2 | 1/2004 | Damarati |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,784 B2 | 8/2004 | Ginn |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,087,088 B2 | 8/2006 | Berg et al. |
| 7,094,245 B2 | 8/2006 | Adams et al. |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,175,646 B2 | 2/2007 | Brenneman et al. |
| 7,211,101 B2 | 5/2007 | Carley et al. |
| 7,220,268 B2 | 5/2007 | Blatter |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,729 B2 | 10/2008 | Chanduszko |
| 7,445,596 B2 | 11/2008 | Kucklick et al. |
| 7,452,327 B2 | 11/2008 | Durgin et al. |
| 7,465,286 B2 | 12/2008 | Patterson et al. |
| 7,533,790 B1 | 5/2009 | Knodel et al. |
| 7,556,632 B2 | 7/2009 | Zadno |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| D611,144 S | 3/2010 | Reynolds |
| 7,678,135 B2 | 3/2010 | Maahs et al. |
| 7,780,696 B2 | 8/2010 | Daniel et al. |
| 7,806,904 B2 | 10/2010 | Carley et al. |
| 7,819,895 B2 | 10/2010 | Ginn et al. |
| 7,824,419 B2 | 11/2010 | Boraiah |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,875,054 B2 | 1/2011 | LaFontaine |
| 7,879,071 B2 | 2/2011 | Carley et al. |
| 7,887,555 B2 | 2/2011 | Carley et al. |
| 7,887,563 B2 | 2/2011 | Cummins et al. |
| 7,901,428 B2 | 3/2011 | Ginn et al. |
| 7,905,900 B2 | 3/2011 | Palermo |
| 7,918,873 B2 | 4/2011 | Cummins et al. |
| 7,931,669 B2 | 4/2011 | Ginn et al. |
| 7,931,671 B2 | 4/2011 | Tenerz |
| 7,967,842 B2 | 6/2011 | Bakos |
| 8,007,512 B2 | 8/2011 | Ginn et al. |
| 8,038,688 B2 | 10/2011 | Modesitt et al. |
| 8,083,768 B2 | 12/2011 | Ginn et al. |
| 8,103,327 B2 | 1/2012 | Harlev et al. |
| 8,105,352 B2 | 1/2012 | Egnelöv |
| 8,128,644 B2 | 3/2012 | Carley et al. |
| 8,172,749 B2 | 5/2012 | Melsheimer |
| 8,182,497 B2 | 5/2012 | Carley et al. |
| 8,192,459 B2 | 6/2012 | Cummins et al. |
| 8,202,283 B2 | 6/2012 | Carley et al. |
| 8,202,293 B2 | 6/2012 | Ellingwood et al. |
| 8,202,294 B2 | 6/2012 | Jabba et al. |
| 8,211,122 B2 | 7/2012 | McIntosh |
| 8,216,260 B2 | 7/2012 | Lam et al. |
| 8,226,681 B2 | 7/2012 | Clark et al. |
| 8,236,026 B2 | 8/2012 | Carley et al. |
| 8,257,390 B2 | 9/2012 | Carley et al. |
| 8,303,624 B2 | 11/2012 | Fortson |
| 8,313,497 B2 | 11/2012 | Walberg et al. |
| 8,323,312 B2 | 12/2012 | Clark |
| 8,398,656 B2 | 3/2013 | Palermo et al. |
| 8,398,676 B2 | 3/2013 | Roorda et al. |
| 8,403,929 B2 | 3/2013 | Weisshaupt et al. |
| 8,409,228 B2 | 4/2013 | Blatter et al. |
| 8,469,995 B2 | 6/2013 | Cummins et al. |
| 8,486,092 B2 | 7/2013 | Carley et al. |
| 8,486,108 B2 | 7/2013 | Carley et al. |
| 8,491,609 B2 * | 7/2013 | Stone ............... A61B 17/0469 606/144 |

(56) References Cited

U.S. PATENT DOCUMENTS

| | | |
|---|---|---|
| 8,518,057 B2 | 8/2013 | Walberg et al. |
| 8,529,587 B2 | 9/2013 | Ellingwood et al. |
| 8,556,930 B2 | 10/2013 | Ellingwood |
| 8,562,630 B2 | 10/2013 | Campbell |
| 8,574,244 B2 | 11/2013 | Reynolds |
| 8,579,932 B2 | 11/2013 | Pantages |
| 8,579,933 B2 | 11/2013 | Chin-Chen et al. |
| 8,585,836 B2 | 11/2013 | Carley et al. |
| 8,590,760 B2 | 11/2013 | Cummins et al. |
| 8,597,325 B2 | 12/2013 | Ginn |
| 8,603,116 B2 | 12/2013 | Roorda |
| 8,603,136 B2 | 12/2013 | Ginn |
| 8,657,852 B2 | 2/2014 | Roorda et al. |
| 8,672,953 B2 | 3/2014 | Reyes et al. |
| 8,690,910 B2 | 4/2014 | Carley et al. |
| 8,728,119 B2 | 5/2014 | Cummins |
| 8,758,396 B2 | 6/2014 | Ginn et al. |
| 8,758,398 B2 | 6/2014 | Carley |
| 8,758,399 B2 | 6/2014 | Fortson et al. |
| 8,758,400 B2 | 6/2014 | Ginn et al. |
| 8,784,447 B2 | 7/2014 | Coleman et al. |
| 8,808,310 B2 | 8/2014 | Jones et al. |
| 8,820,602 B2 | 9/2014 | Walberg et al. |
| 8,821,534 B2 | 9/2014 | Voss |
| 8,834,494 B2 | 9/2014 | Schorr et al. |
| 8,858,594 B2 | 10/2014 | Clark |
| 8,893,947 B2 | 11/2014 | Reynolds et al. |
| 8,905,937 B2 | 12/2014 | Ellingwood et al. |
| 8,926,633 B2 | 1/2015 | Carly |
| 8,926,656 B2 | 1/2015 | Palermo et al. |
| 8,956,388 B2 | 2/2015 | Ginn et al. |
| 8,992,549 B2 | 3/2015 | Bennett, III |
| 9,050,068 B2 | 6/2015 | Walberg et al. |
| 9,050,087 B2 | 6/2015 | Ginn et al. |
| 9,060,769 B2 | 6/2015 | Coleman et al. |
| 9,089,311 B2 | 7/2015 | Fortson et al. |
| 9,089,674 B2 | 7/2015 | Ginn et al. |
| 9,149,276 B2 | 10/2015 | Voss |
| 9,173,644 B2 | 11/2015 | Voss |
| 9,241,696 B2 | 1/2016 | Mehl |
| 9,271,707 B2 | 3/2016 | Palermo et al. |
| 9,282,965 B2 | 3/2016 | Kokish |
| 9,295,469 B2 | 3/2016 | Cummins et al. |
| 9,314,230 B2 | 4/2016 | Roorda et al. |
| 9,320,522 B2 | 4/2016 | Carley et al. |
| 9,332,976 B2 | 5/2016 | Yribarren |
| 9,345,460 B2 | 5/2016 | Houser et al. |
| 9,364,209 B2 | 6/2016 | Voss |
| 2001/0007077 A1 | 7/2001 | Ginn et al. |
| 2001/0021855 A1 | 9/2001 | Levinson |
| 2001/0031972 A1 | 10/2001 | Robertson et al. |
| 2001/0031973 A1* | 10/2001 | Nobles ............... A61B 17/0057 606/144 |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0045908 A1* | 4/2002 | Nobles ............... A61B 17/0057 606/144 |
| 2002/0049427 A1 | 4/2002 | Wiener et al. |
| 2002/0049453 A1 | 4/2002 | Nobles et al. |
| 2002/0056460 A1 | 5/2002 | Boyd et al. |
| 2002/0058960 A1 | 5/2002 | Hudson et al. |
| 2002/0062104 A1 | 5/2002 | Ashby et al. |
| 2002/0077657 A1 | 6/2002 | Ginn et al. |
| 2002/0082641 A1 | 6/2002 | Ginn et al. |
| 2002/0095164 A1 | 7/2002 | Andreas et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0151921 A1 | 10/2002 | Kanner et al. |
| 2002/0151963 A1 | 10/2002 | Brown et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0198562 A1 | 12/2002 | Ackerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0083679 A1 | 5/2003 | Grudem et al. |
| 2003/0088269 A1 | 5/2003 | Ashby |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158578 A1 | 8/2003 | Pantages et al. |
| 2003/0167063 A1 | 9/2003 | Kerr |
| 2003/0195504 A1 | 10/2003 | Tallarida et al. |
| 2003/0208211 A1 | 11/2003 | Kortenbach |
| 2004/0002763 A1 | 1/2004 | Phillips et al. |
| 2004/0009205 A1 | 1/2004 | Sawhney |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0147957 A1 | 7/2004 | Pierson, III |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravikumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149066 A1 | 7/2005 | Stafford |
| 2005/0149117 A1 | 7/2005 | Khosravi et al. |

(56) References Cited

U.S. PATENT DOCUMENTS

| | | |
|---|---|---|
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0222614 A1 | 10/2005 | Ginn et al. |
| 2005/0228405 A1 | 10/2005 | Maruyama et al. |
| 2005/0228443 A1 | 10/2005 | Yassinzadeh |
| 2005/0245876 A1 | 11/2005 | Khosravi et al. |
| 2005/0256532 A1 | 11/2005 | Nayak et al. |
| 2005/0267495 A1 | 12/2005 | Ginn et al. |
| 2005/0267524 A1 | 12/2005 | Chanduszko |
| 2005/0273136 A1 | 12/2005 | Belef et al. |
| 2005/0273137 A1 | 12/2005 | Ginn |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0064115 A1 | 3/2006 | Allen et al. |
| 2006/0069397 A1 | 3/2006 | Nobles et al. |
| 2006/0100664 A1 | 5/2006 | Pai et al. |
| 2006/0142784 A1 | 6/2006 | Kontos |
| 2006/0162509 A1 | 7/2006 | Wang |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0195123 A1 | 8/2006 | Ginn et al. |
| 2006/0195125 A1 | 8/2006 | Sakakine et al. |
| 2006/0206146 A1 | 9/2006 | Tenerez |
| 2006/0217744 A1 | 9/2006 | Bender et al. |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0287673 A1 | 12/2006 | Brett et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010851 A1 | 1/2007 | Chanduszko et al. |
| 2007/0027476 A1 | 2/2007 | Harris et al. |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060858 A1 | 3/2007 | Sogard et al. |
| 2007/0060895 A1 | 3/2007 | Sibbitt, Jr. et al. |
| 2007/0060950 A1 | 3/2007 | Khosravi et al. |
| 2007/0073337 A1 | 3/2007 | Abbott et al. |
| 2007/0078302 A1 | 4/2007 | Ortiz et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0149996 A1 | 6/2007 | Coughlin |
| 2007/0167981 A1 | 7/2007 | Opolski et al. |
| 2007/0172430 A1 | 7/2007 | Brito et al. |
| 2007/0179527 A1 | 8/2007 | Eskuri et al. |
| 2007/0185529 A1 | 8/2007 | Coleman et al. |
| 2007/0185530 A1 | 8/2007 | Chin-Chen et al. |
| 2007/0203507 A1 | 8/2007 | McLaughlin et al. |
| 2007/0208376 A1 | 9/2007 | Meng |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0265658 A1 | 11/2007 | Nelson et al. |
| 2007/0275036 A1 | 11/2007 | Green, III et al. |
| 2007/0276488 A1 | 11/2007 | Wachter et al. |
| 2007/0282373 A1 | 12/2007 | Ashby et al. |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0082123 A1 | 4/2008 | Forsberg et al. |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0097509 A1 | 4/2008 | Beyar et al. |
| 2008/0114378 A1 | 5/2008 | Matsushita |
| 2008/0114395 A1 | 5/2008 | Mathisen et al. |
| 2008/0269802 A1 | 5/2008 | Coleman et al. |
| 2008/0177288 A1 | 7/2008 | Carlson |
| 2008/0208225 A1 | 8/2008 | Seibold et al. |
| 2008/0215089 A1 | 9/2008 | Williams et al. |
| 2008/0215090 A1 | 9/2008 | Gonzales et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0262541 A1 | 10/2008 | Sater et al. |
| 2008/0269801 A1 | 10/2008 | Coleman et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312667 A1 | 12/2008 | Drasler et al. |
| 2008/0312686 A1 | 12/2008 | Ellingwood |
| 2008/0312740 A1 | 12/2008 | Wachter et al. |
| 2009/0054912 A1 | 2/2009 | Heanue et al. |
| 2009/0062846 A1 | 3/2009 | Ken |
| 2009/0112306 A1 | 4/2009 | Bonsignore et al. |
| 2009/0132031 A1 | 5/2009 | Cook et al. |
| 2009/0137900 A1 | 5/2009 | Bonner et al. |
| 2009/0157101 A1 | 6/2009 | Reyes et al. |
| 2009/0171388 A1 | 7/2009 | Dave et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0259233 A1 | 10/2009 | Bogart et al. |
| 2009/0281555 A1 | 11/2009 | Stone |
| 2009/0312789 A1 | 12/2009 | Kassab et al. |
| 2010/0042118 A1 | 2/2010 | Garrison et al. |
| 2010/0042144 A1 | 2/2010 | Bennett |
| 2010/0114119 A1 | 5/2010 | McLawhorn et al. |
| 2010/0130965 A1 | 5/2010 | Sibbitt, Jr. et al. |
| 2010/0179567 A1* | 7/2010 | Voss .............. A61B 17/0057 606/139 |
| 2010/0179572 A1 | 7/2010 | Voss et al. |
| 2010/0179589 A1 | 7/2010 | Roorda et al. |
| 2010/0185216 A1 | 7/2010 | Garrison et al. |
| 2010/0185234 A1 | 7/2010 | Fortson et al. |
| 2010/0249828 A1 | 9/2010 | Mavani et al. |
| 2011/0054492 A1 | 3/2011 | Clark |
| 2011/0082495 A1 | 4/2011 | Ruiz |
| 2011/0137340 A1 | 6/2011 | Cummins |
| 2011/0178548 A1 | 7/2011 | Tenerz |
| 2011/0190793 A1 | 8/2011 | Nobles et al. |
| 2011/0218568 A1 | 9/2011 | Voss |
| 2011/0270282 A1* | 11/2011 | Lemke ............. A61B 17/0057 606/148 |
| 2011/0288563 A1 | 11/2011 | Gianotti et al. |
| 2012/0101520 A1 | 4/2012 | Ginn et al. |
| 2012/0245623 A1 | 9/2012 | Kariniemi et al. |
| 2013/0053792 A1 | 2/2013 | Fischell et al. |
| 2013/0178872 A1 | 7/2013 | Shriver |
| 2013/0310853 A1 | 11/2013 | Zaugg et al. |
| 2014/0005692 A1 | 1/2014 | Ellingwood et al. |
| 2014/0018850 A1 | 1/2014 | Ellingwood |
| 2014/0039549 A1 | 2/2014 | Belsky et al. |
| 2014/0081318 A1 | 3/2014 | Houser et al. |
| 2014/0142624 A1 | 5/2014 | Pantages et al. |
| 2014/0222068 A1 | 8/2014 | Carley et al. |
| 2014/0222069 A1 | 8/2014 | Carley et al. |
| 2014/0309686 A1 | 10/2014 | Ginn et al. |
| 2014/0364900 A1 | 12/2014 | Fortson et al. |
| 2015/0073471 A1 | 3/2015 | Clark |
| 2015/0080914 A1 | 3/2015 | Roundy et al. |

(56) References Cited

U.S. PATENT DOCUMENTS

| | | |
|---|---|---|
| 2015/0190071 A1 | 7/2015 | Ellingwood et al. |
| 2015/0265279 A1 | 9/2015 | Walberg et al. |
| 2016/0000417 A1 | 1/2016 | Voss et al. |
| 2016/0051258 A1 | 2/2016 | Cummins et al. |
| 2016/0120546 A1 | 5/2016 | Roundy et al. |
| 2016/0151057 A1 | 6/2016 | Voss |
| 2016/0174954 A1 | 6/2016 | Palermo et al. |
| 2016/0192913 A1 | 7/2016 | Kokish |
| 2017/0020496 A1 | 1/2017 | Yribarren |
| 2017/0020517 A1 | 1/2017 | Coleman et al. |
| 2017/0049426 A1 | 2/2017 | Gianotti et al. |
| 2017/0135680 A1 | 5/2017 | Pantages et al. |
| 2017/0135684 A1 | 5/2017 | Carley et al. |
| 2018/0256166 A1 | 9/2018 | Cummins et al. |
| 2018/0325506 A1 | 11/2018 | Ellingwood |
| 2019/0117205 A1 | 4/2019 | Kokish |
| 2019/0117207 A1 | 4/2019 | Carley et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/00046 | 1/1997 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/62234 | 8/2002 |
| WO | WO 02/98302 | 12/2002 |
| WO | WO 03/13363 | 2/2003 |
| WO | WO 03/13364 | 2/2003 |
| WO | WO 03/47434 | 6/2003 |
| WO | WO 03/71955 | 9/2003 |
| WO | WO 03/71956 | 9/2003 |
| WO | WO 03/71957 | 9/2003 |
| WO | WO 03/94748 | 11/2003 |
| WO | WO 03/101310 | 12/2003 |
| WO | WO 04/04578 | 1/2004 |
| WO | WO 04/12602 | 2/2004 |
| WO | WO 04/60169 | 7/2004 |
| WO | WO 04/69054 | 8/2004 |
| WO | WO 05/000126 | 1/2005 |
| WO | WO 05/006990 | 1/2005 |
| WO | WO 05/041782 | 5/2005 |
| WO | WO 05/063129 | 7/2005 |
| WO | WO 05/082256 | 9/2005 |
| WO | WO 05/092204 | 10/2005 |
| WO | WO 05/110240 | 11/2005 |
| WO | WO 05/112782 | 12/2005 |
| WO | WO 05/115251 | 12/2005 |
| WO | WO 05/115521 | 12/2005 |
| WO | WO 06/000514 | 1/2006 |
| WO | WO 06/026116 | 3/2006 |
| WO | WO 06/052611 | 5/2006 |
| WO | WO 06/052612 | 5/2006 |
| WO | WO 06/078578 | 7/2006 |
| WO | WO 06/083889 | 8/2006 |
| WO | WO 06/115901 | 11/2006 |
| WO | WO 06/115904 | 11/2006 |
| WO | WO 06/118877 | 11/2006 |
| WO | WO 07/05585 | 1/2007 |
| WO | WO 07/25014 | 3/2007 |
| WO | WO 07/81836 | 7/2007 |
| WO | WO 07/88069 | 8/2007 |
| WO | WO 08/031102 | 3/2008 |
| WO | WO 08/036384 | 3/2008 |
| WO | WO 08/074027 | 6/2008 |
| WO | WO 08/150915 | 12/2008 |
| WO | WO 09/079091 | 6/2009 |
| WO | WO 10/062693 | 6/2010 |
| WO | WO 10/081101 | 7/2010 |
| WO | WO 10/081102 | 7/2010 |
| WO | WO 10/081103 | 7/2010 |

(56) References Cited

FOREIGN PATENT DOCUMENTS

| WO | WO 10/081106 | 7/2010 |
|----|--------------|--------|
| ZA | 200100527    | 1/2001 |
| ZA | 200100528    | 1/2001 |

OTHER PUBLICATIONS https://www.thefreedictionary.com/flex, retrieved Sep. 2, 2018, definition of the term flex.*
U.S. Appl. No. 13/837,801, Feb. 9, 2017, Office Action.
U.S. Appl. No. 13/837,801, Jul. 6, 2017, Office Action.
U.S. Appl. No. 14/023,428, Dec. 20, 2016, Office Action.
U.S. Appl. No. 14/023,428, Jul. 18, 2017, Office Action.
U.S. Appl. No. 14/023,428, Jan. 4, 2018, Notice of Allowance.
U.S. Appl. No. 14/077,007, Aug. 12, 2016, Notice of Allowance.
U.S. Appl. No. 14/246,926, Oct. 3, 2016, Notice of Allowance.
U.S. Appl. No. 14/246,973, Nov. 9, 2016, Notice of Allowance.
U.S. Appl. No. 14/312,339, Jan. 31, 2017, Office Action.
U.S. Appl. No. 14/312,339, May 23, 2017, Office Action.
U.S. Appl. No. 14/312,339, Aug. 28, 2017, Office Action.
U.S. Appl. No. 14/312,339, Dec. 28, 2017, Office Action.
U.S. Appl. No. 14/539,830, Jul. 26, 2016, Office Action.
U.S. Appl. No. 14/539,830, Nov. 18, 2016, Notice of Allowance.
U.S. Appl. No. 14/732,977, Sep. 26, 2017, Office Action.
U.S. Appl. No. 14/839,658, May 30, 2017, Office Action.
U.S. Appl. No. 14/839,658, Sep. 19, 2017, Office Action.
U.S. Appl. No. 14/839,658, Feb. 28, 2018, Notice of Allowance.
U.S. Appl. No. 14/855,080, Apr. 2, 2018, Office Action.
U.S. Appl. No. 14/928,950, Sep. 26, 2017, Office Action.
U.S. Appl. No. 14/928,950, Mar. 30, 2018, Office Action.
U.S. Appl. No. 15/056,281, Feb. 5, 2018, Office Action.
U.S. Appl. No. 15/069,230, Feb. 15, 2018, Office Action.
U.S. Appl. No. 15/149,784, May 11, 2017, Office Action.
U.S. Appl. No. 15/222,397, Jan. 23, 2017, Office Action.
U.S. Appl. No. 15/356,028, Feb. 22, 2018, Office Action.
U.S. Appl. No. 14/732,977, May 29, 2018, Notice of Allowance.
U.S. Appl. No. 14/928,950, Jun. 4, 2018, Interview Summary.
U.S. Appl. No. 15/056,281, Jun. 13, 2018, Office Action.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 13/017,636, filed Jan. 31, 2011, Carley et al.
U.S. Appl. No. 15/005,780, filed Jan. 25, 2016, Mehl.
U.S. Appl. No. 15/131,786, filed Apr. 18, 2016, Roorda et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
"Hand tool for forming telephone connections—comprises pliers with reciprocably driven ram crimping clip around conductors against anvil", Derwent-ACC-No. 1978-B8090A. (Jan. 10, 1978).
Carpenter et al, Midterm results of the multicenter trial of the Powerlink bifurcated system for endovascular aortic aneurysm repair, Journal of Vascular Surgery, vol. 40, No. 5, Nov. 2004, p. 849-859.e5.
Database WPI; Section PQ, Week 200120; Derwent Publications Ltd., London GB; Class P31, AN 2001-203165; XP002199926 & ZA 200 100 528 A (Anthony T), Feb. 28, 2001 (Feb. 28, 2001) abstract.

Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
Eisenack et al, Percutaneous Endovascular Aortic Aneurysm Repair: A Prospective Evaluation of Safety, Efficiency, and Risk Factors, Journal of Endovascular Ther., 2009, vol. 16, p. 708-713.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
Greenhalgh et al, Endovascular versus open repair of abdominal aortic aneurysm, The New England journal of medicine, vol. 362, No. 20, 2010, p. 1863-1871.
Grossman, W., Cardiac Catheterization and Angiography, 3rd Ed., Lea & Febiger, Philadelphia, pp. 1-49, 52-247, 1986.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
Howell et al, Percutaneous Repair of Abdominal Aortic Aneurysms Using the aneuRx Stent Graft and the Percutaneous Vascular Surgery Device, Catheterization and cardiovascular interventions, vol. 55, No. 3, 2002, p. 281-287.
Inlet Medical Inc. Brochure, pp. 1-2, referencing OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
Jean-Baptiste et al., Percutaneous closure devices for endovascular repair of infrarenal abdominal aortic aneurysms: a prospective, non-randomized comparative study, European Journal of Vascular and Endovascular Surgery, vol. 35, No. 4, 2008, p. 422-428.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert Phd, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998 pp. 1648-1652, vol. 67, a Divison of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Krajcer and Gregoric, Totally percutaneous aortic aneurysm repair: methods and outcomes using the fully integrated IntuiTrak endovascular system, The Journal of cardiovascular surgery, vol. 51, No. 4, 2010, p. 493-501.
Lederle et al, Outcomes following endovascular vs open repair of abdominal aortic aneurysm: a randomized trial, Jama, vol. 302, No. 14, 2009, p. 1535-1542.
Lee et al, Total percutaneous access for endovascular aortic aneurysm repair ("Preclose" technique), Journal of vascular surgery, vol. 45, No. 6, 2007, p. 1095-1101.

(56) References Cited

OTHER PUBLICATIONS

Malkawi et al, Percutaneous access for endovascular aneurysm repair: a systematic review, European Journal of Vascular and Endovascular Surgery, vol. 39, No. 6, 2010, p. 676-682.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Morasch et al, Percutaneous repair of abdominal aortic aneurysm, Journal of vascular surgery, vol. 40, No. 1, 2004, p. 12-16.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
Rachel et al, Percutaneous endovascular abdominal aortic aneurysm repair, Annals of vascular surgery, vol. 16, No. 1, 2002, p. 43-49.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Starnes et al, Totally percutaneous aortic aneurysm repair: experience and prudence, Journal of vascular surgery, vol. 43, No. 2, 2006, p. 270-276.
Stretch Comb by Scunci, retrieved via internet at www.scunci.com/productdetail by examiner on Oct. 9, 2007, publication date unavailable.
Swee Lian Tan, MD, Phd, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Teh et al, Use of the percutaneous vascular surgery device for closure of femoral access sites during endovascular aneurysm repair: lessons from our experience, European Journal of Vascular and Endovascular Surgery, vol. 22, No. 5, 2001, p. 418-423.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.
Torsello et al, Endovascular suture versus cutdown for endovascular aneurysm repair: a prospective randomized pilot study, Journal of vascular surgery, vol. 38, No. 1, 2003, p. 78-82.
Traul et al, Percutaneous endovascular repair of infrarenal abdominal aortic aneurysms: a feasibility study, Journal of vascular surgery, vol. 32, No. 4, 2000, p. 770-776.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Watelet et al, Percutaneous repair of aortic aneurysms: a prospective study of suture-mediated closure devices, European journal of vascular and endovascular surgery, vol. 32, No. 3, 2006, p. 261-265.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.

(56) References Cited

OTHER PUBLICATIONS

U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner's Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/667,144, Jun. 6, 2011, Office Action.
U.S. Appl. No. 10/667,144, Oct. 28, 2011, Notice of Allowance.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/682,459, Apr. 1, 2011, Notice of Allowance.
U.S. Appl. No. 10/786,444, Oct. 30, 2006, Office Action.
U.S. Appl. No. 10/786,444, Apr. 17, 2007, Office Action.

(56) References Cited

OTHER PUBLICATIONS

U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/786,444, Jul. 11, 2013, Notice of Allowance.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 10/908,721, Jul. 18, 2013, Notice of Allowance.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/113,549, Mar. 14, 2014, Notice of Allowance.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/344,891, Jan. 22, 2013, Notice of Allowance.
U.S. Appl. No. 11/390,586, Jun. 24, 2009, Office Action.
U.S. Appl. No. 11/390,586, Jul. 6, 2010, Office Action.
U.S. Appl. No. 11/390,586, May 3, 2012, Notice of Allowance.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,141, Apr. 30, 2013, Office Action.
U.S. Appl. No. 11/396,141, Aug. 21, 2013, Office Action.
U.S. Appl. No. 11/396,141, Nov. 4, 2013, Notice of Allowance.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/396,731, Mar. 22, 2011, Office Action.
U.S. Appl. No. 11/396,731, Sep. 1, 2011, Office Action.
U.S. Appl. No. 11/396,731, Feb. 12, 2015, Office Action.
U.S. Appl. No. 11/396,731, Jul. 9, 2015, Notice of Allowance.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/411,925, Oct. 1, 2013, Office Action.
U.S. Appl. No. 11/411,925, Feb. 5, 2014, Notice of Allowance.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,297, Mar. 21, 2011, Office Action.
U.S. Appl. No. 11/427,297, Jun. 26, 2012, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/427,309, Jun. 7, 2013, Notice of Allowance.
U.S. Appl. No. 11/455,993, Feb. 17, 2009, Office Action.
U.S. Appl. No. 11/455,993, Dec. 16, 2009, Office Action.
U.S. Appl. No. 11/455,993, Jan. 29, 2014, Office Action.
U.S. Appl. No. 11/455,993, Aug. 11, 2014, Notice of Allowance.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,325, Jul. 17, 2013, Office Action.
U.S. Appl. No. 11/532,325, Dec. 2, 2013, Office Action.
U.S. Appl. No. 11/532,325, Jan. 16, 2015, Notice of Allowance.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/674,930, Apr. 3, 2014, Notice of Allowance.
U.S. Appl. No. 11/675,462, Dec. 10, 2009, Office Action.
U.S. Appl. No. 11/675,462, Aug. 31, 2010, Office Action.
U.S. Appl. No. 11/675,462, Aug. 3, 2011, Office Action.
U.S. Appl. No. 11/675,462, Dec. 22, 2011, Notice of Allowance.
U.S. Appl. No. 11/744,089, Nov. 26, 2008, Office Action.
U.S. Appl. No. 11/744,089, Aug. 14, 2009, Office Action.
U.S. Appl. No. 11/744,089, Aug. 8, 2012, Office Action.
U.S. Appl. No. 11/744,089, Apr. 15, 2013, Office Action.
U.S. Appl. No. 11/744,089, Aug. 8, 2013, Notice of Allowance.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/767,818, Feb. 16, 2011, Office Action.
U.S. Appl. No. 11/767,818, Feb. 3, 2012, Notice of Allowance.
U.S. Appl. No. 11/852,190, Jun. 24, 2010, Office Action.
U.S. Appl. No. 11/852,190, Nov. 1, 2010, Office Action.
U.S. Appl. No. 11/852,190, Mar. 2, 2011, Office Action.
U.S. Appl. No. 11/852,190, Apr. 24, 2013, Office Action.
U.S. Appl. No. 11/852,190, Nov. 26, 2013, Office Action.
U.S. Appl. No. 11/852,190, Feb. 12, 2014, Notice of Allowance.
U.S. Appl. No. 11/958,281, Sep. 2, 2010, Office Action.
U.S. Appl. No. 11/958,281, Oct. 8, 2010, Office Action.
U.S. Appl. No. 11/958,281, Mar. 10, 2011, Office Action.
U.S. Appl. No. 11/958,295, Aug. 27, 2009, Office Action.
U.S. Appl. No. 11/958,295, May 25, 2010, Office Action.
U.S. Appl. No. 11/958,295, Jun. 13, 2014, Notice of Allowance.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.

(56) References Cited

OTHER PUBLICATIONS

U.S. Appl. No. 12/106,928, Oct. 25, 2010, Office Action.
U.S. Appl. No. 12/106,928, Jun. 28, 2013, Office Action.
U.S. Appl. No. 12/106,928, Dec. 2, 2013, Office Action.
U.S. Appl. No. 12/106,928, Mar. 25, 2014, Advisory Action.
U.S. Appl. No. 12/106,928, Oct. 3, 2014, Notice of Allowance.
U.S. Appl. No. 12/106,937, Mar. 30, 2009, Office Action.
U.S. Appl. No. 12/106,937, Nov. 18, 2009, Office Action.
U.S. Appl. No. 12/106,937, Jun. 28, 2013, Office Action.
U.S. Appl. No. 12/106,937, Jan. 22, 2014, Office Action.
U.S. Appl. No. 12/106,937, Mar. 5, 2015, Notice of Allowance.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/113,851, Apr. 27, 2011, Office Action.
U.S. Appl. No. 12/113,851, Mar. 29, 2012, Office Action.
U.S. Appl. No. 12/113,851, Mar. 17, 2014, Office Action.
U.S. Appl. No. 12/113,851, Aug. 21, 2014, Office Action.
U.S. Appl. No. 12/113,851, Feb. 20, 2015, Notice of Allowance.
U.S. Appl. No. 12/114,031, Oct. 5, 2010, Office Action.
U.S. Appl. No. 12/114,031, Nov. 22, 2010, Office Action.
U.S. Appl. No. 12/114,031, May 11, 2011, Office Action.
U.S. Appl. No. 12/114,031, Aug. 2, 2011, Office Action.
U.S. Appl. No. 12/114,031, Mar. 6, 2012, Office Action.
U.S. Appl. No. 12/114,031, Mar. 10, 2014, Office Action.
U.S. Appl. No. 12/114,091, Oct. 27, 2010, Office Action.
U.S. Appl. No. 12/114,091, Dec. 17, 2010, Office Action.
U.S. Appl. No. 12/114,091, Jul. 7, 2011, Office Action.
U.S. Appl. No. 12/114,091, Apr. 5, 2012, Office Action.
U.S. Appl. No. 12/114,091, Nov. 8, 2012, Office Action.
U.S. Appl. No. 12/114,091, Feb. 12, 2015, Office Action.
U.S. Appl. No. 12/114,091, Jul. 23, 2015, Office Action.
U.S. Appl. No. 12/114,091, Apr. 6, 2016, Notice of Allowance.
U.S. Appl. No. 12/114,091, Jul. 13, 2016, Issue Notification.
U.S. Appl. No. 12/122,603, Mar. 3, 2011, Office Action.
U.S. Appl. No. 12/122,603, Apr. 22, 2011, Office Action.
U.S. Appl. No. 12/122,603, Sep. 23, 2011, Office Action.
U.S. Appl. No. 12/122,603, Nov. 20, 2013, Office Action.
U.S. Appl. No. 12/122,603, Apr. 30, 2014, Office Action.
U.S. Appl. No. 12/122,603, Apr. 9, 2015, Office Action.
U.S. Appl. No. 12/122,603, Sep. 23, 2015, Notice of Allowance.
U.S. Appl. No. 12/135,858, Jul. 13, 2011, Office Action.
U.S. Appl. No. 12/135,858, Feb. 16, 2012, Office Action.
U.S. Appl. No. 12/143,020, May 11, 2011, Office Action.
U.S. Appl. No. 12/143,020, Aug. 31, 2011, Office Action.
U.S. Appl. No. 12/143,020, Feb. 23, 2012, Notice of Allowance.
U.S. Appl. No. 12/338,977, Jan. 19, 2012, Office Action.
U.S. Appl. No. 12/338,977, Jul. 11, 2012, Office Action.
U.S. Appl. No. 12/338,977, Nov. 28, 2012, Office Action.
U.S. Appl. No. 12/338,977, Jun. 19, 2013, Office Action.
U.S. Appl. No. 12/393,877, Sep. 29, 2011, Office Action.
U.S. Appl. No. 12/393,877, Dec. 13, 2011, Office Action.
U.S. Appl. No. 12/393,877, May 21, 2012, Office Action.
U.S. Appl. No. 12/393,877, Aug. 4, 2014, Notice of Allowance.
U.S. Appl. No. 12/402,398, Mar. 9, 2010, Office Action.
U.S. Appl. No. 12/402,398, May 20, 2010, Office Action.
U.S. Appl. No. 12/402,398, Jan. 24, 2011, Office Action.
U.S. Appl. No. 12/402,398, Sep. 20, 2012, Office Action.
U.S. Appl. No. 12/402,398, Mar. 13, 2013, Notice of Allowance.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Office Action.
U.S. Appl. No. 12/403,277, Oct. 12, 2010, Office Action.
U.S. Appl. No. 12/403,277, Mar. 31, 2011, Office Action.
U.S. Appl. No. 12/403,277, Apr. 3, 2012, Office Action.
U.S. Appl. No. 12/403,277, Nov. 5, 2012, Office Action.
U.S. Appl. No. 12/403,277, Jan. 27, 2014, Office Action.
U.S. Appl. No. 12/403,277, Aug. 15, 2014, Office Action.
U.S. Appl. No. 12/481,377, Apr. 28, 2011, Office Action.
U.S. Appl. No. 12/481,377, Jun. 21, 2011, Office Action.
U.S. Appl. No. 12/481,377, Jan. 3, 2012, Office Action.
U.S. Appl. No. 12/481,377, Aug. 10, 2012, Notice of Allowance.
U.S. Appl. No. 12/548,274, Dec. 28, 2011, Office Action.
U.S. Appl. No. 12/548,274, Mar. 2, 2012, Office Action.
U.S. Appl. No. 12/548,274, Sep. 10, 2012, Office Action.
U.S. Appl. No. 12/548,274, Aug. 14, 2014, Office Action.
U.S. Appl. No. 12/608,769, Feb. 10, 2012, Office Action.
U.S. Appl. No. 12/608,769, Aug. 22, 2012, Office Action.
U.S. Appl. No. 12/608,769, Nov. 5, 2012, Notice of Allowance.
U.S. Appl. No. 12/608,773, Jun. 7, 2012, Office Action.
U.S. Appl. No. 12/608,773, Jul. 20, 2012, Office Action.
U.S. Appl. No. 12/608,773, Jan. 7, 2013, Office Action.
U.S. Appl. No. 12/608,773, Jul. 17, 2014, Office Action.
U.S. Appl. No. 12/608,773, Mar. 12, 2015, Office Action.
U.S. Appl. No. 12/608,773, Sep. 17, 2015, Notice of Allowance.
U.S. Appl. No. 12/642,319, Feb. 27, 2012, Office Action.
U.S. Appl. No. 12/642,319, Aug. 28, 2012, Office Action.
U.S. Appl. No. 12/642,319, Dec. 16, 2013, Office Action.
U.S. Appl. No. 12/642,319, May 27, 2014, Notice of Allowance.
U.S. Appl. No. 12/684,400, Feb. 13, 2012, Office Action.
U.S. Appl. No. 12/684,400, May 9, 2012, Office Action.
U.S. Appl. No. 12/684,400, Oct. 16, 2012, Office Action.
U.S. Appl. No. 12/684,400, Feb. 23, 2015, Office Action.
U.S. Appl. No. 12/684,400, Jul. 28, 2015, Notice of Allowance.
U.S. Appl. No. 12/684,470, Dec. 20, 2011, Office Action.
U.S. Appl. No. 12/684,470, Mar. 23, 2012, Office Action.
U.S. Appl. No. 12/684,470, Aug. 30, 2012, Office Action.
U.S. Appl. No. 12/684,470, Jun. 4, 2014, Office Action.
U.S. Appl. No. 12/684,470, Nov. 14, 2014, Office Action.
U.S. Appl. No. 12/684,470, Aug. 26, 2015, Office Action.
U.S. Appl. No. 12/684,470, Jan. 21, 2016, Office Action.
U.S. Appl. No. 12/684,470, Apr. 22, 2016, Notice of Allowance.
U.S. Appl. No. 12/684,542, Jan. 30, 2012, Office Action.
U.S. Appl. No. 12/684,542, Apr. 16, 2012, Office Action.
U.S. Appl. No. 12/684,542, Sep. 13, 2012, Office Action.
U.S. Appl. No. 12/684,542, Jun. 18, 2014, Office Action.
U.S. Appl. No. 12/684,542, Dec. 1, 2014, Office Action.
U.S. Appl. No. 12/684,562, Dec. 28, 2011, Office Action.
U.S. Appl. No. 12/684,562, Feb. 16, 2012, Office Action.
U.S. Appl. No. 12/684,562, Aug. 21, 2012, Office Action.
U.S. Appl. No. 12/684,562, Sep. 10, 2014, Office Action.
U.S. Appl. No. 12/684,562, Feb. 17, 2015, Notice of Allowance.
U.S. Appl. No. 12/684,569, Dec. 20, 2011, Office Action.
U.S. Appl. No. 12/684,569, Jan. 27, 2012, Office Action.
U.S. Appl. No. 12/684,569, Jul. 30, 2012, Office Action.
U.S. Appl. No. 12/684,569, Apr. 23, 2014, Office Action.
U.S. Appl. No. 12/688,065, Mar. 13, 2012, Office Action.
U.S. Appl. No. 12/688,065, Apr. 26, 2012, Office Action.
U.S. Appl. No. 12/688,065, Oct. 12, 2012, Office Action.
U.S. Appl. No. 12/688,065, Oct. 18, 2013, Office Action.
U.S. Appl. No. 12/688,065, Apr. 8, 2014, Office Action.
U.S. Appl. No. 12/724,304, Feb. 10, 2012, Office Action.
U.S. Appl. No. 12/848,642, Sep. 20, 2012, Office Action.
U.S. Appl. No. 12/848,642, Nov. 9, 2012, Office Action.
U.S. Appl. No. 12/848,642, Apr. 26, 2013, Office Action.
U.S. Appl. No. 12/848,642, Feb. 3, 2014, Notice of Allowance.
U.S. Appl. No. 12/850,242, Aug. 6, 2012, Office Action.
U.S. Appl. No. 12/850,242, Oct. 17, 2012, Office Action.
U.S. Appl. No. 12/850,242, Apr. 18, 2013, Office Action.
U.S. Appl. No. 12/850,242, Aug. 6, 2013, Notice of Allowance.
U.S. Appl. No. 12/897,358, Aug. 22, 2011, Office Action.
U.S. Appl. No. 12/897,358, Jan. 12, 2012, Notice of Allowance.
U.S. Appl. No. 12/897,358, Mar. 5, 2012, Notice of Allowance.
U.S. Appl. No. 12/941,809, Dec. 13, 2011, Office Action.
U.S. Appl. No. 12/941,809, Jan. 30, 2012, Office Action.
U.S. Appl. No. 12/941,809, Jun. 1, 2012, Office Action.
U.S. Appl. No. 12/941,809, Jul. 3, 2013, Office Action.
U.S. Appl. No. 12/941,809, Nov. 8, 2013, Office Action.
U.S. Appl. No. 12/941,809, Feb. 3, 2014, Notice of Allowance.
U.S. Appl. No. 12/945,646, Jan. 20, 2011, Office Action.
U.S. Appl. No. 12/945,646, Jul. 6, 2011, Office Action.
U.S. Appl. No. 12/945,646, Oct. 26, 2011, Office Action.

(56) References Cited

OTHER PUBLICATIONS

U.S. Appl. No. 12/945,646, Feb. 21, 2012, Notice of Allowance.
U.S. Appl. No. 12/950,628, Apr. 25, 2014, Notice of Allowance.
U.S. Appl. No. 12/955,859, May 26, 2011, Office Action.
U.S. Appl. No. 12/955,859, Jul. 21, 2011, Office Action.
U.S. Appl. No. 12/955,859, Dec. 15, 2011, Office Action.
U.S. Appl. No. 12/955,859, Aug. 6, 2012, Office Action.
U.S. Appl. No. 12/955,859, May 16, 2013, Office Action.
U.S. Appl. No. 12/955,859, Aug. 1, 2013, Notice of Allowance.
U.S. Appl. No. 12/961,331, Dec. 4, 2012, Office Action.
U.S. Appl. No. 12/961,331, Feb. 1, 2013, Office Action.
U.S. Appl. No. 12/961,331, Jul. 3, 2013, Office Action.
U.S. Appl. No. 12/961,331, Sep. 20, 2013, Advisory Action.
U.S. Appl. No. 12/961,331, Apr. 25, 2014, Notice of Allowance.
U.S. Appl. No. 12/966,923, Feb. 3, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/987,792, Sep. 17, 2012, Office Action.
U.S. Appl. No. 12/987,792, Jan. 21, 2014, Office Action.
U.S. Appl. No. 12/987,792, Jun. 11, 2014, Office Action.
U.S. Appl. No. 12/987,792, Aug. 25, 2014, Notice of Allowance.
U.S. Appl. No. 13/026,989, Sep. 16, 2011, Office Action.
U.S. Appl. No. 13/026,989, Jun. 8, 2012, Office Action.
U.S. Appl. No. 13/026,989, Aug. 23, 2013, Office Action.
U.S. Appl. No. 13/030,922, Dec. 18, 2012, Office Action.
U.S. Appl. No. 13/030,922, Jan. 31, 2013, Office Action.
U.S. Appl. No. 13/030,922, Jul. 18, 2013, Office Action.
U.S. Appl. No. 13/030,922, Jan. 8, 2014, Notice of Allowance.
U.S. Appl. No. 13/039,087, Jul. 17, 2012 Office Action.
U.S. Appl. No. 13/039,087, Nov. 6, 2012, Notice of Allowance.
U.S. Appl. No. 13/112,618, Mar. 29, 2013, Office Action.
U.S. Appl. No. 13/112,618, Jun. 7, 2013, Office Action.
U.S. Appl. No. 13/112,618, Nov. 20, 2013, Office Action.
U.S. Appl. No. 13/112,618, Dec. 15, 2014, Office Action.
U.S. Appl. No. 13/112,618, May 18, 2015, Office Action.
U.S. Appl. No. 13/112,618, Jan. 29, 2016, Office Action.
U.S. Appl. No. 13/112,618, Jul. 6, 2016, Notice of Allowance.
U.S. Appl. No. 13/112,631, Mar. 29, 2013, Office Action.
U.S. Appl. No. 13/112,631, Jun. 26, 2013, Office Action.
U.S. Appl. No. 13/112,631, Dec. 2, 2013, Office Action.
U.S. Appl. No. 13/112,631, Nov. 20, 2014, Office Action.
U.S. Appl. No. 13/112,631, Apr. 15, 2015, Office Action.
U.S. Appl. No. 13/153,594, Jan. 29, 2013, Office Action.
U.S. Appl. No. 13/153,594, May 29, 2013, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/222,899, Jul. 31, 2014, Office Action.
U.S. Appl. No. 13/222,899, Apr. 1, 2015, Office Action.
U.S. Appl. No. 13/222,899, Aug. 5, 2015, Office Action.
U.S. Appl. No. 13/222,899, Jan. 7, 2016, Notice of Allowance.
U.S. Appl. No. 13/308,227, Apr. 10, 2013, Office Action.
U.S. Appl. No. 13/308,227, Sep. 11, 2013, Office Action.
U.S. Appl. No. 13/308,227, Jul. 14, 2015, Office Action.
U.S. Appl. No. 13/308,227, Feb. 1, 2016, Notice of Allowance.
U.S. Appl. No. 13/488,233, Feb. 5, 2013, Notice of Allowance.
U.S. Appl. No. 13/490,143, Jan. 4, 2013, Office Action.
U.S. Appl. No. 13/490,143, Apr. 29, 2013, Notice of Allowance.
U.S. Appl. No. 13/525,839, Apr. 1, 2013, Office Action.
U.S. Appl. No. 13/525,839, Jul. 15, 2013, Notice of Allowance.
U.S. Appl. No. 13/615,547, Jan. 18, 2013, Office Action.
U.S. Appl. No. 13/615,547, Apr. 12, 2013, Notice of Allowance.
U.S. Appl. No. 13/725,589, Sep. 17, 2015, Office Action.
U.S. Appl. No. 13/725,589, Mar. 18, 2016, Notice of Allowance.
U.S. Appl. No. 13/791,829, May 29, 2013, Office Action.
U.S. Appl. No. 13/791,829, Oct. 8, 2013, Notice of Allowance.
U.S. Appl. No. 13/791,846, Jun. 4, 2015, Office Action.
U.S. Appl. No. 13/791,846, Oct. 27, 2015, Notice of Allowance.
U.S. Appl. No. 13/837,801, Dec. 16, 2015, Office Action.
U.S. Appl. No. 13/83,7801, Jun. 9, 2016, Office Action.
U.S. Appl. No. 13/898,202, Jan. 3, 2014, Office Action.
U.S. Appl. No. 13/898,202, Aug. 21, 2014, Office Action.
U.S. Appl. No. 13/898,202, Feb. 10, 2015, Notice of Allowance.
U.S. Appl. No. 13/908,796, Jul. 21, 2015, Office Action.
U.S. Appl. No. 13/908,796, Nov. 6, 2015, Notice of Allowance.
U.S. Appl. No. 14/017,039, Jan. 23, 2015, Office Action.
U.S. Appl. No. 14/017,039, Jun. 10, 2015, Office Action.
U.S. Appl. No. 14/017,039, Oct. 27, 2015, Office Action.
U.S. Appl. No. 14/017,039, Apr. 4, 2016, Notice of Allowance.
U.S. Appl. No. 14/017,039, Jul. 5, 2016, Issue Notification.
U.S. Appl. No. 14/023,428, Jul. 27, 2015, Office Action.
U.S. Appl. No. 14/023,428, Feb. 9, 2016, Office Action.
U.S. Appl. No. 14/023,428, Jun. 13, 2016, Office Action.
U.S. Appl. No. 14/077,007, Jul. 27, 2015, Office Action.
U.S. Appl. No. 14/077,007, Jan. 29, 2016, Office Action.
U.S. Appl. No. 14/246,926, Aug. 5, 2015, Office Action.
U.S. Appl. No. 14/246,926, Nov. 23, 2015, Office Action.
U.S. Appl. No. 14/246,926, Jun. 15, 2016, Office Action.
U.S. Appl. No. 14/246,973, Aug. 3, 2015, Office Action.
U.S. Appl. No. 14/246,973, Nov. 24, 2015, Office Action.
U.S. Appl. No. 14/246,973, Jul. 7, 2016, Office Action.
U.S. Appl. No. 14/312,339, Jan. 22, 2016, Office Action.
U.S. Appl. No. 14/312,339, May 3, 2016, Office Action.
U.S. Appl. No. 14/323,753, Nov. 3, 2015, Office Action.
U.S. Appl. No. 14/323,753, Apr. 15, 2016, Notice of Allowance.
U.S. Appl. No. 14/466,576, Jul. 8, 2015, Office Action.
U.S. Appl. No. 14/466,576, Dec. 15, 2015, Notice of Allowance.
U.S. Appl. No. 14/539,830, Jan. 29, 2016, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 14/312,339, Jul. 19, 2018, Notice of Allowance.
U.S. Appl. No. 15/056,281, Aug. 27, 2018, Advisory Action.
U.S. Appl. No. 15/069,230, Aug. 7, 2018, Office Action.
U.S. Appl. No. 15/356,028, Aug. 29, 2018, Office Action.
U.S. Appl. No. 15/419,335, Aug. 13, 2018, Office Action.
U.S. Appl. No. 16/144,195, filed Sep. 27, 2018, Walberg et al.
U.S. Appl. No. 14/855,080, Sep. 21, 2018, Office Action.
U.S. Appl. No. 15/056,281, Sep. 19, 2018, Office Action.
U.S. Appl. No. 15/069,230, Oct. 22, 2018, Advisory Action.
U.S. Appl. No. 15/356,028, Nov. 20, 2018, Notice of Allowance.
U.S. Appl. No. 15/419,335, Oct. 1, 2018, Interview Summary.
U.S. Appl. No. 14/855,080, Apr. 15, 2019, Office Action.
U.S. Appl. No. 15/056,281, Apr. 17, 2019, Notice of Allowance.
U.S. Appl. No. 15/069,230, Mar. 19, 2019, Office Action.
U.S. Appl. No. 15/069,230, May 1, 2019, Interview Summary.
U.S. Appl. No. 15/056,281, Jan. 14, 2019, Office Action.
U.S. Appl. No. 15/344,978, Dec. 10, 2018, Office Action.
U.S. Appl. No. 15/356,028, Jan. 23, 2019, Issue Notification.
U.S. Appl. No. 15/419,335, Nov. 30, 2018, Notice of Allowance.
U.S. Appl. No. 15/069,230, Jun. 19, 2019, Notice of Allowance.
U.S. Appl. No. 15/069,230, Aug. 28, 2019, Issue Notification.

* cited by examiner

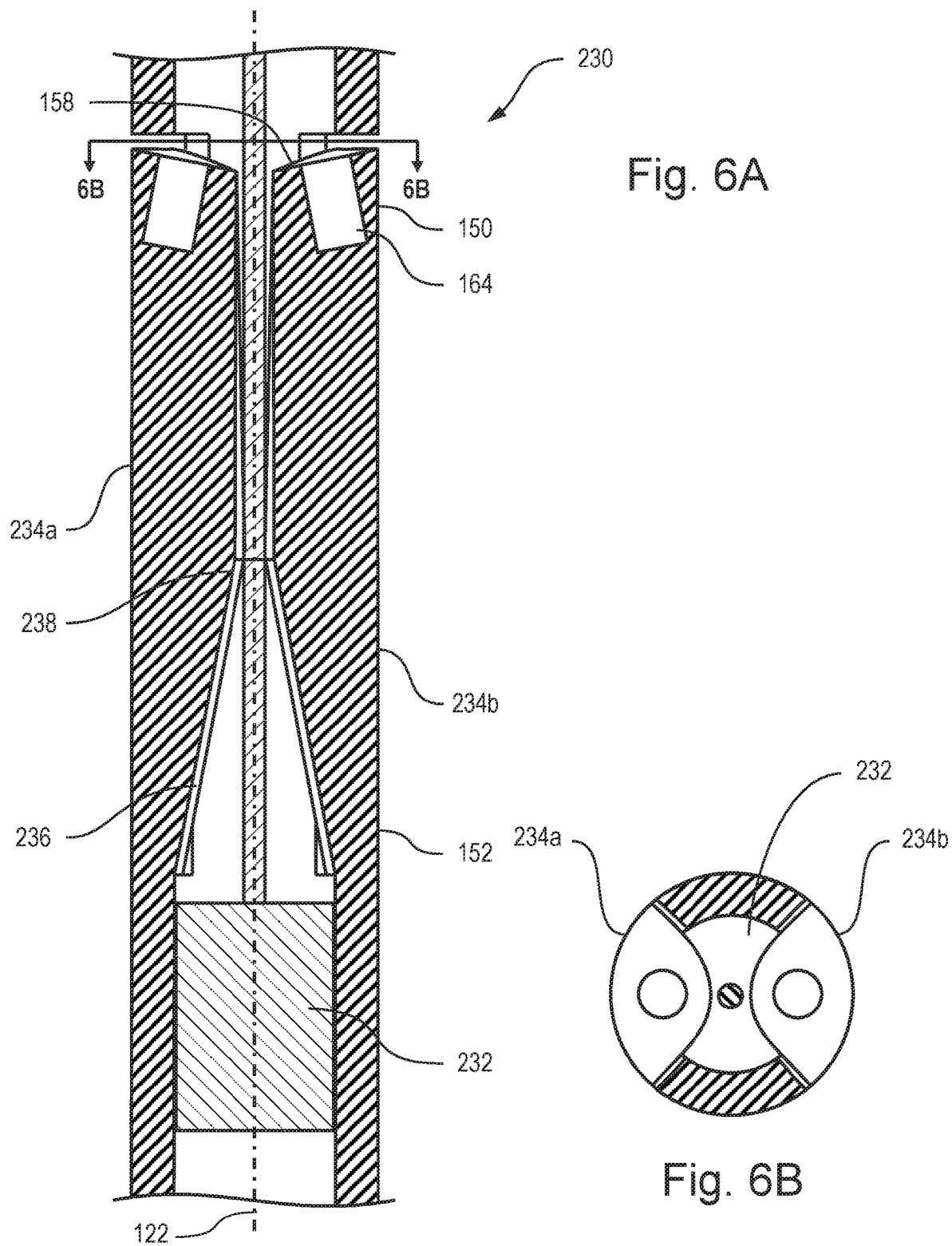

ARTICULATING SUTURING DEVICE

CROSS-REFERENCE TO RELATED APPLICATIONS

This application is a continuation of U.S. patent application Ser. No. 13/725,589, filed Dec. 21, 2012, the entire contents of which are incorporated by reference herein.

BACKGROUND OF THE INVENTION

1. The Field of the Invention

The present disclosure provides apparatuses and methods that are suitable for closure of vascular punctures or other openings in bodily tissues. More particularly, the present disclosure relates to apparatuses and techniques for tightening sutures about an opening to close the opening, which is usually accessed through a tissue tract.

2. The Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique, as described, for example, in William Grossman's "Cardiac Catheterization and Angioplasty," 3.sup.rd Ed., Lea and Febiger, Philadelphia, 1986, incorporated herein by reference. Vascular access is generally provided through an introducer sheath, which is positioned to extend from outside the patient body into the vascular lumen.

When vascular access is no longer required, the introducer sheath is removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time consuming, frequently requiring a half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take up to two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation so as to assure continued hemostasis. During this time renewed bleeding may occur, resulting in blood loss through the tract, hematoma and/or pseudoaneurysm formation, as well as arteriovenous fistula formation. These complications may require blood transfusion and/or surgical intervention.

The incidence of complications from compression-induced hemostasis increases when the size of the introducer sheath grows larger, and/or when the patient is anticoagulated. It is clear that the compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel. Locating the fastener too far from that interface can result in failure to provide hemostasis, and subsequent hematoma and/or pseudo-aneurysm formation. Conversely, if the sealing body intrudes into the arterial lumen, intravascular clots and/or collagen pieces with thrombus attached can form and embolize downstream, causing vascular occlusion. Also, thrombus formation on the surface of a sealing body protruding into the lumen can cause a stenosis, which can obstruct normal blood flow. Other possible complications include infection, as well as adverse reaction to the collagen or other implant.

A more effective approach for vascular closure has been proposed in U.S. Pat. Nos. 5,417,699, 5,613,974; and PCT published Patent Application No. PCT/US96/10271 filed on Jun. 10, 1996, the full disclosures of which are incorporated herein by reference. A suture-applying device is introduced through the tissue tract with a distal end of the device extending through the vascular puncture. One or more needles in the device are then used to draw suture through the blood vessel wall on opposite sides of the puncture, and the suture is secured directly over the adventitial surface of the blood vessel wall to provide highly reliable closure.

While a significant improvement over the use of manual pressure, clamps, and collagen plugs, certain design criteria have been found to be important to successful suturing to achieve vascular closure. For example, it is highly beneficial to properly direct the needles through the blood vessel wall at a significant distance from the puncture so that the suture is well anchored in the tissue and can provide tight closure. It is also highly beneficial to insure that the needle deployment takes place when the device is properly positioned relative to the vessel wall. The ease of deployment and efficacy of the procedure can further be enhanced by reducing the cross-section of that portion of the device, which is inserted into the tissue tract and/or the vessel itself, which may also allow closure of the vessel in a relatively short amount of time without imposing excessive injury to the tissue tract or vessel.

For the above reasons, it would be desirable to provide improved devices, systems, and methods for suturing vascular punctures. The new device should have the capability of delivering one or more pre-tied knot to an incision site. It would be particularly beneficial if these improved devices provided some or all of the benefits while overcoming one or more of the disadvantages discussed above.

BRIEF SUMMARY OF THE INVENTION

The present disclosure provides apparatuses and methods that are suitable for closure of vascular punctures or other openings in bodily tissues. More particularly, the present disclosure relates to apparatuses and techniques for tightening sutures about a tissue opening to close the opening, which is usually accessed through a tissue tract.

In one aspect of the invention, there is provided an apparatus for closing an opening in a body tissue. The apparatus has a shaft, first and second arms, and an expander. The shaft extends along an axis between a proximal end and a spaced apart distal end. The shaft has a size and configuration suitable for insertion through an opening in body tissue. The first and second arms each extend between a proximal end and a distal end. The distal end of each arm is hingedly attached to or integrally formed with the shaft. The first and second arms are movable between a retracted configuration, in which the first and second arms are each aligned along the shaft, and a deployed configuration, in which the proximal end of each of the first and second arms pivot respectively about the distal end of the respective arm so as to extend laterally away from the shaft. The expander is positioned within the shaft, and movement of the expander causes the first and second arms to move between the retracted and deployed configurations.

The proximal ends of the arms can extend laterally away from the shaft in opposite directions in the deployed configuration. The expander can be positioned within a lumen of the shaft, can be substantially conical, and can be threaded. Movement of the expander in the distal direction can cause the proximal ends of the arms to laterally move to the deployed configuration. Alternatively, movement of the expander in the proximal direction can cause the proximal ends of the arms to laterally move to the deployed configuration.

The apparatus can also include a flexible filament having first and second ends that are removably coupled with the first and second arms, respectively, and first and second penetrators positioned proximal of the first and second arms. The first and second penetrators can be advanceable distally from the shaft to the first and second arms in the deployed configuration.

The apparatus can also include third and fourth arms, each extending between a proximal end and a distal end. The distal ends of the third and fourth arms can be hingedly attached to or integrally formed with the shaft and the fourth arm can be laterally spaced apart from the third arm. The third and fourth arms can also be movable between a retracted configuration, in which the third and fourth arms are each aligned along the shaft, and a deployed configuration, in which the proximal end of each of the third and fourth arms pivot respectively about the distal end of the respective arm so as to extend laterally away from the shaft. The third and fourth arms can be caused to move between the retracted and deployed configurations by movement of the expander. The proximal ends of the third and fourth arms can extend laterally away from the shaft in opposite directions in the deployed configuration that are different than the lateral directions of the proximal ends of the first and second arms.

The apparatus can also include a second flexible filament having first and second ends that are removably coupled with the third and fourth arms, respectively, and third and fourth penetrators positioned proximal of the third and fourth arms. The third and fourth penetrators can be advanceable distally from the shaft to the third and fourth arms in the deployed configuration.

In another aspect of the invention there is provided a method for closing an opening extending through a tissue wall. The method includes the steps of inserting a distal end of a tissue locator distally through the opening, the tissue locator comprising a first arm and a second arm each extending between a proximal end and a distal end, the first and second arms each being aligned along a shaft of the tissue locator in a retracted configuration, the tissue locator being inserted far enough through the opening that the first and second arms are positioned distal of the tissue wall, first and second ends of a flexible filament respectively being removably coupled with the first and second arms; pivoting the proximal end of each of the first and second arms of the tissue locator about the distal end of the respective arm to move the proximal ends of the first and second arms from the retracted configuration to a deployed configuration in which the proximal ends of the first and second arms extend laterally away from the shaft; advancing a first penetrator and a second penetrator distally through the vessel wall such that the first and second penetrators respectively couple with the first and second ends of the flexible filament; and withdrawing the first and second penetrators proximally through the vessel wall, thereby causing the first and second ends of the filament to uncouple from the first and second arms, the first end of the flexible filament remaining coupled with the first penetrator such that the first end of the filament withdraws proximally through the vessel wall with the first penetrator.

The distal ends of the arms can remain aligned along a shaft of the tissue locator in the deployed configuration. The distal ends of the arms can be integrally formed with the shaft of the tissue locator. Alternatively, the distal ends of the arms can be hingedly attached to the shaft of the tissue locator. The distal ends of the arms can flex outward when the proximal ends of the arms move to the deployed configuration. The proximal ends of the first and second arms can extend in opposite lateral directions when the arms are in the deployed configuration. The second end of the flexible filament can remain coupled with the second penetrator such that the second end of the filament withdraws proximally through the vessel wall with the second penetrator.

The step of pivoting the proximal ends of the arms can be accomplished by moving an arm expander axially along the shaft so as to cause a laterally outward force to occur on the arms. The step of moving the arm expander axially can be accomplished by moving the arm expander proximally to cause the laterally outward force to occur on the arms. Alternatively, the step of moving the arm expander axially can be accomplished by moving the arm expander distally to cause the laterally outward force to occur on the arms.

The tissue locator can further include third and fourth arms each extending between a proximal end and a distal end, and first and second ends of a second flexible filament can be removably coupled with the third and fourth arms. The third and fourth arms can also each be aligned along the shaft of the tissue locator in the retracted configuration and positioned distal of the tissue wall when the tissue locator is inserted through the opening.

The method can further include: pivoting the proximal end of each of the third and fourth arms of the tissue locator about the distal end of the respective arm to move the proximal ends of the third and fourth arms from the retracted configuration to a deployed configuration in which the proximal ends of the third and fourth arms extend laterally away from the shaft; advancing a third penetrator and a fourth penetrator distally through the vessel wall such that the third and fourth penetrators respectively couple with the first and second ends of the second flexible filament; and withdrawing the third and fourth penetrators proximally through the vessel wall, thereby causing the first and second ends of the second filament to uncouple from the third and fourth arms, the first end of the second flexible filament remaining coupled with the third penetrator such that the first end of the second filament withdraws proximally through the vessel wall with the third penetrator.

The second end of the second flexible filament can remain coupled with the fourth penetrator such that the second end of the second filament withdraws proximally through the vessel wall with the fourth penetrator.

The step of pivoting the proximal end of each of the third and fourth arms of the tissue locator can be performed concurrently with pivoting the proximal end of each of the first and second arms; and the step of withdrawing the third and fourth penetrators proximally through the vessel wall can be performed concurrently with drawing the first and second penetrators proximally through the vessel wall. The proximal ends of the third and fourth arms can extend in opposite lateral directions from each other and in lateral directions different than the lateral directions of the proximal ends of the first and second arms when the third and fourth arms are in the deployed configuration. The step of moving the arm expander axially along the shaft can also cause a laterally outward force to occur on the third and fourth arms to pivot the third and fourth arms laterally outward.

In another aspect of the invention, there is provided an apparatus for closing an opening in a body tissue. The apparatus has a shaft, three or more arms, and an expander. The shaft extends along an axis and has a size and configuration suitable for insertion through an opening in body tissue. The three arms are attached to or integrally formed with the shaft and are laterally spaced apart from each other. The arms are movable between a retracted configuration, in which the arms are each aligned along the shaft, and a deployed configuration, in which the arms each extend laterally away from the shaft in different directions. The expander causes the arms to move between the retracted and deployed configurations.

The apparatus can include a plurality of flexible filaments each having first and second ends that are removably coupled with separate ones of the three or more arms, and a penetrator associated with each arm. Each penetrator can be positioned proximal of the respective arm, and can be advanceable distally from the shaft to the respective arm in the deployed configuration.

The apparatus can include a suture net having multiple ends that are each removably coupled with separate ones of the three or more arms, and a penetrator associated with each arm. Each penetrator can be positioned proximal of the respective arm, and can be advanceable distally from the shaft to the respective arm in the deployed configuration.

The three or more arms can be four to six arms. The expander can be positioned within a lumen of the shaft.

In another aspect of the invention there is provided a method for closing an opening extending through a tissue wall. The method includes the steps of inserting a distal end of a tissue locator distally through the opening, the tissue locator comprising three or more arms, each being aligned along a shaft of the tissue locator in a retracted configuration, the tissue locator being inserted far enough through the opening that the three or more arms are positioned distal of the tissue wall, an end of a filament or a filament net link being removably coupled with each of the arms; pivoting the proximal ends of each of the first and second moving the three or more arms of the tissue locator from the retracted configuration to a deployed configuration in which the three or more arms extend laterally away from the shaft in different directions; for each arm, advancing a penetrator distally through the vessel wall to couple with the end of the filament net or flexible filament associated with the arm; and withdrawing the penetrators proximally through the vessel wall, thereby causing the ends of the filament net or the filaments to uncouple from the three or more arms, at least one end of the filament net or of each flexible filament remaining coupled with at least one of the penetrators such that the corresponding end of the filament net or each filament withdraws proximally through the vessel wall with the corresponding penetrator.

All of the ends of the filament net or flexible filaments can remain coupled with the corresponding penetrators such that all of the ends of the filament net or flexible filaments withdraw proximally through the vessel wall with the three or more penetrators.

In another aspect of the invention, there is provided an apparatus for closing an opening in a body tissue. The apparatus has a shaft, a plurality of arms, a plurality of flexible filaments, and a penetrator associated with each arm. The shaft extends along an axis between a proximal end and a spaced apart distal end and has a size and configuration suitable for insertion through an opening in body tissue. The plurality of arms are attached to or integrally formed with the shaft. The plurality of flexible filaments each has a first end and a second end; the first and second ends of the flexible filaments are removably coupled with separate ones of the plurality of arms. Each penetrator is positioned proximal of the respective arm and is advanceable distally through a vessel wall to the respective arm to couple with the end of the filament associated with the arm. The penetrators are configured to withdraw at least a portion of each of the filaments through the vessel wall.

The arms can be laterally spaced apart from each other. The arms can be movable between a retracted configuration, in which the arms are each aligned along the shaft; and a deployed configuration in which the arms extend laterally away from the shaft. The apparatus can also include an expander which causes the arms to move between the retracted and deployed configurations. The expander can be positioned within a lumen of the shaft.

In another aspect of the invention there is provided a method for closing an opening extending through a tissue wall. The method includes the steps of inserting a distal end of a tissue locator distally through the opening, the tissue locator comprising a plurality of arms, each being aligned along a shaft of the tissue locator in a retracted configuration, the tissue locator being inserted far enough through the opening that the plurality of arms are positioned distal of the tissue wall, a plurality of flexible filaments being removably coupled with the plurality of arms; moving the plurality of arms from the retracted configuration to a deployed configuration in which the plurality of arms extend laterally away from the shaft; for each arm, advancing a penetrator distally through the vessel wall to couple with an end of one of the flexible filaments; and withdrawing the penetrators proximally through the vessel wall, thereby causing the ends of the filaments to uncouple from the plurality of arms, at least one end of each of the flexible filaments remaining coupled with the respective penetrator such that the coupled ends of the filaments withdraw proximally through the vessel wall with the respective penetrators.

All of the ends of the flexible filaments can remain coupled with the corresponding penetrators such that all of the ends of the filaments withdraw proximally through the vessel wall with the penetrators.

In another aspect of the invention, there is provided an apparatus for closing an opening in a body tissue. The apparatus has a shaft, a plurality of arms, a flexible net, and a penetrator associated with each arm. The shaft extends along an axis between a proximal end and a spaced apart distal end and has a size and configuration suitable for insertion through an opening in body tissue. The plurality of arms are attached to or integrally formed with the shaft. The filament net has plurality of ends; each end of the filament net is removably coupled with a separate one of the arms. Each penetrator is positioned proximal of the respective arm and is advanceable distally through a vessel wall to the respective arm to couple with the end of the filament net associated with the arm. The penetrators are configured to withdraw the ends of the filament net through the vessel wall.

The arms can be laterally spaced apart from each other. The arms can be movable between a retracted configuration, in which the arms are each aligned along the shaft; and a deployed configuration in which the arms extend laterally away from the shaft. The apparatus can also include an expander which causes the arms to move between the retracted and deployed configurations. The expander can be positioned within a lumen of the shaft. The apparatus can also include a flexible filament removably coupled with separate ones of the arms.

In another aspect of the invention there is provided a method for closing an opening extending through a tissue wall. The method includes the steps of inserting a distal end of a tissue locator distally through the opening, the tissue locator comprising a plurality of arms, each being aligned along a shaft of the tissue locator in a retracted configuration, the tissue locator being inserted far enough through the opening that the plurality of arms are positioned distal of the tissue wall, separate ends of a filament net being removably coupled with each of the arms; moving the plurality of arms of the tissue locator from the retracted configuration to a deployed configuration in which the plurality of arms extend laterally away from the shaft; for each arm, advancing a penetrator distally through the vessel wall to couple with the end of the filament net associated with the arm; and withdrawing the penetrators proximally through the vessel wall, thereby causing the ends of the filament net to uncouple from the plurality of arms and withdraw proximally through the vessel wall with the penetrators.

The step of moving the plurality of arms of the tissue locator can be accomplished by pivoting a proximal end of each arm about a distal end of the respective arm.

In another aspect of the invention, there is provided an apparatus for closing an opening in a body tissue. The apparatus has a shaft, a plurality of arms, a filament net or plurality of flexible filaments, a penetrator associated with each arm, and a plurality of penetrator actuators. The shaft extends along an axis between a proximal end and a spaced apart distal end and has a size and configuration suitable for insertion through an opening in body tissue. The plurality of arms are attached to or integrally formed with the shaft and are movable between a retracted configuration, in which the arms are each aligned along the shaft of the tissue locator, and a deployed configuration in which the arms extend laterally away from the shaft. The filament net or plurality of flexible filaments have multiple ends and each of the ends are removably coupled with a separate one of the plurality of arms. Each penetrator is positioned proximal of the respective arm and is advanceable distally through a vessel wall to the respective arm to couple with the end of the filament or filament net associated with the arm. The penetrators are configured to withdraw the ends of the filament or filament net through the vessel wall. The actuators are each associated with a different penetrator so that the penetrators are movable independent of each other by the penetrator actuators.

In another aspect of the invention there is provided a method for closing an opening extending through a tissue wall. The method includes the steps of inserting a distal end of a tissue locator distally through the opening, the tissue locator comprising a plurality of arms, each being aligned along a shaft of the tissue locator in a retracted configuration, the tissue locator being inserted far enough through the opening that the plurality of arms are positioned distal of the tissue wall, at least one flexible filament or web being removably coupled with the plurality of arms; moving the plurality of arms from the retracted configuration to a deployed configuration in which the plurality of arms extend laterally away from the shaft; for each arm, advancing a penetrator distally through the vessel wall to couple with the at least one flexible filament or web associated with the arm, the penetrators being movable independent of each other; and withdrawing the penetrators proximally through the vessel wall, thereby causing the at least one flexible filament or web to uncouple from the plurality of arms and withdraw proximally through the vessel wall with the penetrators.

Each penetrator can be advanced at different times from each other. Each penetrator can have a separate penetrator actuator associated therewith and can be advanced and withdrawn by manually manipulating the associated penetrator actuator.

In another aspect of the invention there is provided a method for closing an opening extending through a tissue wall. The method includes the steps of inserting a distal end of a tissue locator distally through the opening, the tissue locator comprising a plurality of arms, each being aligned along a shaft of the tissue locator in a retracted configuration, the tissue locator being inserted far enough through the opening that the plurality of arms are positioned distal of the tissue wall; advancing a plurality of penetrators distally to attempt to penetrate through the vessel wall, each penetrator being associated with a different one of the arms, one or more penetrators not penetrating through the vessel wall; removably coupling separate ends of a filament net with the plurality of arms, the one or more arms associated with the nonpenetrating penetrators not being coupled with the filament net; moving the plurality of arms from the retracted configuration to a deployed configuration in which the plurality of arms extend laterally away from the shaft; for each arm associated with penetrating penetrators, advancing a penetrator distally to penetrate through the vessel wall, the penetrators penetrating through the wall to couple with the end of the filament net associated with the corresponding arm; and withdrawing the penetrators proximally, thereby causing the ends of the filament net to uncouple from the plurality of arms and withdraw proximally through the vessel wall with the penetrators.

These and other advantages and features of the present disclosure will become more fully apparent from the following description and appended claims, or may be learned by the practice of the disclosure as set forth hereinafter.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements. Furthermore, multiple instances of an element may each include separate letters appended to the element number. For example two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

FIG. 3B is taken along the section line 3B-3B of FIG. 3A and FIG. 3D is taken along the section line 3D-3D of FIG. 3C;

FIG. 5B is taken along the section line 5B-5B of FIG. 5A and FIG. 5D is taken along the section line 5D-5D of FIG. 5C;

FIGS. 6A-6D are cross-sectional side and top views of another embodiment of a tissue locator that can be used in the tissue closure devices shown in FIGS. 1 and 2 showing the arms in the retracted position (FIGS. 6A and 6B) and in the deployed position (FIGS. 6C and 6D). FIG. 6B is taken along the section line 6B-6B of FIG. 6A and FIG. 6D is taken along the section line 6D-6D of FIG. 6C;

FIG. 21B is taken along the section line 21B-21B of FIG. 21A and FIG. 21D is taken along the section line 21D-21D of FIG. 21C;

FIG. 22B is taken along the section line 22B-22B of FIG. 22A and FIG. 22D is taken along the section line 22D-22D of FIG. 22C;

DETAILED DESCRIPTION

As used in the specification and appended claims, directional terms, such as "top," "bottom," "up," "down," "upper," "lower," "proximal," "distal," and the like are used herein solely to indicate relative directions and are not otherwise intended to limit the scope of the invention or claims.

The present disclosure provides methods and apparatuses to locate a distal wall of a tissue through an opening in the tissue. Some embodiments of the devices and methods described herein are suitable for closure of vascular punctures or other openings in the tissue. For example, in some embodiments, one or more sutures can be positioned through the tissue adjacent an opening so the opening can be closed using the sutures.

Generally, the apparatuses and methods described herein for tissue location can be used with any type of body tissue. Embodiments used to close openings in tissue can be used with any type of body tissue that has sufficient strength to be held together by sutures. By way of example only, embodiments of the present invention can be used to close openings in tissues that have a wall or membrane function, e.g, pulmonary, intestinal, vascular, urethral, gastric, renal or other wall structures, or in membranes, e.g., amniotic or pericardial membranes. Openings in other types of tissues can also be closed using embodiments of the present invention. Although many types of body tissue can be closed by the methods and apparatuses disclosed herein, the description included herein refers to "vessels" for convenience.

Furthermore, the apparatuses and methods described herein can be used with large and small hole punctures or other openings in the body tissue. By way of example, embodiments of the present invention can be used to close holes from 5 French to 30 French or larger. It may also be possible to close holes of other sizes using embodiments of the present invention.

Figure 1A:
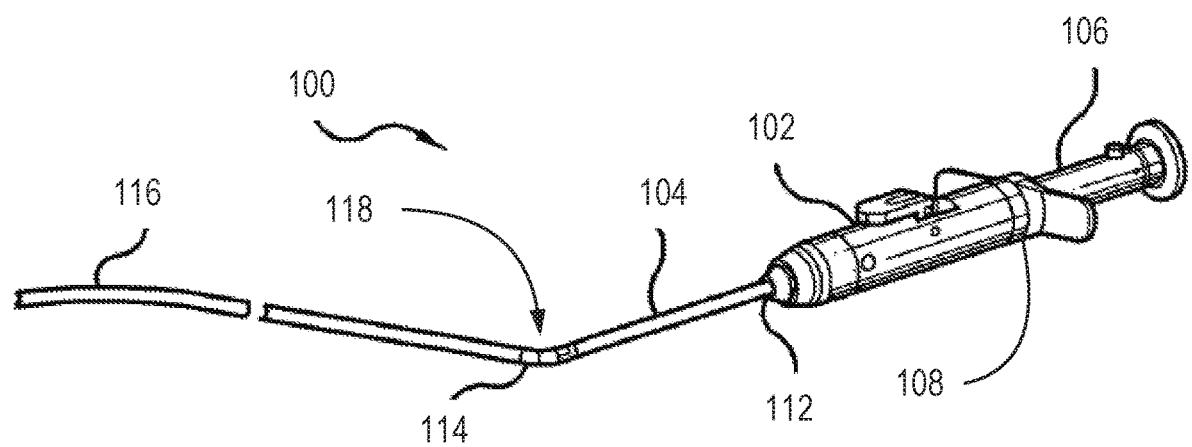
FIGS. 1A and 1B are perspective views of a tissue closure device, respectively showing a pair of arms in retracted and deployed positions according to one embodiment of the present invention.
Figure 1B:
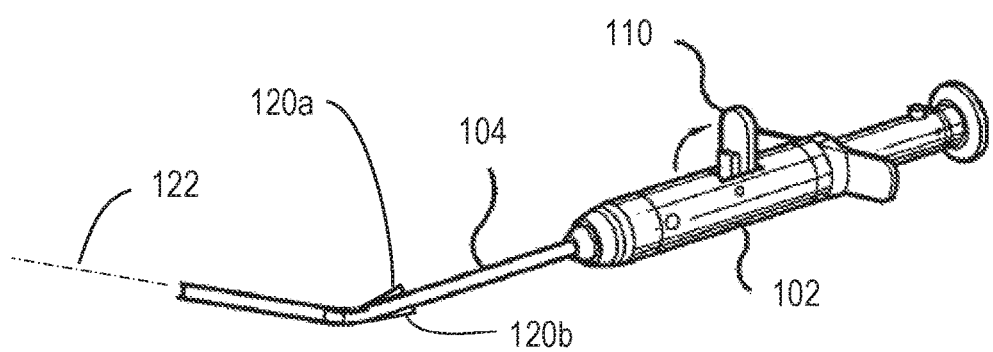

Turning now to the drawings, FIGS. 1A and 1B illustrate a tissue closure device 100 having a housing 102 and a shaft 104 extending therefrom. Housing 102 supports a penetrator actuation handle 106 at a proximal end 108 thereof, and an arm actuation handle 110. Shaft 104 extends distally from housing 102 from a proximal end 112 to a spaced apart distal end 114. A flexible, atraumatic monorail guide body 116 can extend distally from distal end 114 of shaft 104.

A tissue locator 118 is positioned at distal end 114 of shaft 104. Tissue locator 118 includes a pair of arms 120a and 120b positioned near distal end 114 of shaft 104. Arms 120 can move between a low profile, retracted position, in which each arm is substantially aligned along an axis 122 of shaft 104, to a deployed, expanded position, in which the arms extend laterally away from shaft 104. The retracted position of arms 120 is shown in FIG. 1A and the deployed position is shown in FIG. 1B. The movement of arms 120 between the retracted and deployed positions and back again can be effected by actuation of arm actuation handle 110. Arm actuation handle 110 can comprise a handle that pivots about a hinged point, as in the depicted embodiment, or can comprise a mechanism that uses a rotary action, a linear action, a cam action, or any other type of action that can move arms 120 between the retracted and deployed positions. The movement of penetrators to and from the deployed arms 120 can be effected by actuation of penetrator actuation handle 106. Penetrator actuation handle 106 can comprise a handle that linearly moves, as in the depicted embodiment, or can comprise a mechanism that uses a picoting action, a rotary action, a cam action, or any other type of action that can move the penetrators to and from the deployed arms 120.

Figure 2A:
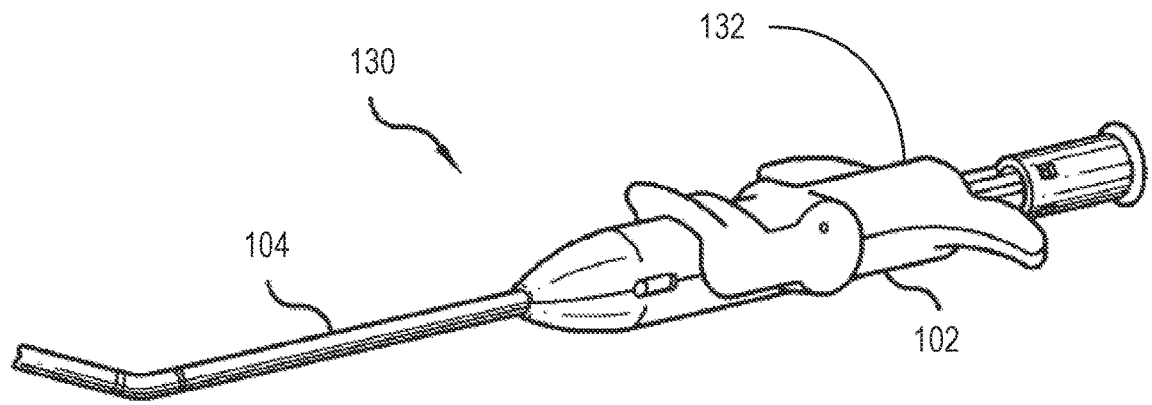
FIGS. 2A-C are perspective views of a tissue closure device according to another embodiment, showing actuation of a pair of arms and advancement of needles from a shaft to the arms.
Figure 2B:
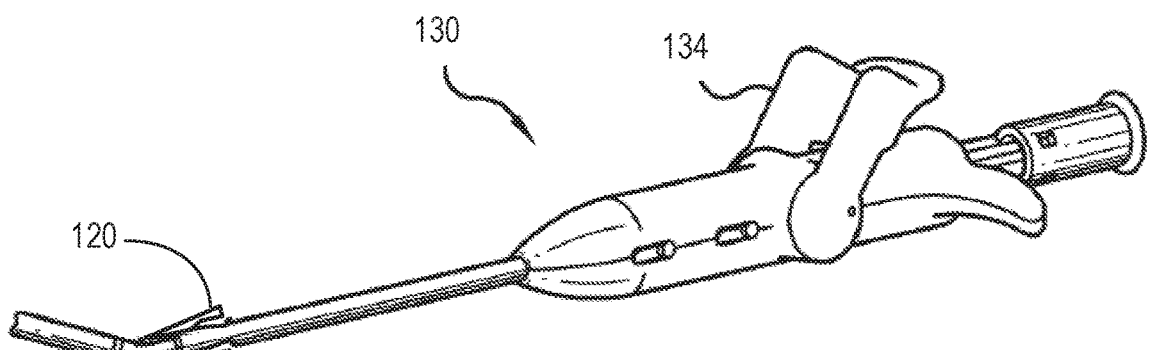
Figure 2C:
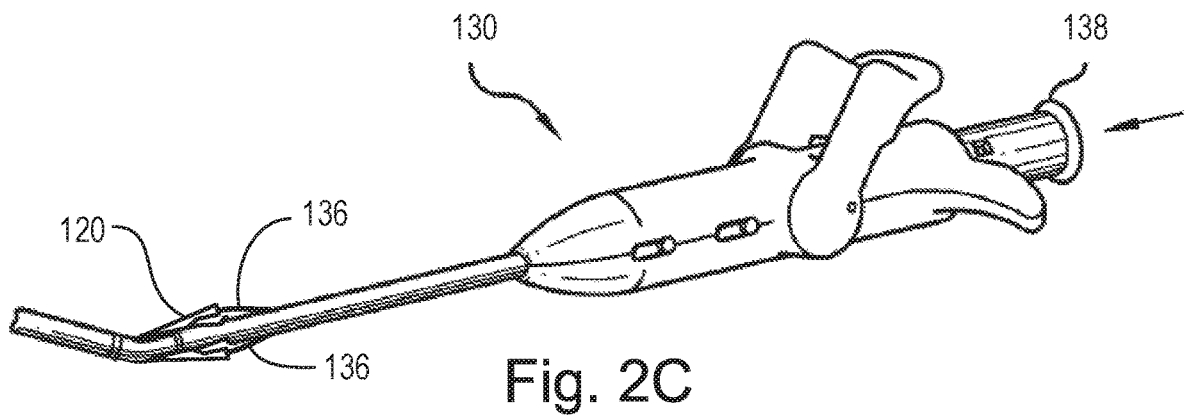

FIGS. 2A-2C illustrate another embodiment of a tissue closure device 130 having a modified proximal housing 132. Similar to tissue closure device 100, tissue closure device 130 includes a pair of arms 120 that can be moved between the retracted and deployed positions using an arm actuation handle 134. FIG. 2C also shows how penetrators 136 can be advanced distally from shaft 104 to arms 120 by depressing a penetrator actuation handle 138.

Figures 3A, 3B:
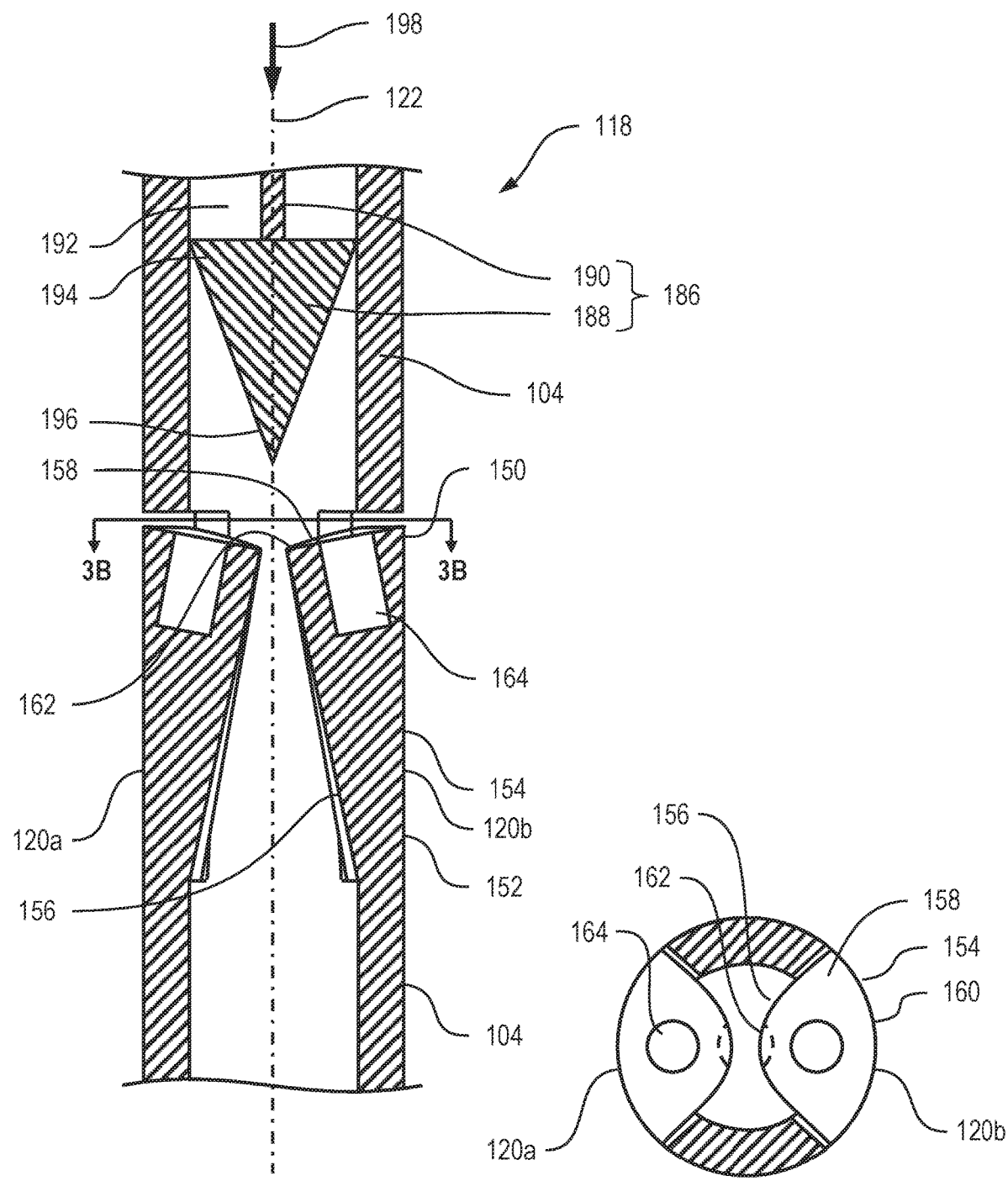
FIGS. 3A-3D are cross-sectional side and top views of one embodiment of a tissue locator that can be used in the tissue closure devices shown in FIGS. 1 and 2 showing the arms in the retracted position (FIGS. 3A and 3B) and in the deployed position (FIGS. 3C and 3D).
Figure 3C:
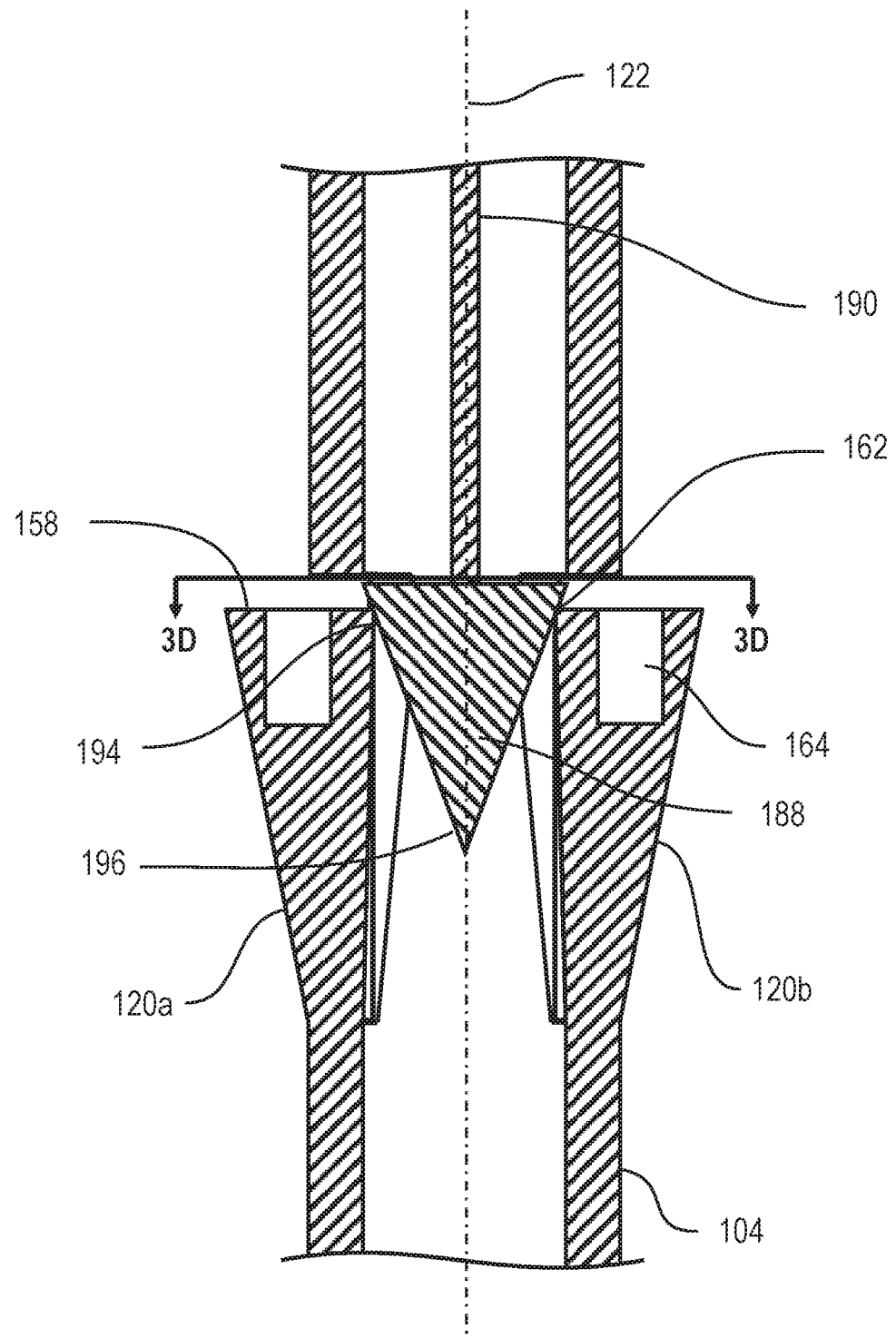
Figure 3D:
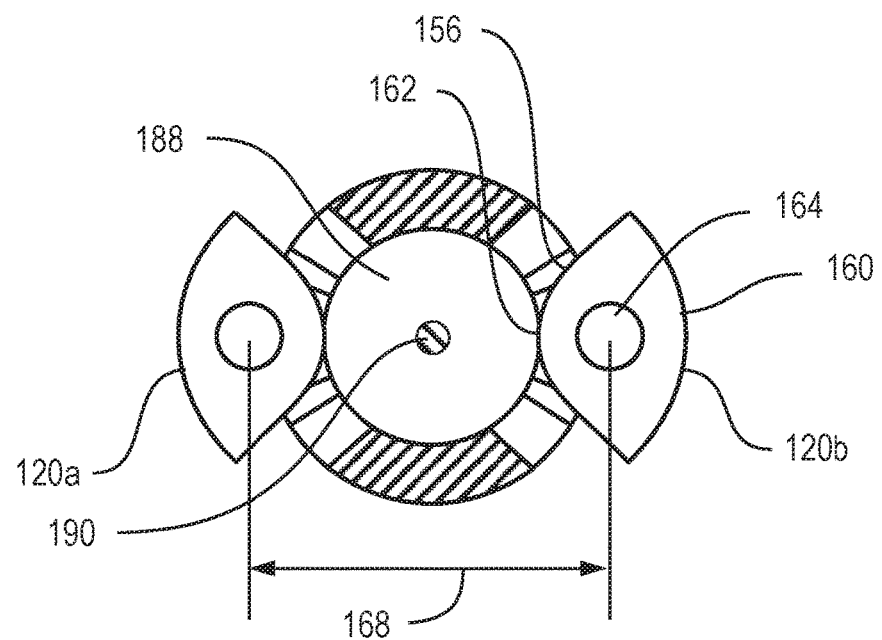
Figure 3E:
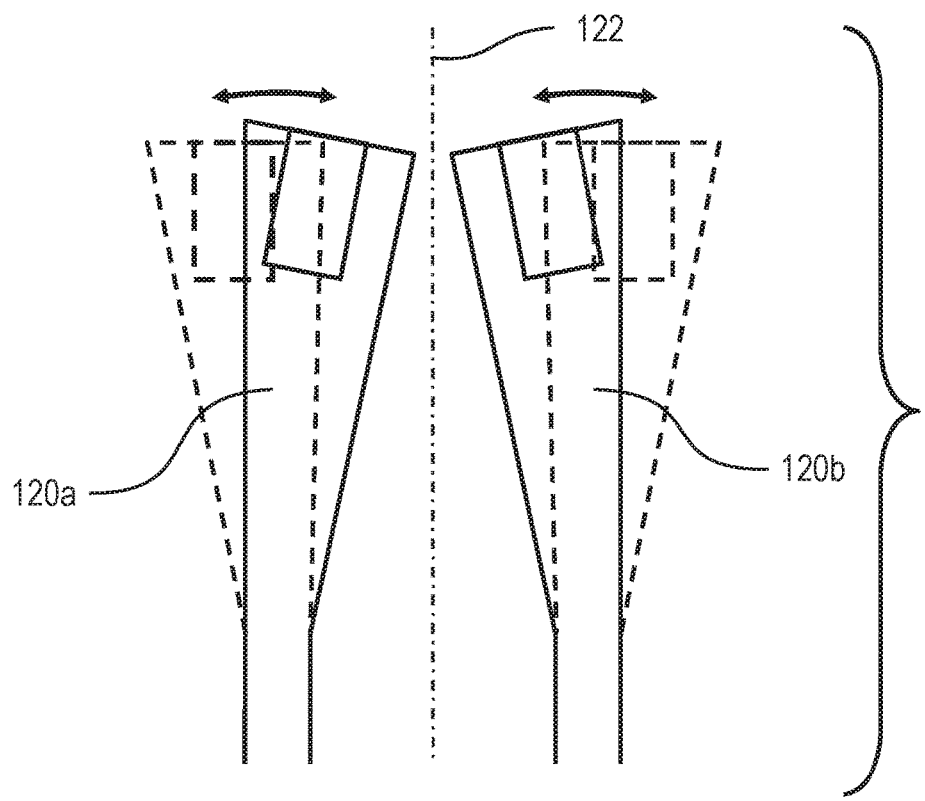
FIG. 3E depicts the movement of the arms of the tissue locator shown in FIGS. 3A-3D, between the retracted and deployed positions.

Arms 120 and the actuation thereof are illustrated more clearly in the cross sectional views of FIGS. 3A-3E. FIGS. 3A and 3B depict arms 120a and 120b in the retracted position, and FIGS. 3C and 3D depict arms 120a and 120b in the deployed position. FIG. 3E shows the movement of arms 120a and 120b between the two positions; the retracted position is shown in solid lines while the deployed position is shown in dashed lines. As can be seen in FIGS. 3A-3E, arms 120a and 120b are essentially identical except that they are positioned on opposite lateral sides of tissue locator 118 so as to be diametrically opposed to each other.

Each arm 120 of tissue locator 118 extends from a proximal end 150 to a spaced apart distal end 152. To allow arms 120 to move between the retracted and deployed positions, distal end 152 of each arm 120 is attached to or formed with shaft 104 so as to be pivotable with respect to shaft 104. That is, each arm 120 is configured to pivot about its distal end 152 to cause proximal end 150 to move radially inward and outward with respect to axis 122, as shown in FIG. 3E. This can be accomplished by making at least the distal end 152 of each arm 120 out of a resiliently bendable material. Alternatively, a hinge (not shown) can be attached between distal end 152 of arm and shaft 104 to aid in the pivoting action, if desired.

With reference to FIGS. 3A and 3B, each arm 120 has an outer surface 154 and an opposing inner surface 156 extending from distal end 152 to an end face 158 positioned at proximal end 150. Outer surface 154 faces radially away from axis 122 and can be curved to substantially match the curvature of shaft 104, if desired. Inner surface 156 faces radially towards axis 122. If desired, inner and outer surfaces 156 and 154 can be formed so that the thinnest portion (laterally) of each arm 120 occurs at the distal end 152 thereof to aid in the pivoting of the arm thereat.

In the retracted position illustrated in FIGS. 3A and 3B, arms 120a and 120b extend substantially along axis 122 of shaft 104. If outer surfaces 154 of arms 120 are curved to substantially match the curvature of shaft 104, tissue locator 118 can essentially form a bridge between the portions of shaft 104 positioned proximally and distally of arms 120. Tissue locator 118 can have a similar cross-sectional outer surface as shaft 104 when arms 120 are in the retracted position. This can be beneficial when positioning arms 120 through an opening in the tissue before deployment. Advantageously, prior to deployment of arms 120, tissue locator 118 can have a cross section of about 7 Fr or less. In some embodiments, tissue locator 118 can have a cross section of between 5 and 30 French prior to deployment of arms 120. In some embodiments, tissue closure device 100 can have a cross-section of about 6 Fr or less for the entire device distal of the proximal end 112 of shaft 104.

End faces 158 are used to determine the location of the distal surface of the tissue. This can be done by positioning arms 120 through an opening in the tissue until the arms are distal of the tissue, deploying arms 120, and then pulling tissue locator 118 proximally until end faces 158 contact the distal surface of the tissue. To aid in this, each end face 158 is substantially planar and extends from an outer edge 160 to an inner edge 162. Outer edge 160 is formed by the intersection of end face 158 with outer surface 154 and inner edge is formed by the intersection of end face 158 with inner surface 156. End face 158 generally faces proximally and can be substantially orthogonal to outer surface 154 and/or inner surface 156, or can be at any desired angle with respect to inner or outer surfaces 156 or 154. In the depicted embodiment, each end face 158 is formed so as to be substantially perpendicular to axis 122 when the corresponding arm 120 is in the deployed position, as shown in FIG. 3C.

End faces 158 can be of any desired cross-sectional shape. In the depicted embodiment, outer edge 160 of each end face 158 is in the shape of an arc that substantially matches the diameter of shaft 104. Inner edge 162 extends from either end of outer edge 160 towards axis 122 and is substantially rounded off, as shown in FIGS. 3B and 3D. If desired, the innermost portion of each inner edge 162 can alternatively be shaped as a smaller arc of an inner circle, as depicted by dashed lines in FIG. 3B, to provide more contact with expanders used to move arms 120 between the retracted and deployed positions. Of course, other shapes can also be used.

Figure 3F:
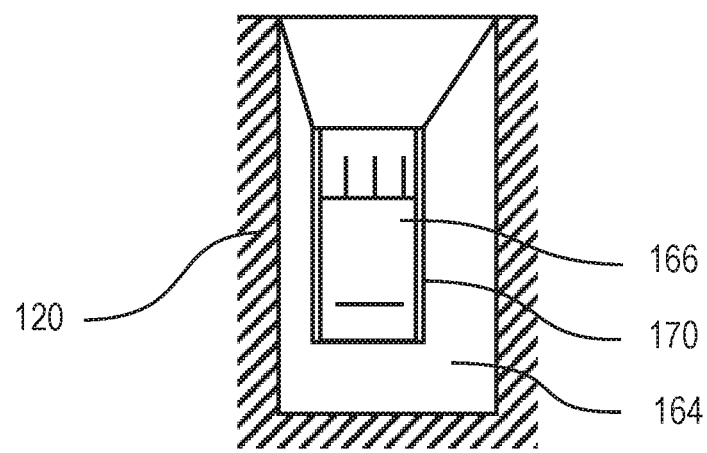
FIG. 3F is a close-up cross-sectional view of a penetrator receptacle with a cuff disposed therein.

A penetrator receptacle 164 can be formed on end face 158 of each arm so as to generally face proximally. As shown in the close-up view of FIG. 3F, a releasable cuff 166 may be disposed within each penetrator receptacle 164. As such, the penetrator receptacles can also be referred to as cuff pockets. A surface of each receptacle 164 can taper proximally and outwardly to guide advancing penetrators, such as, e.g., needles or other elongated bodies, into engagement with cuffs 166 positioned therein when arms 120 are in the deployed position, as discussed in more detail below.

When in the deployed position, penetrator receptacles 164 can define a lateral width 168 (FIG. 3D) that can be in a range from about 0.10 inches to about 0.612 inches, with about 0.110 inches to about 0.30 inches being common. Other widths can also be used.

In one embodiment, penetrator receptacles 164 can each include a cuff recess 170 into which cuffs 166 can be positioned. In one embodiment, each cuff recess 170 has a diameter about a centerline of cuff 166 of about 0.0230 inches and a length of about 0.042 inches. In some embodiments, penetrator receptacles 164 can taper outward at an angle between about 20 degrees and about 35 degrees from centerline. A lateral opening or window through the side of arm 120 to each cuff recess may be included to facilitate penetrator and/or cuff positioning during assembly. A protruding collar may be positioned near the proximal end of cuff recess to help keep cuff 166 in position. A slot may also be positioned adjacent penetrator receptacle 164 to receive a suture or other filament, as discussed in more detail below.

Figure 4:
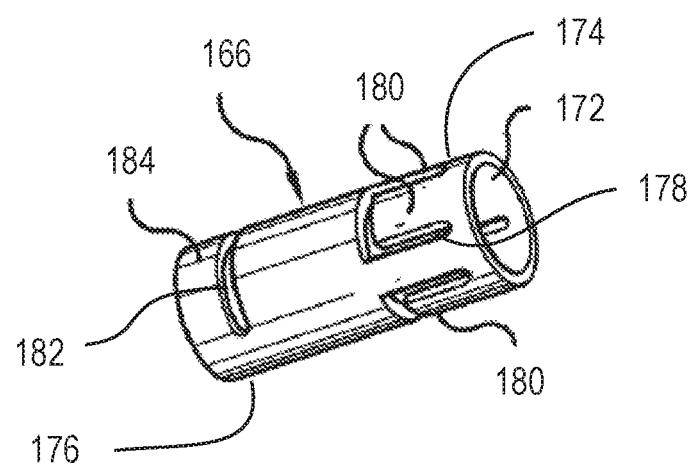
FIG. 4 is a perspective view of a cuff that can be used with embodiments of the present invention.

Turning to FIG. 4, cuff 166 can be a roughly cylindrical structure having an axial channel 172 extending therethrough between a proximal end 174 and a distal end 176. A first slot 178 can be formed at proximal end 174 of cuff 166 to define at least one tab 180. Tabs 180 can be used to aid in capturing a penetrator inserted into channel 172, as discussed below. A second slot 182 can be formed at distal end 176 of cuff 166 to define a suture attachment collar 184. Suture attachment collar 184 can be used to facilitate attachment of a suture or other filament to cuff 166, also as discussed below. Cuff 166 can be comprised of a resilient material, such as a metal or alloy. For example, in one embodiment, cuff 166 can be comprised of stainless steel.

Returning to FIGS. 3A and 3C, tissue locator 118 can also include an arm expansion mechanism to help in moving arms 120 between the retracted and deployed positions. For example, in the depicted embodiment, an arm expansion mechanism 186 can comprise an expander 188 that is moved along axis 122 by an actuator 190. Actuator 190 can extend proximally from expander 188 through a lumen 192 of shaft 104 or along the outside surface of shaft 104 and can be coupled to arm actuation handle 110 or 134 (FIG. 1B or 2B). Actuator 190 can be a rod or the like. Other types of actuators can alternatively be used.

In the depicted embodiment, expander 188 can comprise a substantially conical wedge extending distally from a base 194 to a substantially narrower distal end 196. When arms 120 are in the retracted position, expander 188 can be positioned within shaft 104 proximal of arms 120, as shown in FIG. 3A. Actuation of arm actuation handle 110 or 134 (FIG. 1B or 2B) can cause actuator 190 to advance distally, as denoted by arrow 198, thereby causing expander 188 to also advance distally. Eventually, distal end 196 of expander 188 contacts inner edge 162 of each arm end face 158. As expander 188 is advanced further distally by actuator 190, the expander begins to exert an outward force on arms 120 at inner edges 162. Because distal end 152 of each arm 120 is attached to or formed with shaft 104, however, distal end 152 cannot be moved radially outward by the exerted force. On the other hand, proximal end 150 of each arm 120 is unattached to shaft 104 and can therefore move radially outward in response to the exerted force, pivoting about distal end 152 to do so. As a result, each arm 120 begins to pivot radially outward about distal end 152.

Due to the wedge shape of expander 188, as expander 188 advances further distally, the outward force exerted by expander 188 against inner edges 162 causes each arm 120 to continue to pivot radially outward about distal end 152. Proximal ends 150 of arms 120 can continue to be pushed radially outward by expander 188 until distal end 196 of expander 188 reaches inner edges 162 of arms 120. At that point, proximal ends 150 of arms 120 are in the deployed position shown in FIGS. 3C and 3D. As noted above, in the deployed position, arms 120 can be used to locate the distal wall of the tissue through the tissue opening, as discussed in more detail below.

To move arms 120 back to the retracted position shown in FIGS. 3A and 3B, arm actuation handle 110 or 134 (FIG. 1B or 2B) can be moved back to its original position, thereby causing actuator 190 to retract proximally. This causes expander 188 to also move proximally, thereby allowing the proximal end 150 of arms 120 to move radially back towards axis 122. To aid in moving arms 120 back to the retracted position, each arm 120 can be made of a resilient material that biases the arm towards the retracted position. For example, arms 120 can be made of a resilient polymer, metal, alloy, or the like. A shape memory alloy, such as, e.g., a nickel titanium allow, commonly known as nitinol, can also be used. Alternatively, a biasing element, such as, e.g., a spring, can be attached between arms 120 to bias the arms to the retracted position.

In an alternative embodiment, expander 188 can be threaded. In that embodiment, rotation of actuator 188 about axis 122 can cause expander 188 to rotate. Due to the threaded connection with inner edges 162, this can cause expander 188 to move distally with respect to arms 120, thereby rotating arms 120 to the deployed position. If desired, to make the threaded connection stronger, each inner edge 162 can also include a portion of a thread that mates with the thread on expander 188, as indicated by the dashed lines shown on FIG. 3B. To actuate the threaded expander, a rotating arm actuation handle can be used.

Figures 5A, 5B:
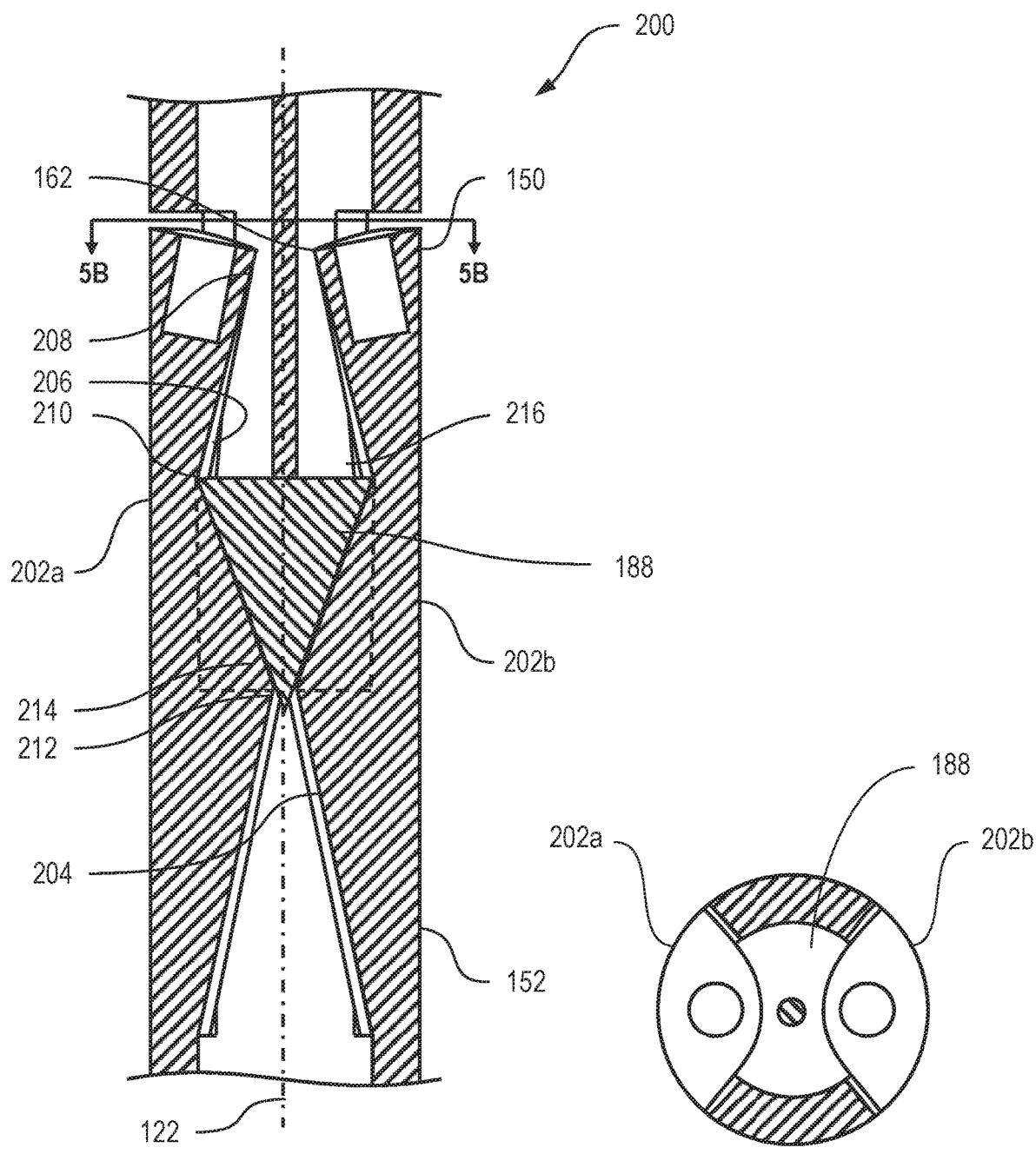
FIGS. 5A-5D are cross-sectional side and top views of another embodiment of a tissue locator that can be used in the tissue closure devices shown in FIGS. 1 and 2 showing the arms in the retracted position (FIGS. 5A and 5B) and in the deployed position (FIGS. 5C and 5D).

FIGS. 5A-5D show an alternative embodiment of a tissue locater 200 that allows for further lateral movement of the arms than tissue locater 118. Tissue locater 200 includes arms 202a and 202b that are substantially longer than arms 120, with an inner surface 204 of each arm being shaped to include a recess 206 between proximal and distal ends 150 and 152, as shown in FIG. 5A. Each recess 206 extends from a proximal end 208 distally outward to an outer edge 210 and then inward to an inner edge 212 at a distal end 214.

Inner edge 212 is closer to axis 122 than is outer end 210. The recesses 206 of arms 202 combine to generally form a cavity 216. Recesses 206 are shaped so that when arms 202 are in the retracted position, expander 188 can be positioned within cavity 216, as shown in FIG. 5A.

Figure 5C:
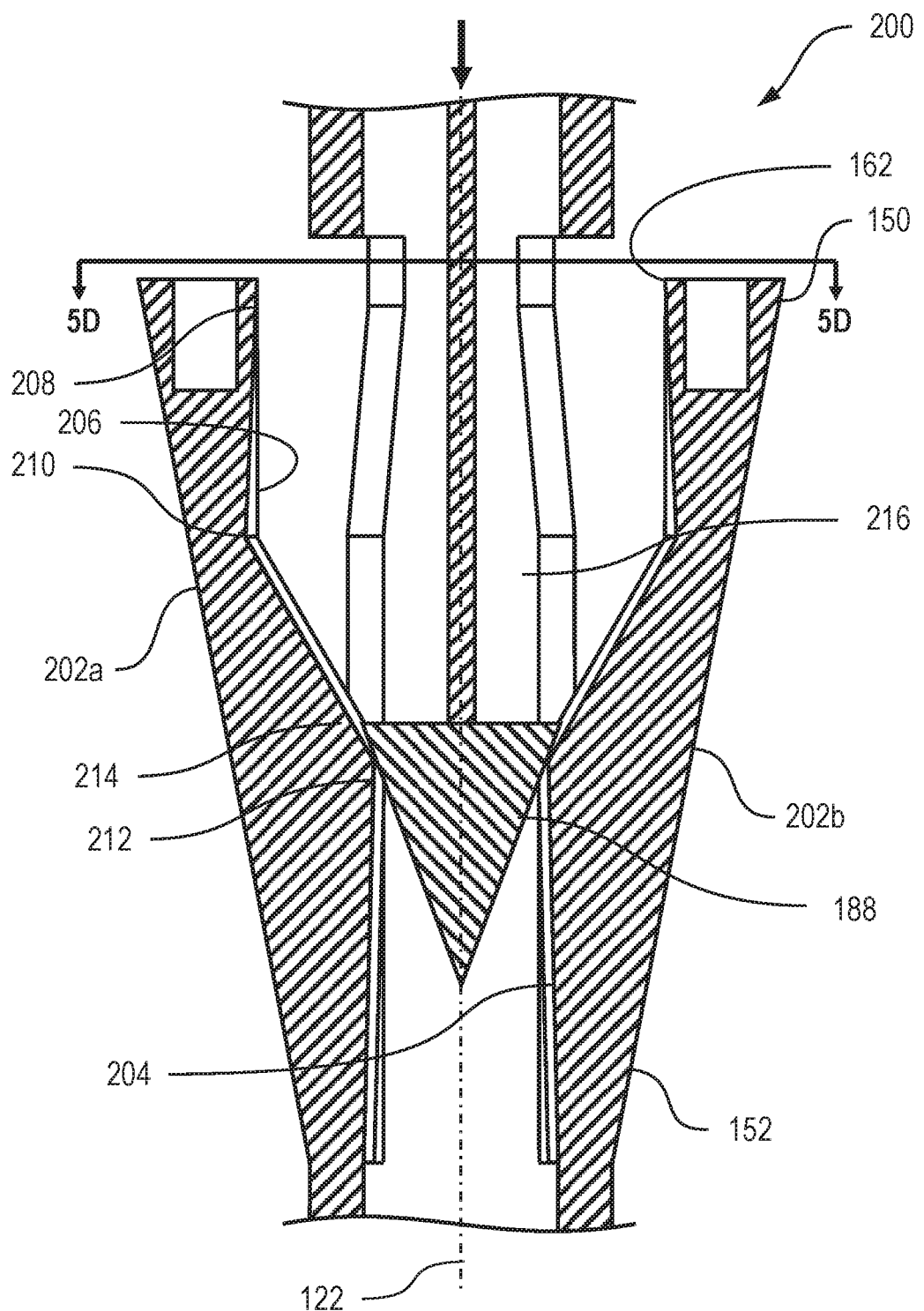
Figure 5D:
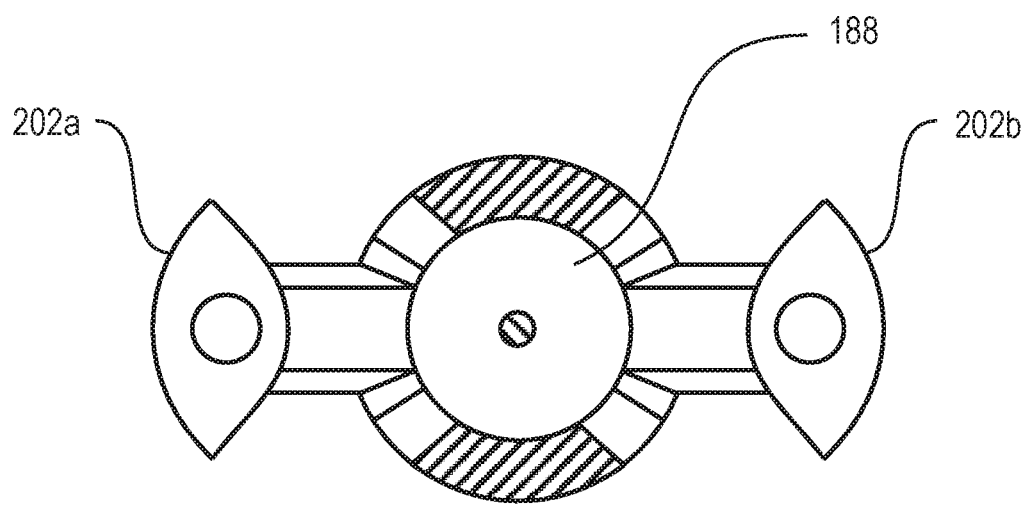

Similar to the embodiment described above, as expander 188 moves distally, the outer surface thereof can contact and move inner edges 212 laterally outward, thereby causing proximal ends 150 of arms to pivot radially outward about distal ends 152 until arms 202 are fully deployed, as shown in FIGS. 5C and 5D. Because inner edges 212 of inner surface 204 are positioned distally of proximal end 150, and because arms 202 are substantially longer than arms 120, proximal ends 150 of arms 202 are moved substantially further radially outward when deployed than are arms 120 (compare FIGS. 5C and 5D to FIGS. 3C and 3D).

Similar to the embodiment discussed above, expander 188 can be substantially conically shaped. Alternatively, expander 188 can be substantially cylindrically or rectangularly shaped as long as cavity 216 is generally shaped to receive expander therein. Other expander shapes may also be possible.

Figure 6C:
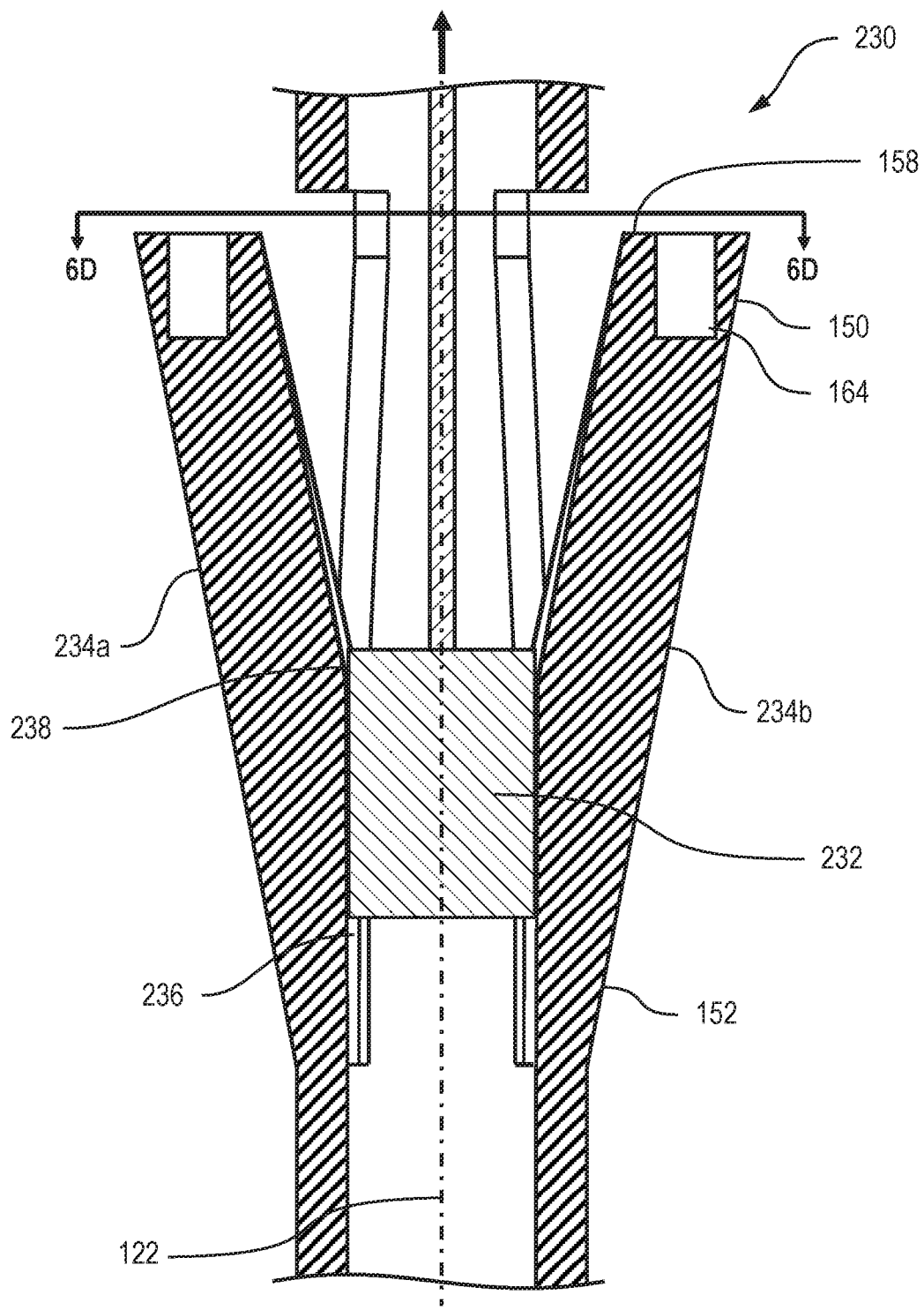

FIGS. 6A-6D show an alternative embodiment of a tissue locater 230 that uses an expander 232 that is moved proximally instead of distally to deploy the arms. Similar to the tissue locaters discussed above, tissue locater 230 also includes arms 234a and 234b having penetrator receptacles 164 on proximal end faces 158 thereof for receiving cuffs. On arms 234, a lower portion 236 of each inner surface 238 extends inward toward axis 122 as inner surface 238 extends proximally from distal end 152 of arm 234, so as to generally form a ramp, as shown in FIG. 6A.

Figure 6D:
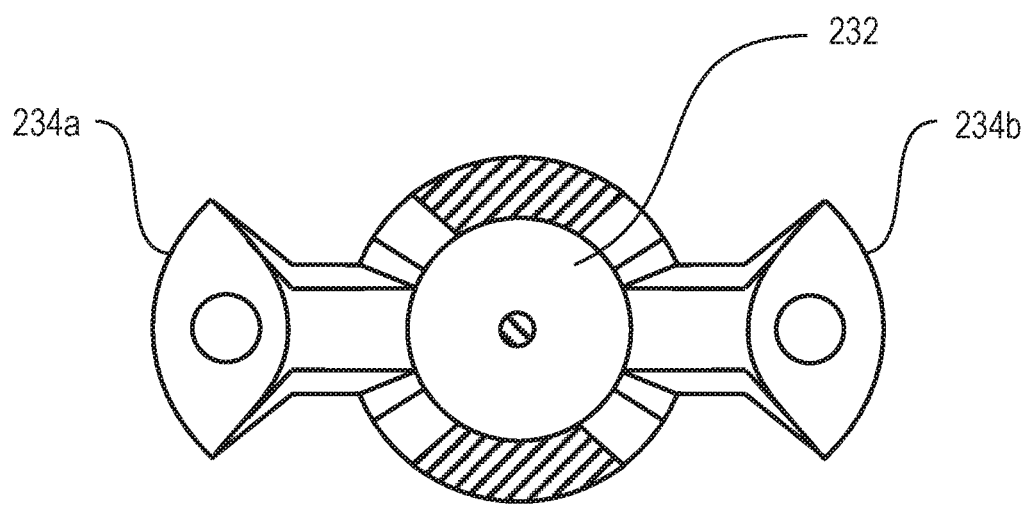

Unlike the expanders discussed above, expander 232 can be initially positioned distal of the distal end 152 of arms 234 when arms are in the retracted position, as shown in FIG. 6A. As expander 232 is withdrawn proximally, the outer surface thereof can contact the bottom portion of ramp 236 of each arm 234. As expander 232 is withdrawn further proximally, expander 232 begins to exert an outward force on arms 234 at ramps 236. As expander 232 is withdrawn further proximally, the outward force exerted by expander 232 on ramps 236 causes proximal ends 150 of arms 234 to pivot outward about distal end 152 until arms 234 are fully deployed, as shown in FIGS. 6C and 6D. As such, although various components of tissue locator 230 may be different than tissue locators 118 and 200, discussed above, the result is the same; proximal ends 150 of arms are caused to move from the retracted position to the deployed position by actuation of the actuator.

Expander 232 is shown in the depicted embodiment as being substantially cylindrical. However, similar to the expanders discussed above, expander 232 can be substantially conical or rectangular if arms are modified accordingly. Other expander shapes may also be possible.

Figure 7A:
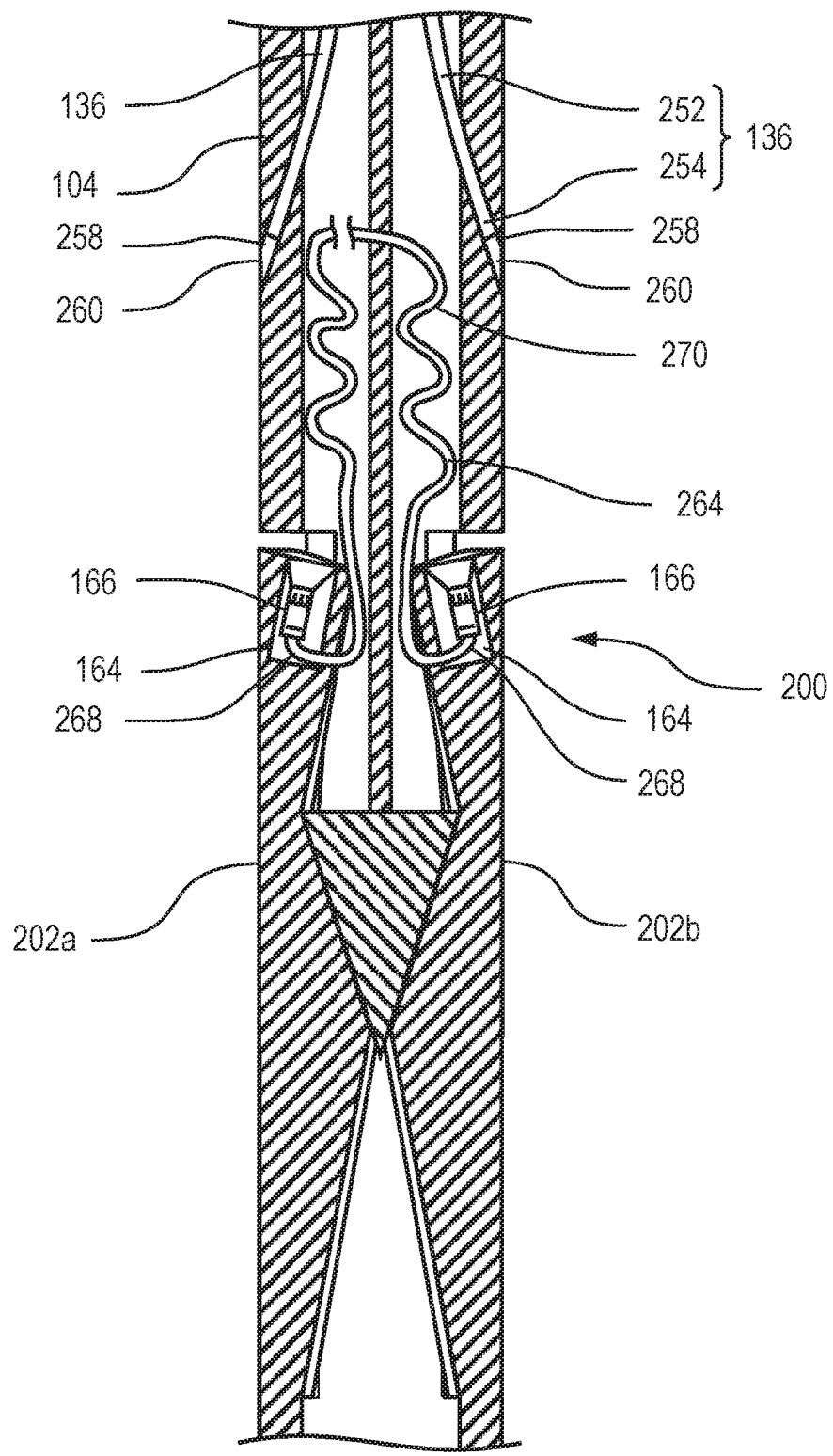
FIGS. 7A-7C are cross-sectional side views showing the needles before and after engagement with the suture cuffs in the retracted and deployed arms.
Figure 7B:
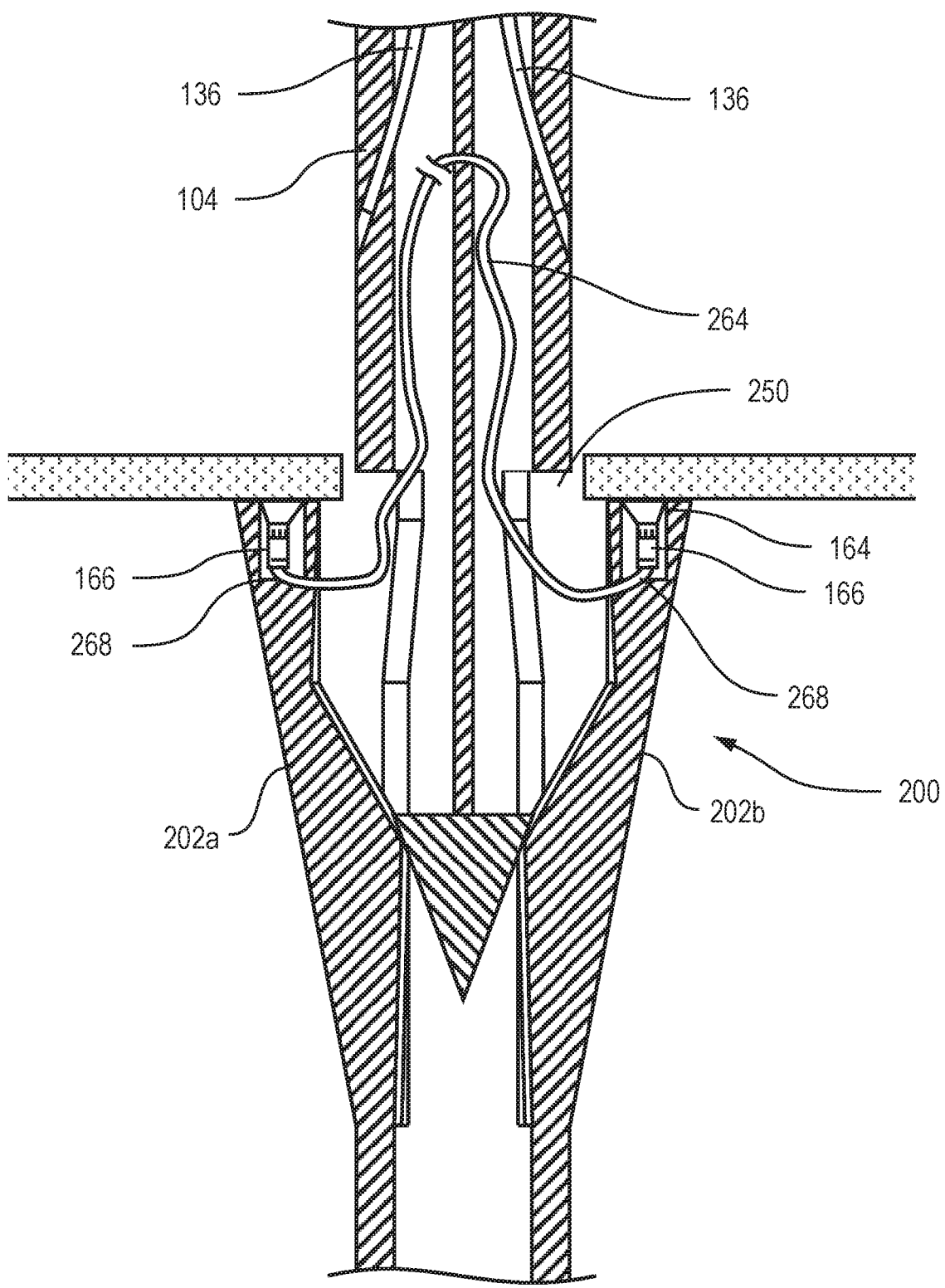
Figure 7C:
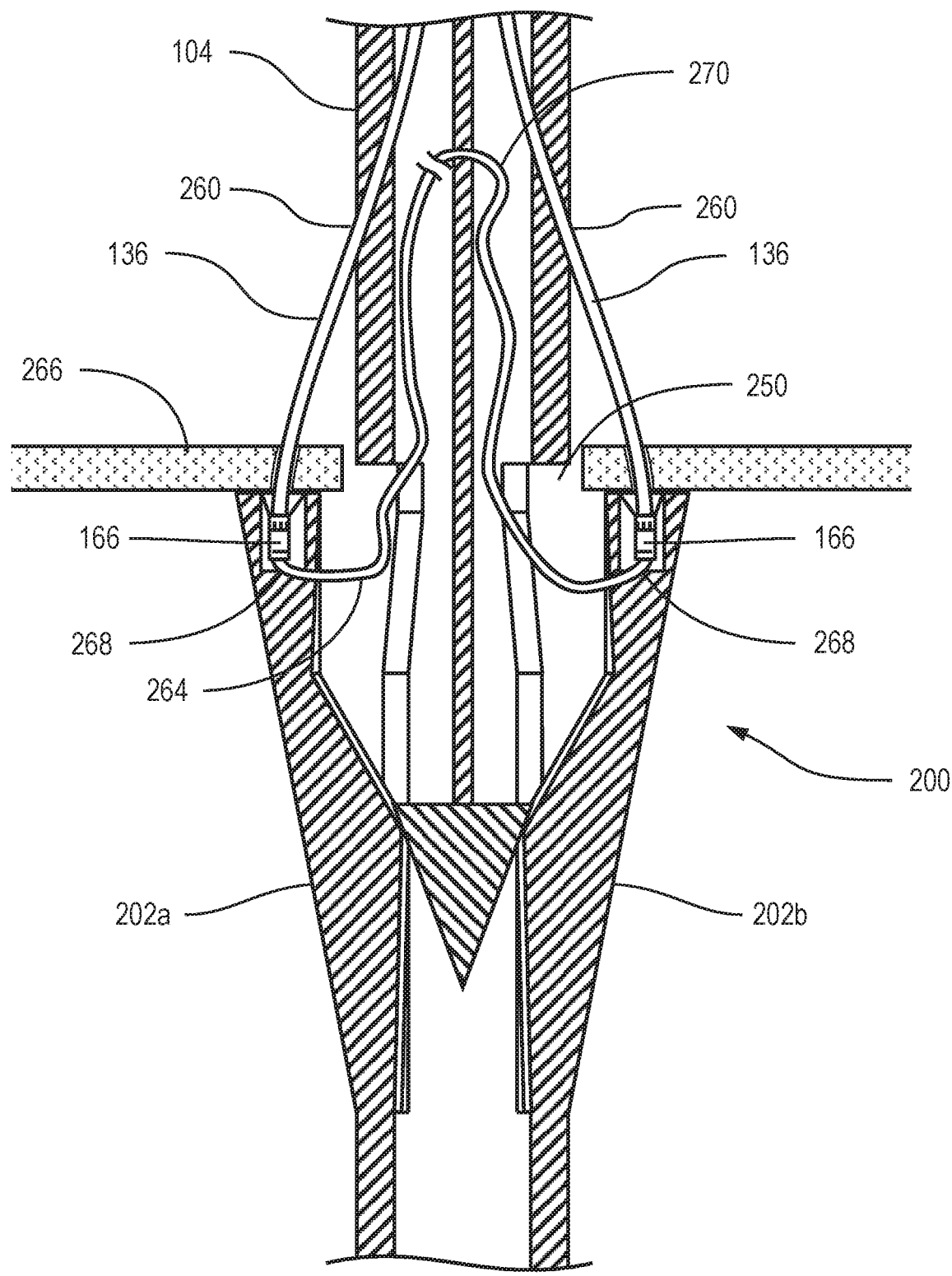

Turning to FIGS. 7A-7C, which shows tissue locator 200, cuffs 166 can be used in conjunction with penetrators 136 to help position a loop of suture or other filament 264 across a tissue opening 250 to aid in closing the opening. Each penetrator 136 can comprise a substantially rigid elongated shank 252 that extends to a distal tip 254. Penetrator 136 can also include means for attaching the penetrator to the cuff. The means for attaching can provide a permanent attachment or a removable attachment, as discussed in more detail below. In the depicted embodiment, penetrator 136 comprises an elongated needle and the means for attaching the penetrator to cuff 166 comprises a barbed tip 256 (FIG. 8) that provides a permanent attachment to cuff 166. Penetrators 136 can be initially positioned within channels or lumens 258 defined in shaft 104 to carry the penetrators, as shown in FIG. 7A. Likewise, arms 202 (202a and 202b) can be initially positioned in the retracted position, as shown in FIG. 7A. Before using penetrators 136, arms 202 should be moved to the deployed position shown in FIG. 7B. This can be done by manipulating arm actuation handle 110, as discussed above.

As shown in FIG. 7A, penetrator guides 260 can be positioned at the distal end of lumens 258 to laterally deflect penetrators 136 outward as penetrators 136 are moved distally so penetrators 136 can extend laterally to cuffs 166 of arms 202 when arms 202 are in the deployed position. This lateral deflection of penetrators 136 can allow the use of a small diameter shaft 104, while still encompassing sufficient tissue within the suture loop on opposite sides of the tissue opening so as to effect hemostasis when the suture loop is tightened and secured.

In some embodiments, shaft 104 can comprise an outer casing of a biocompatible material such as stainless steel, carbon fiber, nylon, another suitable polymer, or the like. Penetrator guides 260 may be defined at least in part as lumens formed within the casing of a polymeric material such as nylon or the like. In some embodiments, shaft 104 may comprise a carbon-fiber filled nylon, or carbon fiber filled with an alternative material.

As shown in the depicted embodiment, an end 268 of suture loop 264 can be attached to each cuff 166. Opposite ends of the same suture can be secured to different cuffs 166, as in the depicted embodiment, or ends of different sutures can be used.

In one embodiment, suture 264 can comprise a continuous filament with one end 268 of the suture being attached to cuff 166 in penetrator receptacle 164 of one arm 202a and the other end 268 of the suture being attached to cuff 166 in penetrator receptacle 164 of the opposite arm 202b. An intermediate portion 270 of suture 264 between the ends 268 may extend proximally into shaft 104. In one embodiment, intermediate portion 270 can extend along a suture lumen of shaft 104 to proximal housing 102 or beyond. Alternatively, the intermediate portion 270 of suture 264 between the ends 268 may extend distally within guide body 116 or may be positioned external to shaft 104. In still further alternatives described below, a short length of suture or some other flexible filament 264 may extend substantially directly between the penetrator receptacles in the two arms.

To use penetrators 136 to help close tissue opening 250, arms 202 of tissue closure device 200 should be positioned through opening 250 and then moved to the deployed position shown in FIG. 7B. This can be done by manipulating arm actuation handle 110, as discussed above. As arms 202 are moved to the deployed position, ends 268 of suture 264 also move outward due to the attachment of suture 264 to each cuff 166.

Upon actuation of penetrator actuation handle 106 (see FIGS. 1 and 2), penetrators 136 move distally and extend laterally from shaft 104 to securely engage with cuffs 166, as shown in FIG. 7C. Specifically, penetrators 136 advance from fixed penetrator guides 260, and are laterally directed into cuffs 166 by receptacles 164.

Figure 8:
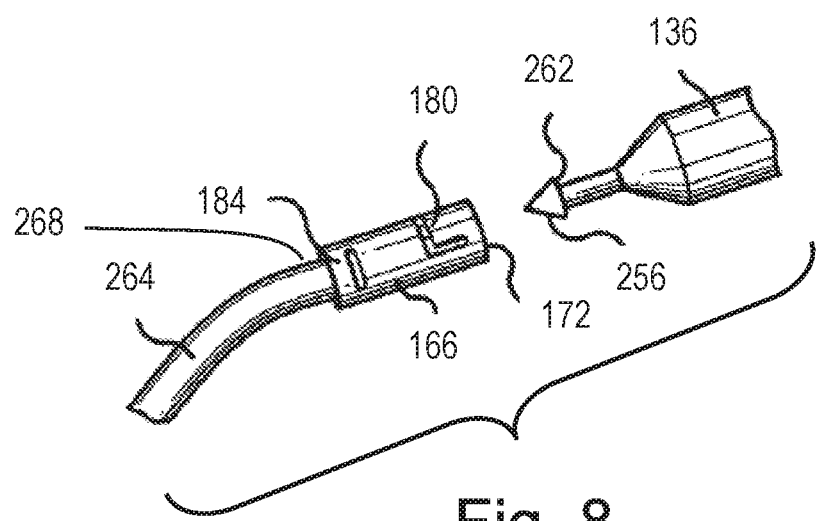
FIG. 8 is a perspective view illustrating a suture attachment cuff and an associated barbed needle.

In one embodiment, penetrator 136 comprises an elongated needle having a barbed end 256 defining a recessed engagement surface 262, as shown in FIG. 8. Channel 172 of cuff 166 can receive barbed end 256 of needle 136 therein. Tabs 180 can be resiliently biased inward into channel 172. As needle 136 advances into cuff 166, barbed end 256 resiliently displaces tab 180 clear of channel 172 so as to allow the barbed end to pass axially into cuff 166. Once barbed end 256 is disposed axially beyond tab 180, tab 180 can resiliently flex back into channel 172, thereby capturing needle 136 by engagement between tab 180 and recessed surface 262. As each tab 180 can hold cuff 166 in place on needle 136, the use of more than one tab can increase the reliability of the system. For example, three tabs 180 can be provided on cuff 166, as illustrated in FIG. 4. Once needle 136 has been secured to cuff 166, the cuff can be withdrawn proximally from arm 234 by withdrawing needle 136 proximally back toward shaft 104. Other types of penetrators besides needles can also be used with cuff 166, as discussed below.

Returning to FIG. 7C in conjunction with FIG. 8, each cuff 166 can be generally configured to facilitate withdrawal of itself (and any attached suture or filament 264) along with penetrator 136 axially through the tissue wall 266 along the penetrator path. As such, penetrator 136 can comprise an elongated shank having a cross-sectional width of between about 0.010 inches and about 0.020 inches, with other widths being possible. Engagement surface 262 formed by barb 256 can have a protruding length of between about 0.002 inches and about 0.005 inches, with other lengths being possible.

As shown in FIG. 8, cuff 166 can have a cross-sectional size roughly corresponding to or slightly larger or smaller than penetrator 136. In one embodiment, cuff 166 can have an outer lateral width of between about 0.014 inches and 0.025 inches, and an axial length of between about 0.035 inches and 0.050 inches. Channel 172 can be sized to receive at least a portion of needle 136, and can generally have a width of between about 0.010 inches and 0.020 inches, with other widths also being possible. In the exemplary embodiment, penetrator 136 has a diameter of about 0.020 inches, while the cuff comprises a tube having an outer diameter of about 0.020 inches, an inner diameter of about 0.016 inches, and an overall length of about 0.047 inches. In some embodiments, the diameter of cuff 166 is based primarily on the diameter of suture 264 attached thereto. Weeping of blood can occur through the tissue hole created by penetrator 136 if the hole is substantially larger than the suture. As such, greater diameters can be used for cuff 166 and penetrator 136 if a suture of a correspondingly greater diameter is used.

Penetrator 136 can have a length of between about 5.0 inches and 6.0 inches, with other lengths also possible. Penetrator 136 can be sufficiently stiff to be advanced in compression through the tissue wall (and adjacent tissues, if necessary) for up to about 0.5 inches when supported in cantilever. Greater distances may also be possible. Penetrator 136 can also be substantially flexible to be laterally deflected within shaft 104 by penetrator guide 260, as discussed above. Penetrator 136 can be comprised of a high strength metal, such as, e.g., stainless steel. Other materials can also be used.

Cuff 166 can also comprise a flexible material to allow tab 180 to flex out of the way of barbed end 256, and to resiliently rebound and engage recessed surface 262, as discussed above. In one embodiment, barbed end 256 can have a diameter of about 0.015 inches, with the diameter of the penetrator decreasing to about 0.008 inches proximally of the barb so as to define recessed engagement surface 262.

As noted above, an end 268 of suture or other filament 264 can be attached to each cuff 166. In the embodiment depicted in FIG. 8, the end 268 of suture 264 is secured to the distal end of cuff 166 using suture collar 184. Collar 184 may be crimped about suture 264 to mechanically affix the suture to cuff 166. In addition and/or instead of mechanical crimping, the end of the suture may be bonded to cuff 166 using an adhesive, heat, fasteners, knots, or the like. In one embodiment, one or both ends of the suture is enlarged to prevent the end from passing completely through the cuff. Other types of securing devices or methods can also be used. Opposite ends of the same suture can be secured to different cuffs 166, as in the embodiment depicted in FIGS. 7A-7C, or ends of different sutures can be used.

By being secured to cuff 166, the end 268 of suture 264 can also be withdrawn proximally from arm 202 when the cuff is withdrawn proximally by penetrator 136. As such, as cuffs 166 and associated portions of suture 264 are releasably supported in arms 202, needles 136 can be withdrawn proximally so as to draw cuffs 166 and attached suture ends 268 from arms 202 proximally into shaft 104. By extending axially from cuff 166 opposite the open end of channel 172, drag may be minimized when the suture is drawn proximally along the penetrator path.

Figure 9:
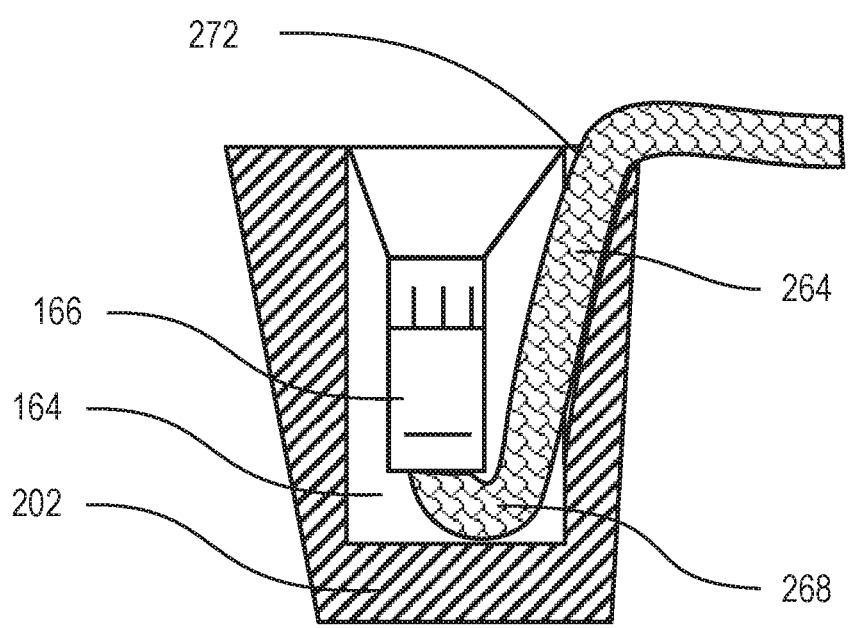
FIG. 9 illustrates a suture cuff and attached suture positioned within a penetrator receptacle.

As discussed above, cuffs 166 and suture 264 can be withdrawn proximally from penetrator receptacles 164 by penetrators 136. Turning now to FIG. 9, to avoid entanglement of suture 264 with penetrators 136, a slot 272 can be formed in each arm 202 so as to extend laterally and proximally from penetrator receptacle 164. Slot 272 can be sized to receive suture 264 as suture 264 extends from cuff 166. As penetrators 136 pull cuffs 166 axially from penetrator receptacles 164, suture 264 can be pulled from slots 272 and free from arms 202. Bending of suture 264 within suture slot 272 can also help hold cuff 166 in penetrator receptacle 164. If desired, slot 272 can be sized to have a smaller cross-section than barbed tip 256 so that the barbed tip is unable to enter slot 272, thereby avoiding entanglement between penetrator 164 and suture 264.

Figure 10A:
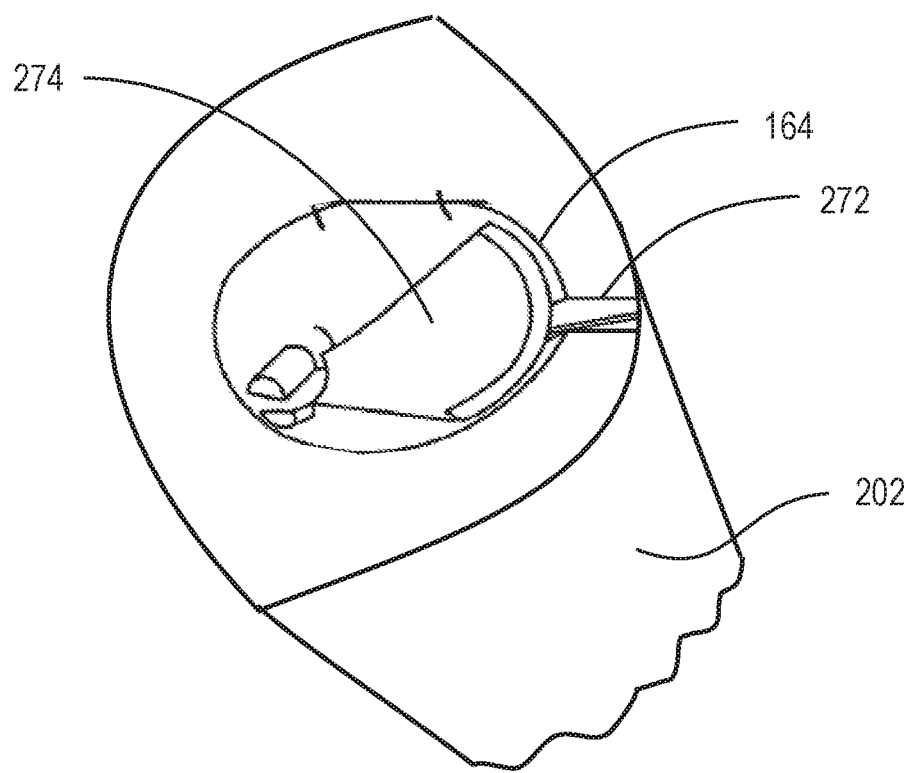
FIGS. 10A-10C illustrate alternative structures and techniques for avoiding entanglement of the needle with the suture.

A variety of other features may be included in the arms, penetrator receptacles, and/or penetrators to avoid tangling of the penetrators in the suture as the penetrators are directed to the cuff. For example, as illustrated in FIG. 10A, a moveable flap 274 may extend over slot 272 so that the advancing penetrator can slide along flap 274 toward the cuff, rather than entering slot 272 and engaging suture 264 directly. Flap 274 may be affixed along one side of slot 272, with the other side of flap 274 flexing into receptacle 164 to release suture 264 from slot 272 when the cuff and suture 264 are withdrawn by the penetrator.

In an alternative mechanism for avoiding entanglement of the penetrator with the suture, slots 272 of penetrator receptacles 164 can extend substantially tangentially to the surface of the receptacle. As a result of this tangential arrangement, a penetrator entering receptacle 164 can be directed toward cuff 166 contained therein, but does not enter and advance within the tangential slot 272 so as to become entangled with the suture. Slots 272 may optionally extend laterally through the arm so that the loop of suture can be pulled from one side of the shaft 104 without interference.

Figure 10B:
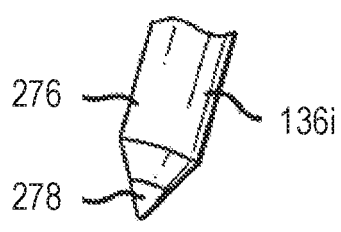
Figure 10C:
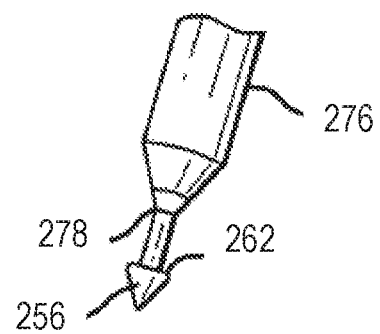

Another alternative mechanism for avoiding entanglement between the suture and the penetrator is illustrated in FIGS. 10B and 10C. A two-part penetrator 136i can include an outer sheath 276 and an inner core 278. These parts of the penetrators can initially advance together into the receptacles with penetrator core 278 retracted so that the penetrator presents a smooth tapered tip, as illustrated in FIG. 10B. If desired, the combined tip can be larger in diameter than the slot containing the suture. Once two-part penetrator 136i is fully positioned within the penetrator receptacle, penetrator core 278 may be extended axially to expose barbed tip 256 and recessed engagement surface 262, as shown in FIG. 10C, and to secure the penetrator to the cuff within the penetrator receptacle.

A first method of using a tissue closure device having a tissue locator to close an opening in tissue will now be explained with reference to FIGS. 11A-11G. For purposes of discussion, the method will be set forth with reference to tissue locator 200. However, it is appreciated that the other tissue locators discussed or envisioned herein can alternatively be used in this or any of the methods presented herein. Initially, arms 202 are in the retracted position with cuffs 166 being positioned within penetrator receptacles 164, and penetrators 136 are withdrawn within shaft 104 proximal of arms 202, as shown in FIG. 7A. A length of suture 264 is provided with ends 268 of suture 264 attached to each cuff 166 and the intermediate section 270 of suture 264 extending into shaft 104 proximal of arms 120. Alternatively, intermediate section of suture can extend into shaft 104 or guide body 116 distal of arms 120, or can be positioned external to shaft 104, as discussed above.

Figure 11A:
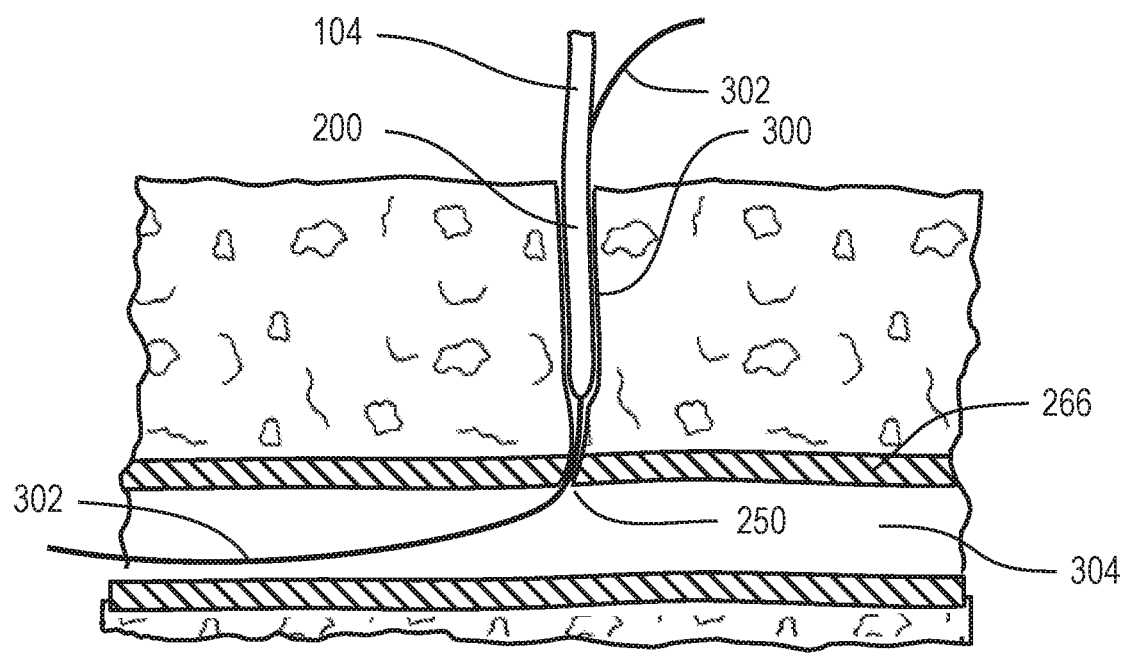
FIGS. 11A-G illustrate a method of using a tissue closure device having the tissue locator shown in FIGS. 5A-5D.
Figure 11B:
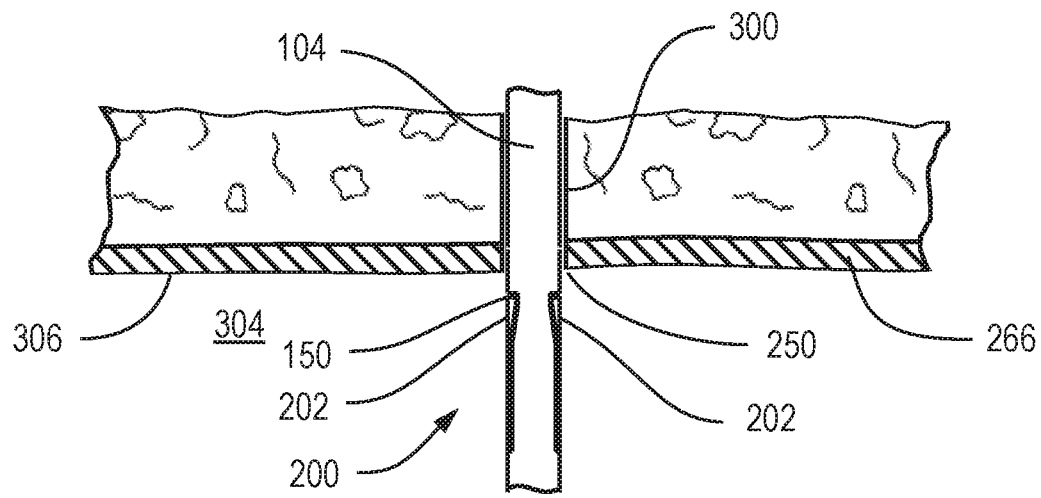

Tissue locator 200 can be used to help close an opening in tissue, such as an incision in a blood vessel. To do so, the distal end of shaft 104 is advanced distally through a tissue tract 300 and through the opening 250 in the vessel wall 266 while the arms are in the retracted position, as shown in FIG. 11A. This can be done in a number of ways. For example, after an endovascular procedure, a guide wire 302 and a guide body that have been positioned through the opening 250 in vessel wall 266 can be used. Shaft 104 is advanced until tissue locator 200 has advanced through opening 250 and into the blood vessel 304 far enough that the proximal ends 150 of arms 202 are positioned distal of vessel wall 266, as shown in FIG. 11B. Shaft 104 can include a bleed-back lumen, as is known in the art, to notify the operator that arms 202 have been advanced far enough for deployment.

Figure 11C:
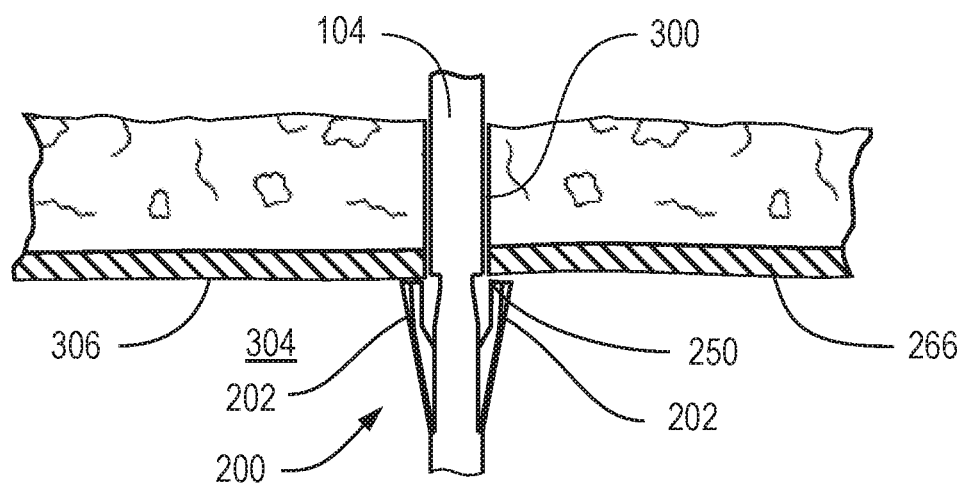

Once arms 202 are positioned within the vessel lumen 304 (i.e., distal of vessel wall 266), arms 202 can be deployed and used to "locate" the inner surface 306 of vessel wall 266 surrounding opening 250. To do so, the expander is moved to contact and produce a laterally outward force on arms 202 by actuation of the arm actuation handle, as discussed above. This causes the proximal ends of arms 202 to rotate radially outward to the deployed position in the manner discussed above, on the distal side of the vessel wall 266, as shown in FIG. 11C. Using tissue locator 200, the expander is moved distally when actuated, as discussed above. It is appreciated that with other embodiments of tissue locators, the expander may instead be moved proximally to provide the laterally outward force for moving the arms to the deployed configuration, as discussed above.

Once arms 202 have been fully deployed, shaft 104 can be gently pulled proximally until the penetrator receptacles 164 formed on arm faces 158 are drawn proximally against the inner surface 306 of vessel wall 266 on opposite sides of opening 250, as shown in FIG. 11C. See also FIG. 7B. Not only do arms 202 help to accurately position the penetrator receptacles on the distal surface 306 of the tissue wall 266, they also help to position the penetrator guides at a predetermined proximal distance from the tissue.

Figure 11D:
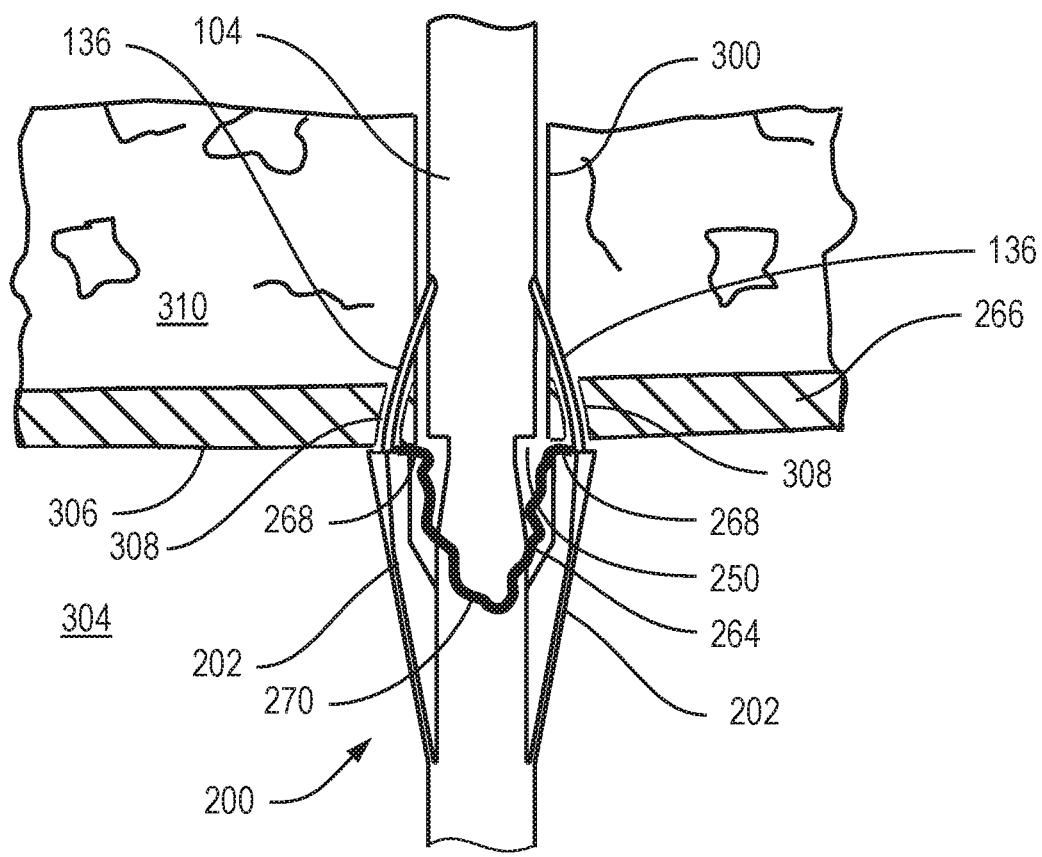

Once the arm faces are drawn proximally against the inner surface 306 of vessel wall 266, penetrators 136 can be extended to arms 202, as shown in FIG. 11D. To do this, penetrators 136 are advanced distally and laterally from channels or lumens in shaft 104 through penetrator guides by actuation of the penetrator actuation handle, as discussed above.

The distal tips of penetrators 136 form penetration paths 308 in vessel wall 266 on opposite sides of opening 250 as penetrators 136 advance distally therethrough. As the distal ends of penetrators 136 advance to arms 202, the tapering surfaces of the receptacles help to push penetrators 136 into alignment with the cuffs in arms 202 so as to overcome any unintended deflection of penetrators 136 by surrounding tissue 310 or vessel wall 266. This ensures that the means for attaching each penetrator 136 to the corresponding cuff engages the cuff within each receptacle, as discussed above, thereby coupling the ends 268 of suture 264 to the penetrators. In the present method, the means for attaching the penetrator to the cuff comprises the barbed tip to provide a permanent attachment between the penetrator and the cuff.

As discussed above, the middle portion 270 of suture 264 can be positioned within a shaft 104 proximal of arms 202. Alternatively, the suture loop can instead extend distally from arms in a lumen of shaft 104 or guide body, can be routed through the arms, and/or can be positioned external to the shaft and guide body. Other suture paths can also be used. Regardless, suture 264 should be configured to pull free of the tissue closure device between the ends of the suture to form a continuous loop across opening 250. The amount of suture 264 between arms 202 can vary.

Figure 11E:
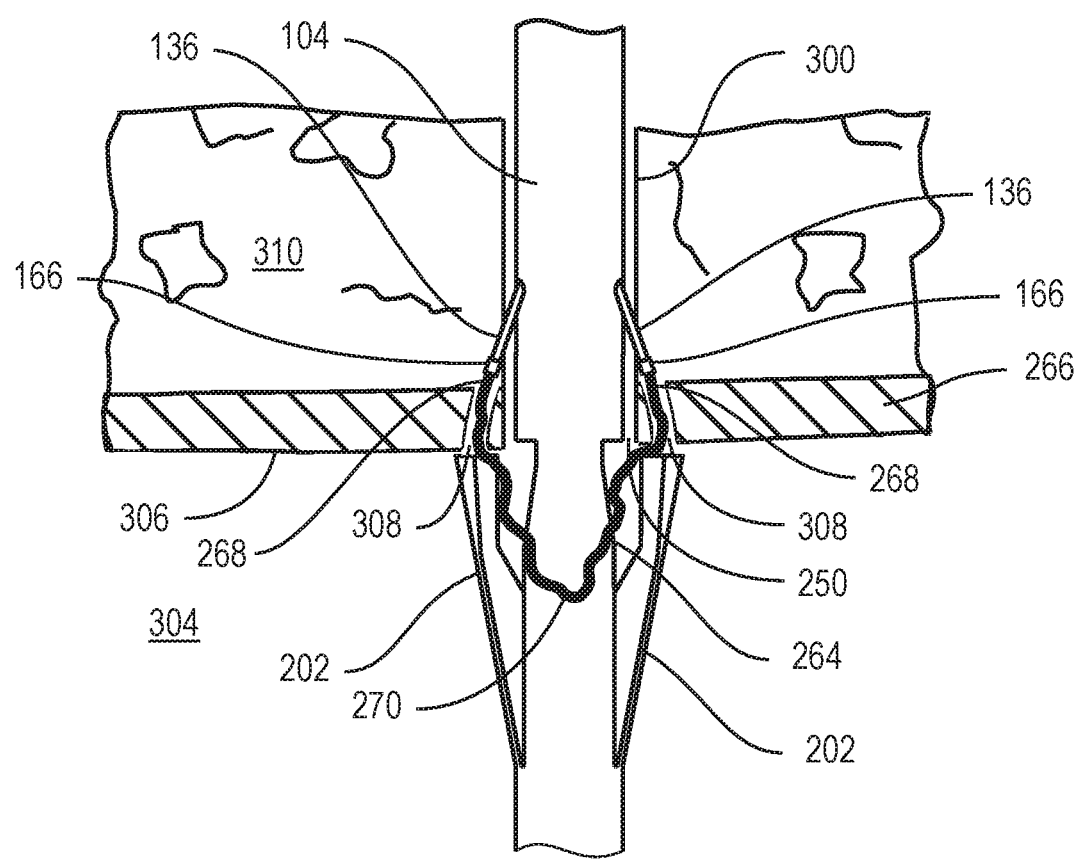
Figure 11F:
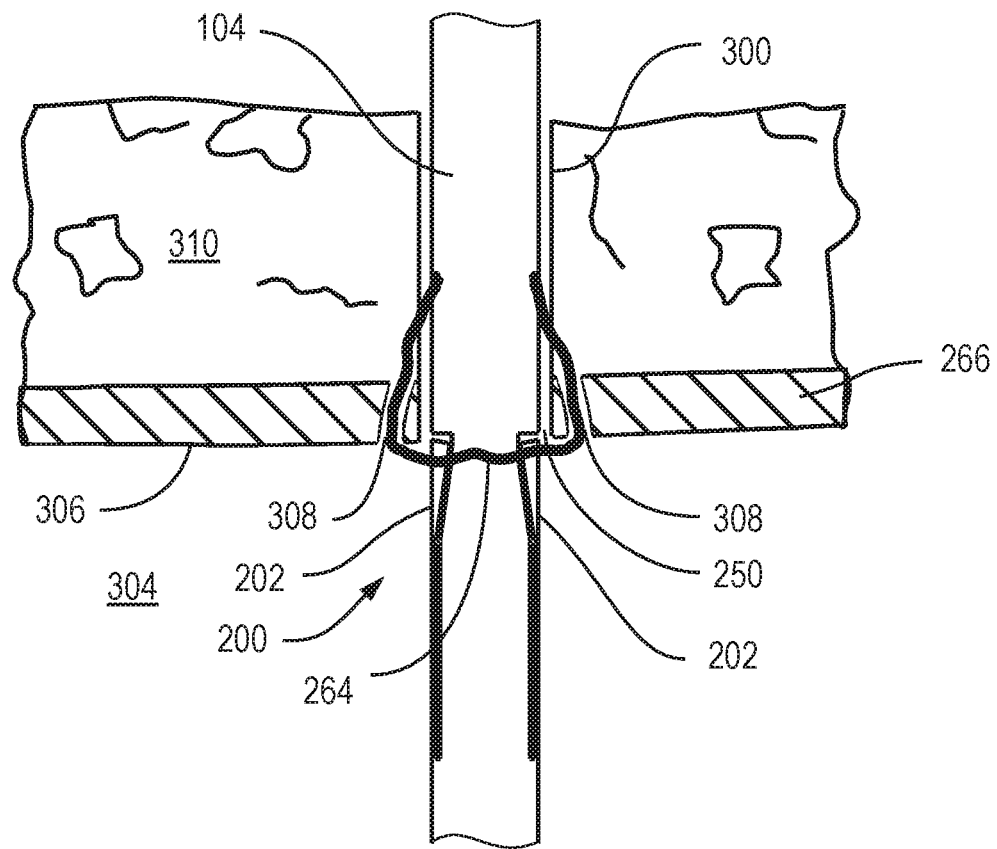

Penetrators 136 can then be used to pull suture 264 proximally through vessel wall 266, as shown in FIG. 11E. To do so, penetrators 136 are withdrawn proximally through penetration paths 308 in vessel wall 266 by moving penetrator actuation handle 106. Due to the secure engagement of penetrators 136 and suture 264 to cuffs 166, the withdrawal of penetrators 136 causes cuffs 166 and the ends 268 of suture 264 to also be drawn proximally through vessel wall 266 along penetrator paths 308 formed by penetrators 136. As ends 268 of suture 264 move proximally through vessel wall 266, a portion of the intermediate section 270 attached to ends 268 is also pulled proximally through penetrator paths 308.

After the ends 268 of suture 264 have been withdrawn proximally through vessel wall 266 and into shaft 104 by penetrators 136, tissue locator 200 can be removed. To do so, arms 202 are moved back to the retracted position shown in FIG. 11F by moving the expander using arm actuation handle 110. This causes the expander to no longer produce a lateral outward force on arms 202, which allows the proximal ends of arms 202 to rotate inward to the retracted position. If needed, tissue closure device 200 can be moved slightly distally away from inner surface 306 of vessel wall 266 before retraction of arms 202 so the arms can move to the retracted position more easily. Using tissue locator 200, the expander is moved proximally to allow arms 202 to rotate back to the retracted position. It is appreciated that with other embodiments of tissue locators, the expander may instead be moved distally to allow the arms to rotate back to the retracted position, as discussed above.

With arms 202 in the retracted position, shaft 104 can be withdrawn proximally through tissue tract 300 and removed therefrom. This causes tissue locator 200 to also move proximally back through opening 250 to be withdrawn from tissue tract 300. The withdrawal of tissue closure device 200 also causes the ends 268 of the suture loop 264, which are still secured to needles 136, to continue to be proximally withdrawn. As the suture ends 268 are withdrawn, more of the intermediate section 270 of the suture 264 is pulled proximally through penetrator paths 308 on both sides of opening 250. If any of the intermediate portion 270 of suture 264 is originally positioned proximal of vessel wall 266, that portion passes distally through opening 250 before being pulled back proximally through penetrator paths 308 in vessel wall 266.

Figure 11G:
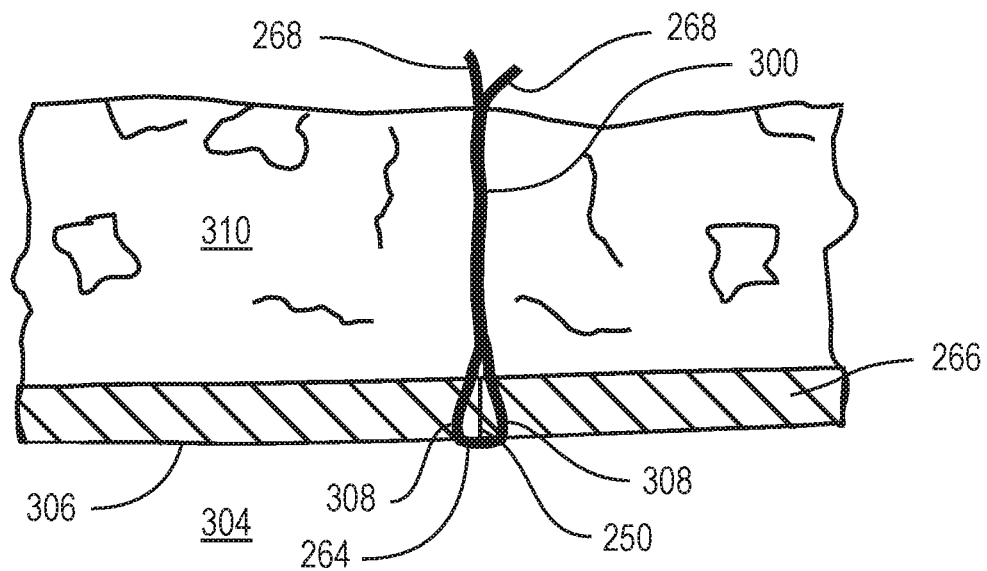

Once shaft 104 has been withdrawn sufficiently, suture 264 can be used to close opening 250. To do so, ends 268 of the suture 264 can be grasped by the operator and pulled proximally to pull the remaining suture loop 264 proximally through penetrator paths 308 on the opposite sides of opening 250 to close the opening, as shown in FIG. 11G. A knot or closure device can then be used to secure suture 264 to allow the closure of opening 250 to become permanent, as is known in the art.

FIGS. 12A-12D show an alternative, second, method of using tissue locator 200 to close the tissue opening. In the alternative method, rather than pulling the two opposite ends of an extended loop through the needle paths and proximally out the tissue tract for tying, tissue closure device 200 advances a single end of suture distally along one needle path, across the opening, and then proximally out along the other needle path.

Figure 12A:
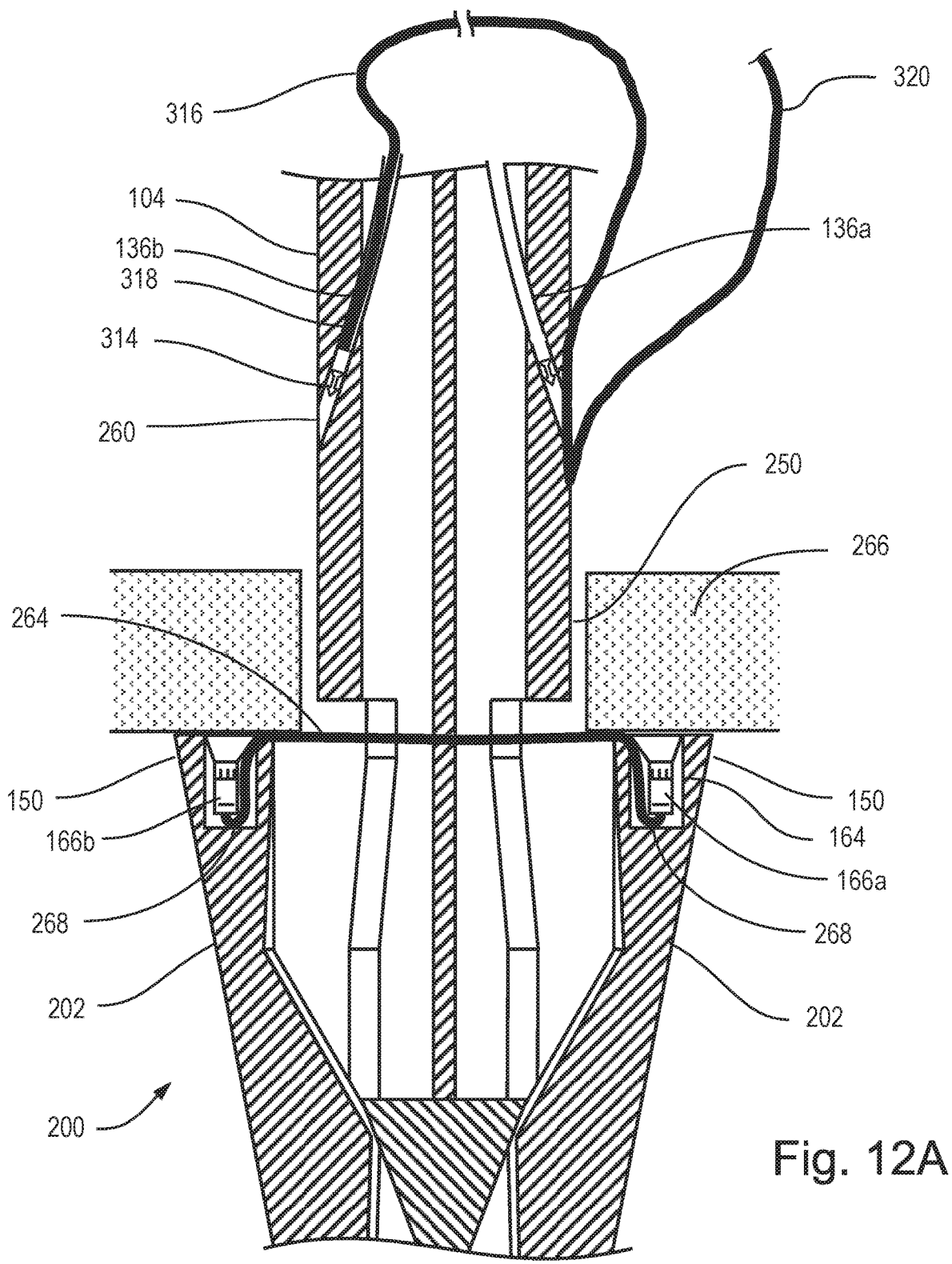
FIGS. 12A-D illustrate an alternative method of using a tissue closure device having the tissue locator shown in FIGS. 5A-5D.

Similar to the first method, shaft 104 is advanced through opening 250 until the proximal ends 150 of arms 202 are positioned distal of the vessel wall 266, whereupon arms 202 are deployed and moved into contact with the inner, or distal, surface 306 of vessel wall 266 surrounding opening 250, as shown in FIG. 12A. Also similar to the first method, each penetrator receptacle 164 contains a cuff 166 having attached thereto an end 268 of suture or filament 264. However, instead of two ends of a long suture being attached to the cuffs, suture or connecting filament 264 is short and spans substantially directly between penetrator receptacles 164 to attach to cuffs 166, as shown in schematic in FIG. 12A. As such, connecting suture or filament 164 forms a link between cuffs 166.

Similar to the first method, each penetrator 136 includes means for attaching the penetrator to the cuff. However, while one of the penetrators includes a means for attaching that is permanent (e.g., the barbed tip), the other penetrator includes a means for attaching that is releasable. For ease of description, the penetrator having the means for permanent attachment will be referred to as the "first" penetrator and the penetrator having the means for releasable attachment will be identified as the "second" penetrator herein and the identifiers thereof will be respectively differentiated with an "a" and a "b" appended to the identifier. Thus, the first penetrator and second penetrators 136 will be respectively identified as 136a and 136b. The cuffs, penetrator receptacles, penetrator paths, etc. associated with each penetrator will likewise be referred to as "first" and "second" cuffs, penetrator receptacles, penetrator paths, etc and be differentiated in the same manner (i.e., with an "a" or "b" appended to the identifier) as the penetrators.

To facilitate separation of the second penetrator 136b from the second cuff 166b, second penetrator 136b includes a detachable coupling structure that allows penetrator 136b to separate from the second cuff 166b when the penetrator is withdrawn therefrom. For example, in the depicted embodiment, the distal end of second penetrator 136b comprises a detachable tip 314.

A suture loop 316 having two ends 318 and 320 is positioned within or proximal of shaft 104, as shown in schematic. The first end 318 of suture 316 is releasably attached to second penetrator 136b using the detachable coupling structure so that suture 316 can separate from second penetrator 136b when second penetrator 136b is withdrawn from second cuff 166b. For example, in the depicted embodiment, the first end 318 of suture 316 is attached to detachable tip 314. Second penetrator 136b may be hollow so that suture 316 may extend proximally within the hollow penetrator where the penetrator has an open channel along its length, may exit the hollow penetrator just proximally of detachable tip 314, or may be disposed alongside a solid penetrator.

Figure 12B:
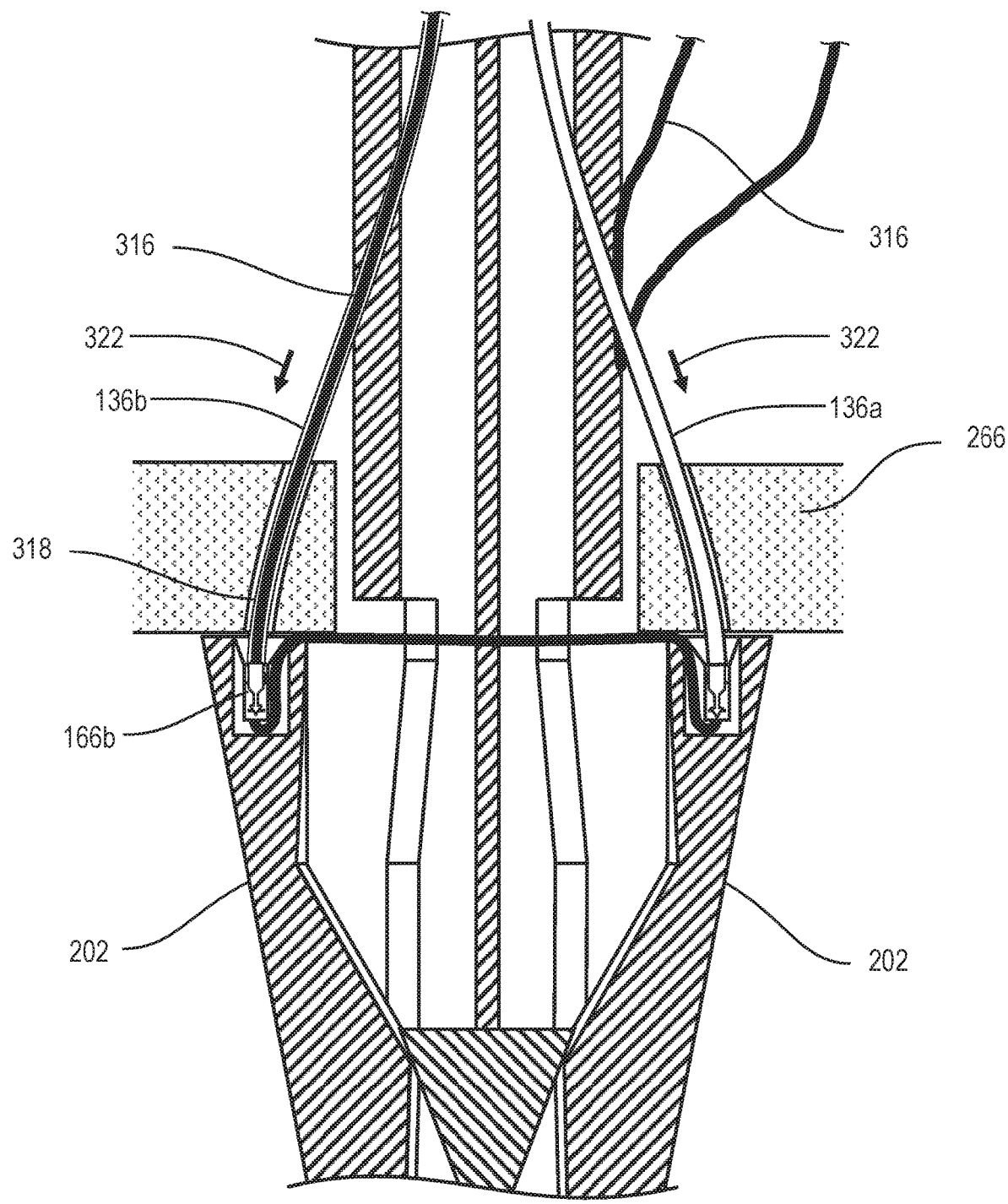

Similar to the first method, both penetrators 136 are advanced distally through tissue wall 266 to become attached to cuffs 166, as shown by arrows 322 in FIG. 12B. Because of its attachment to second penetrator 136b, the first end 318 of suture 316 is also advanced proximally through tissue wall 266 and secured to second cuff 166b along with second penetrator 136b.

Figure 12C:
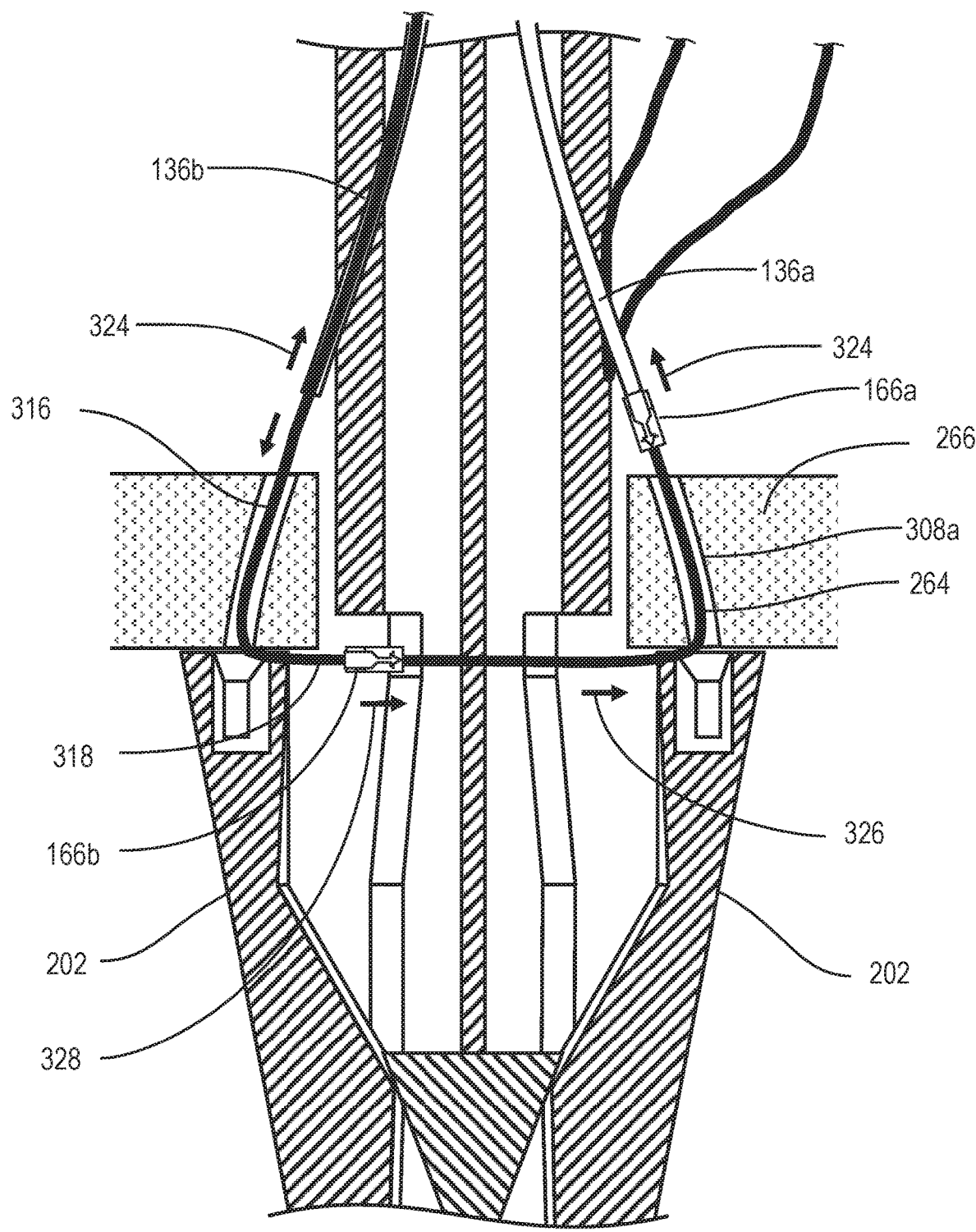

When penetrators 136a and 136b are subsequently withdrawn proximally from arms 202, as indicated by direction arrows 324 in FIG. 12C, suture 316 advanced through tissue wall 266 with second penetrator 136b remains attached to second cuff 166b with the detachable tip. First cuff 166a remains secured to first penetrator 136a, as in the first method, and is withdrawn proximally therewith. As link 264 extends between cuffs 166a and 166b, and as detachable tip 314 can pull free of second penetrator 136b when the penetrators are withdrawn, this effectively couples first penetrator 136a to first end 318 of suture 316.

Thus, as first cuff 166a is withdrawn proximally through first penetrator path 308a as indicated by directional arrow 324, link 264 between cuffs 166a and 166b is drawn across the tissue opening, as indicated by directional arrow 326, and also withdrawn proximally through first penetrator path 308a. Because of its attachment to link 264, second cuff 166b, along with suture 316 now attached thereto, are also drawn across the tissue opening, as indicated by directional arrow 328.

Figure 12D:
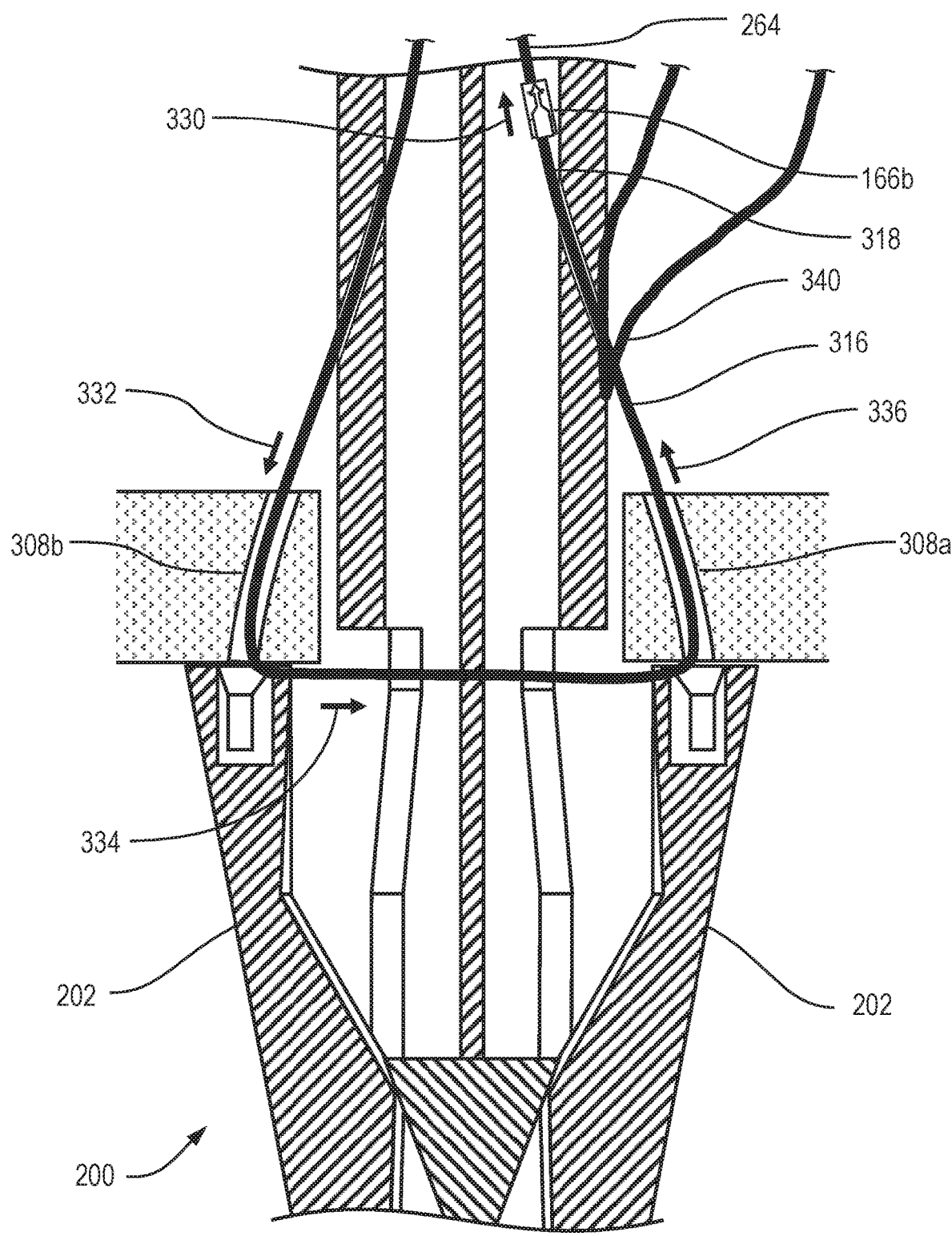

As shown in FIG. 12D, as the first and second penetrators are further withdrawn proximally, second cuff 166b is withdrawn proximally through first penetrator path 308a and out of the body, as indicated by directional arrow 330, by virtue of the attachment of second cuff 166b to link 264. As a result, suture 316, which is attached to second cuff 166b, is pulled distally through second penetration path 308b, as indicated by directional arrow 332, across the tissue opening, as indicated by directional arrow 334, and then back proximally through first penetration path 308a, as indicated by directional arrow 336.

As a result, rather than pulling both ends of an extended loop through the penetrator paths and proximally out the tissue tract for tying as is done in the first method, a single end of suture attached to the second cuff advances distally through the second penetrator path, across the tissue opening, and then proximally along the first penetrator path as the penetrators are withdrawn.

Once the first end 318 of tissue 316 has been withdrawn proximally through first penetration path 308a, arms 202 can be moved to the retracted position and tissue closure device 200 can be removed from the tissue tract. A knot or closure device can then be used to secure the suture 316 to allow the closure of the tissue opening to become permanent.

Figure 13A:
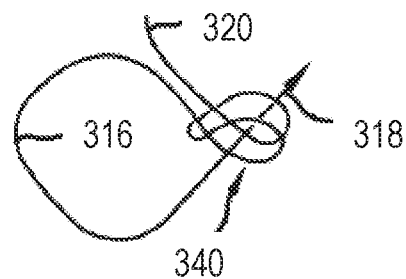
FIGS. 13A and 13B illustrate various embodiments of pre-tied knots that can be used with embodiments of the present invention.

The second method is especially useful for using a pre-tied knot to close the tissue opening. For example, turning to FIG. 13A, a bight 340 of suture 316 can be releasably attached to the shaft encircling the opening of penetrator guide 260 (see FIG. 12A) of the fixed tip penetrator. The bight 340 of suture 316 may be releasably disposed within a slot of the shaft, may be temporarily held in place by a weak adhesive or coating, or the like. The second end 320 of suture 316 can extend proximally along the shaft and can also be releasably held along the shaft, if desired.

Figure 13B:
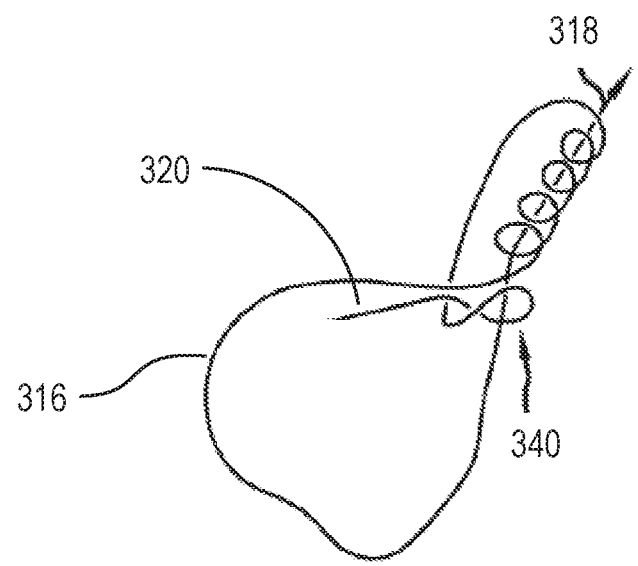

Bight 340 can define a knot when the first end 318 of suture 316 passes therethrough, as can be understood with reference to FIGS. 12A-12D. Bight 340 can include one or more loops, and can be pre-arranged so as to define a square knot using the general layout illustrated in FIG. 13A, a cinch knot using the general layout illustrated in FIG. 13B, or a variety of known or new surgical knots.

The knot can be completed by pulling second penetrator 136b, short suture 264, and first end 318 of suture 316 (together with cuffs 166a and 166b and detachable first penetrator tip 314) proximally through bight 340. Second end 320 of suture 316 can be pulled to free bight 340, and the ends 318 and 320 of suture 316 can be tightened and the tissue closure device removed to provide permanent hemostasis.

In an alternative embodiment of tissue closure device 200, a slot can be included, distal of arms 202, that includes a passage that defines a suture bearing surface through which link 264 and second cuff 166b can pass. Instead of link 264 attaching directly between first and second cuffs 166a and 166b across the tissue opening, an intermediate portion of the link can be positioned within the passage. Then, when the penetrators are withdrawn proximally, the link, the second cuff, and the suture can all pass through the passage before being withdrawn proximally through the first penetrator path.

Using a passage can provide some unique benefits. For example, the suture bearing surface can bear forces placed on the suture during suturing. As such, the suture-bearing surface can minimize forces placed on an incision during incision tensioning, thereby minimizing the possibility of damaging tissue immediately surrounding the incision.

Figure 14A:
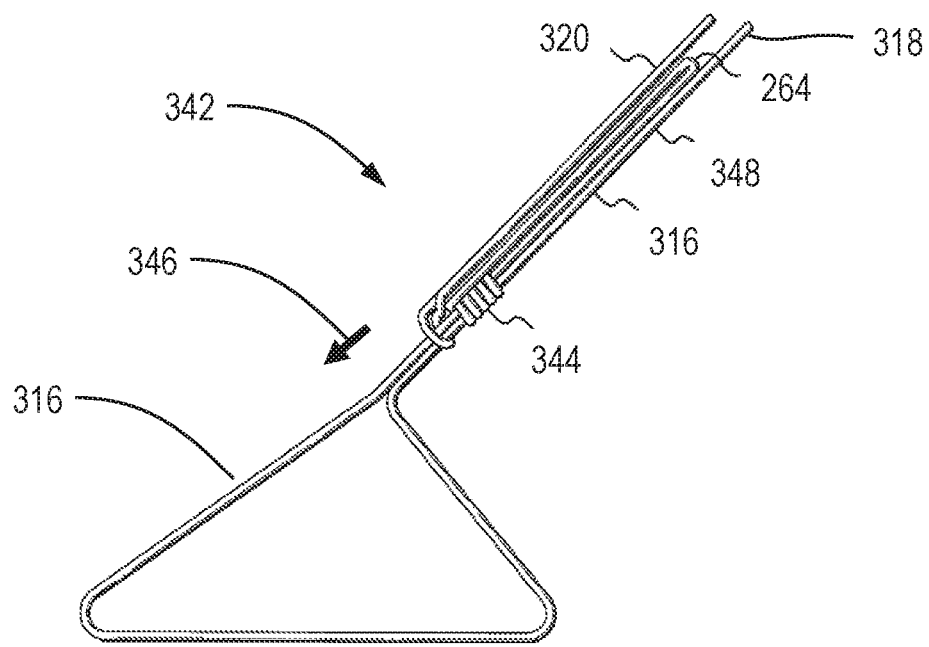
FIGS. 14A and 14B are schematic views of a suture bight having a pre-tied knot in accordance with one embodiment of the present invention.
Figure 14B:
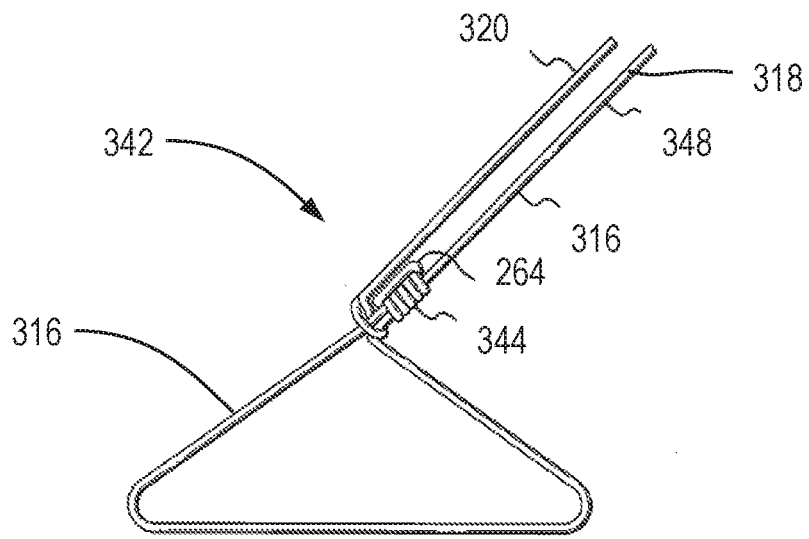

FIGS. 14A and 14B show one embodiment of a suture bight 342 that can be used with suture link 264. FIG. 14A depicts suture bight 342 in a pre-deployed state and FIG. 14B depicts suture bight 342 in a deployed state. As the suture link 264 and the suture 316 move, a pre-tied suture knot 344 can also move in the same direction as the suture loop 264, as indicated by directional arrow 346. Suture loop 264 can continue to move pre-tied suture knot 344 towards the incision until suture 316 and pre-tied suture knot 344 close the incision formed in the vessel wall.

Suture 316 can be arranged to provide the pre-tied knot 344 that automatically travels down from the shaft of the tissue closure device where the knot can be stored prior to delivery to the tissue wall. The suture loop 264 can serve to pull knot 344 down a rail portion 348 of suture 316 during deployment. If desired, the ends 318 and 320 of suture 316 can be differentiated from each other so the operator can distinguish them and pull the correct end to advance and tighten the knot.

Figure 15A:
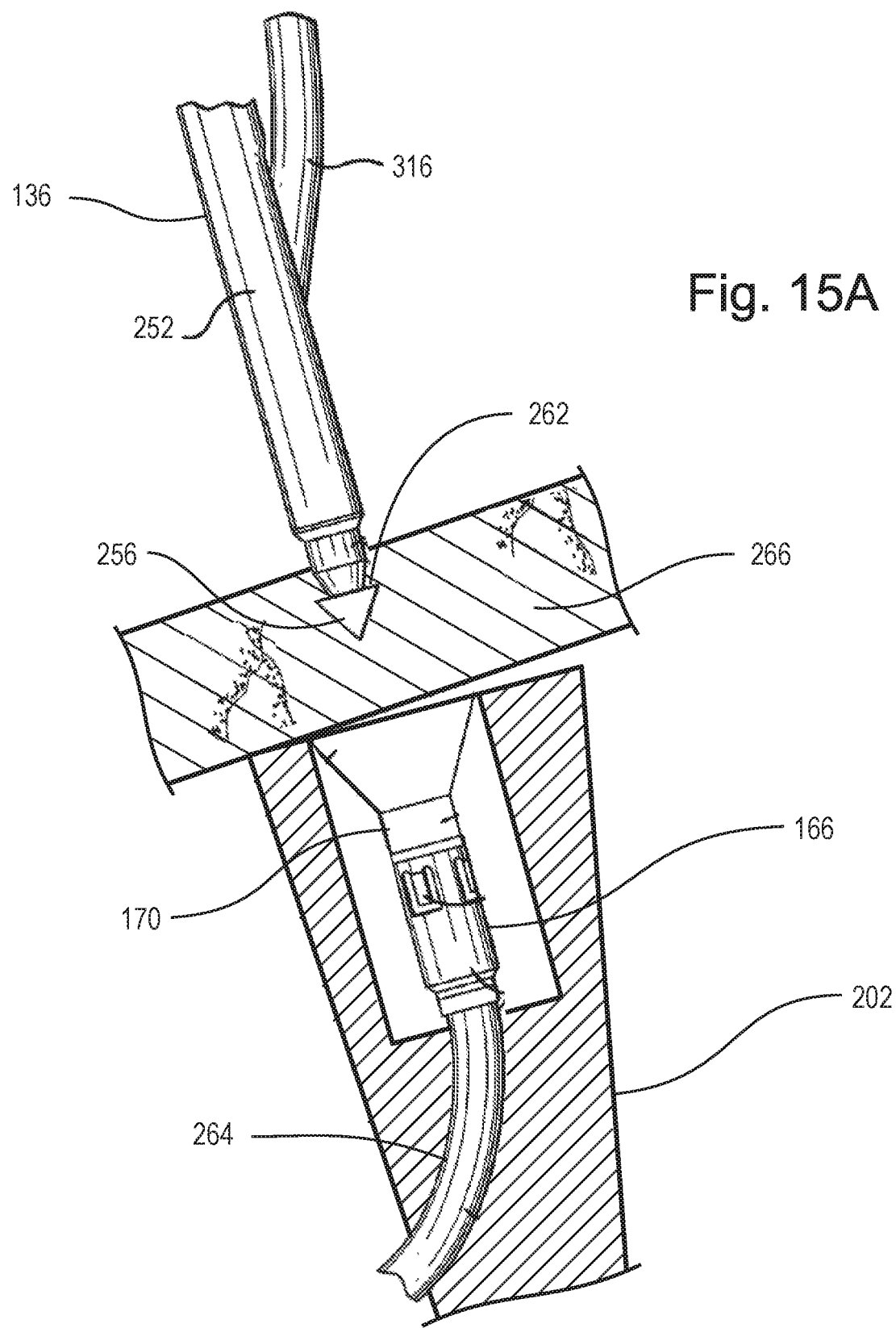
FIGS. 15A-D illustrate one embodiment of a method of attaching a suture to a cuff and releasing the cuff from the arm using a penetrator and then disengaging the penetrator from the cuff.

FIGS. 15A-D illustrate a method of attaching suture 316 to cuff 166 and releasing cuff 166 from arm 202 using penetrator 136. As such, the illustrated method can be used to attach suture 316 to the second cuff 166b using second penetrator 136b in the second method discussed above. Penetrator 136 may be any type of structure capable of penetrating the wall of a lumen, such as an artery, a blood vessel, or the like. In addition to the penetration capability, the penetrator may incorporate a hollow tube capable of holding suture. Examples of such structures may include a hypodermic needle or the like. As discussed above, in many embodiments the tissue locator can store penetrator 136 within its shaft, as shown in FIG. 7A. As previously described with reference to FIGS. 2A through 2C, a user can deploy a handle of the suturing device to deploy penetrator shank 252 and its corresponding penetrator tip 256. During deployment, penetrator shank 252 and penetrator tip 256 penetrate the lumen wall 266 immediately surrounding the incision or other tissue opening, as shown in FIG. 15A.

Figure 15B:
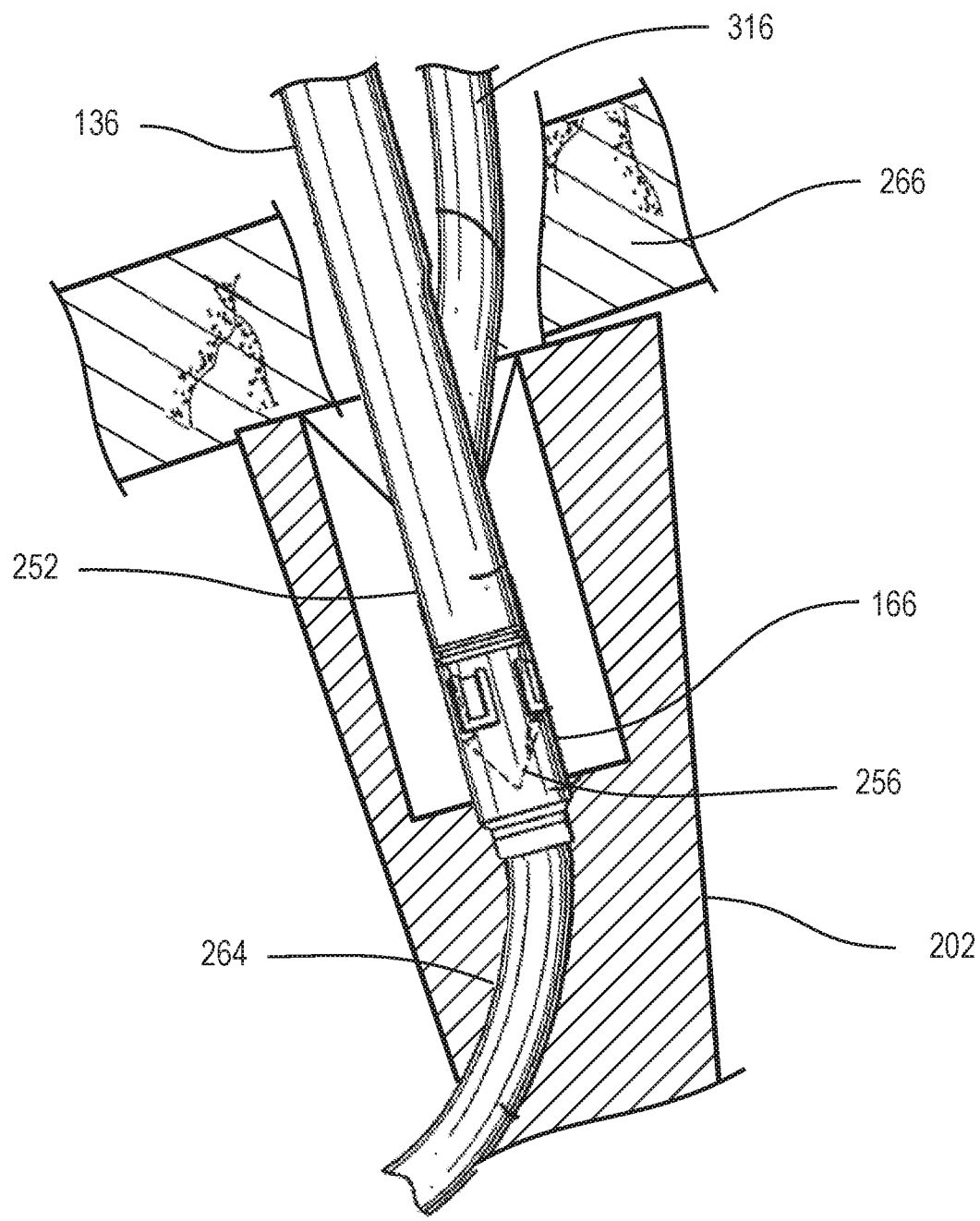

Penetrator 136 is advanced through lumen wall 266 until penetrator tip 256 engages with cuff 166, which is positioned within cuff recess 170. Once penetrator tip 256 engages with cuff 166, the penetrator can be further advanced so that penetrator tip 256 advances cuff 166 further into arm 202, as shown in FIG. 15B. As may be seen with reference to FIG. 15B, cuff 166 can be thereby dislodged out of pocket 170 (FIG. 15A) and into a lumen in arm 202. Once cuff 166 has been dislodged from pocket 170, a push mandrel 350 can be used to detach penetrator tip 256 from penetrator shank 252 as shown with reference to FIG. 15C.

Figure 15C:
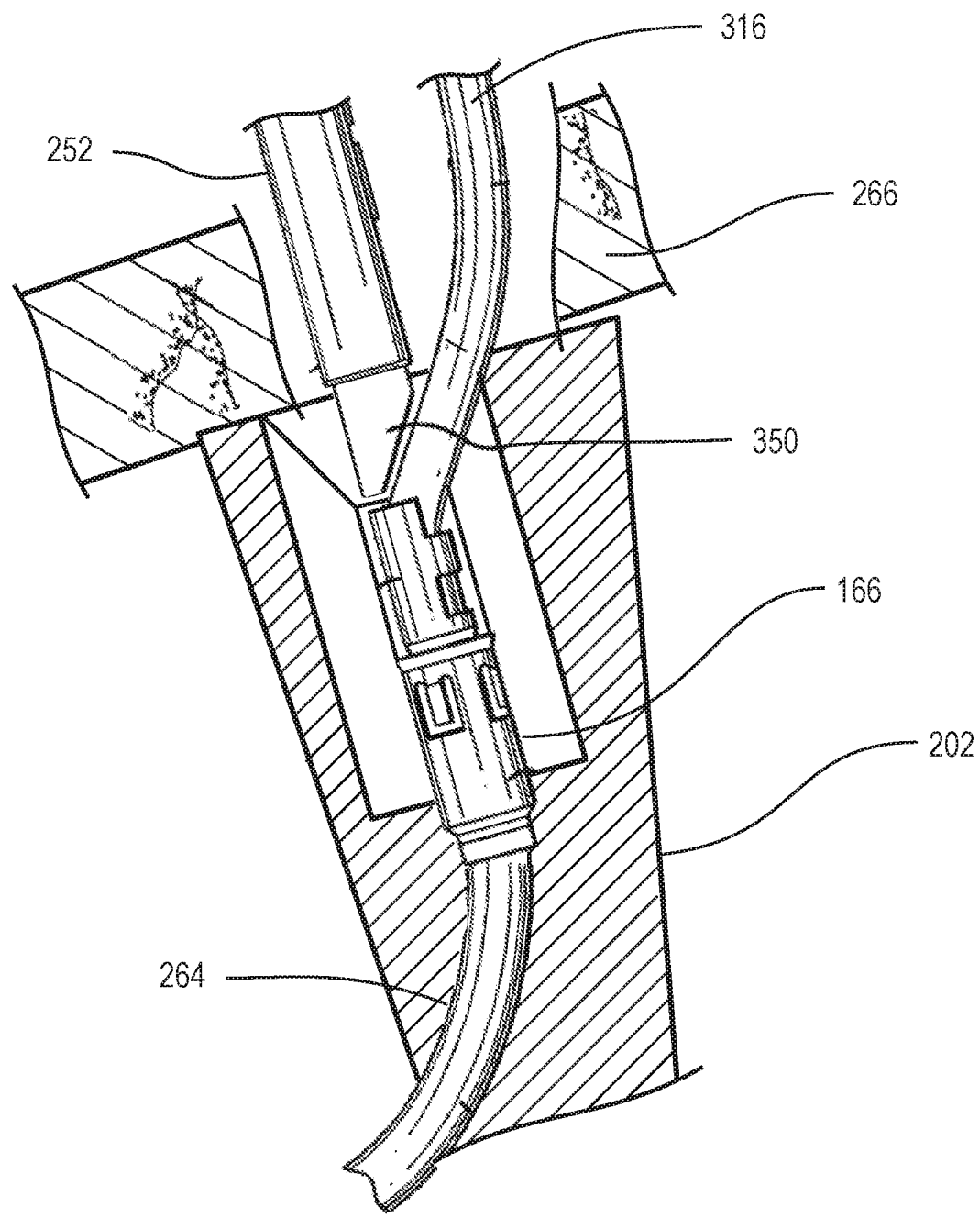

FIG. 15C illustrates the detachment of penetrator tip 256 from penetrator shank 252 in accordance with one embodiment of the present invention. Upon engagement of penetrator tip 256 with cuff 166, push mandrel 350 is further advanced such that it contacts proximal surface 262 of penetrator tip 256, and further still until penetrator tip 256 detaches from penetrator shank 252.

Figure 15D:
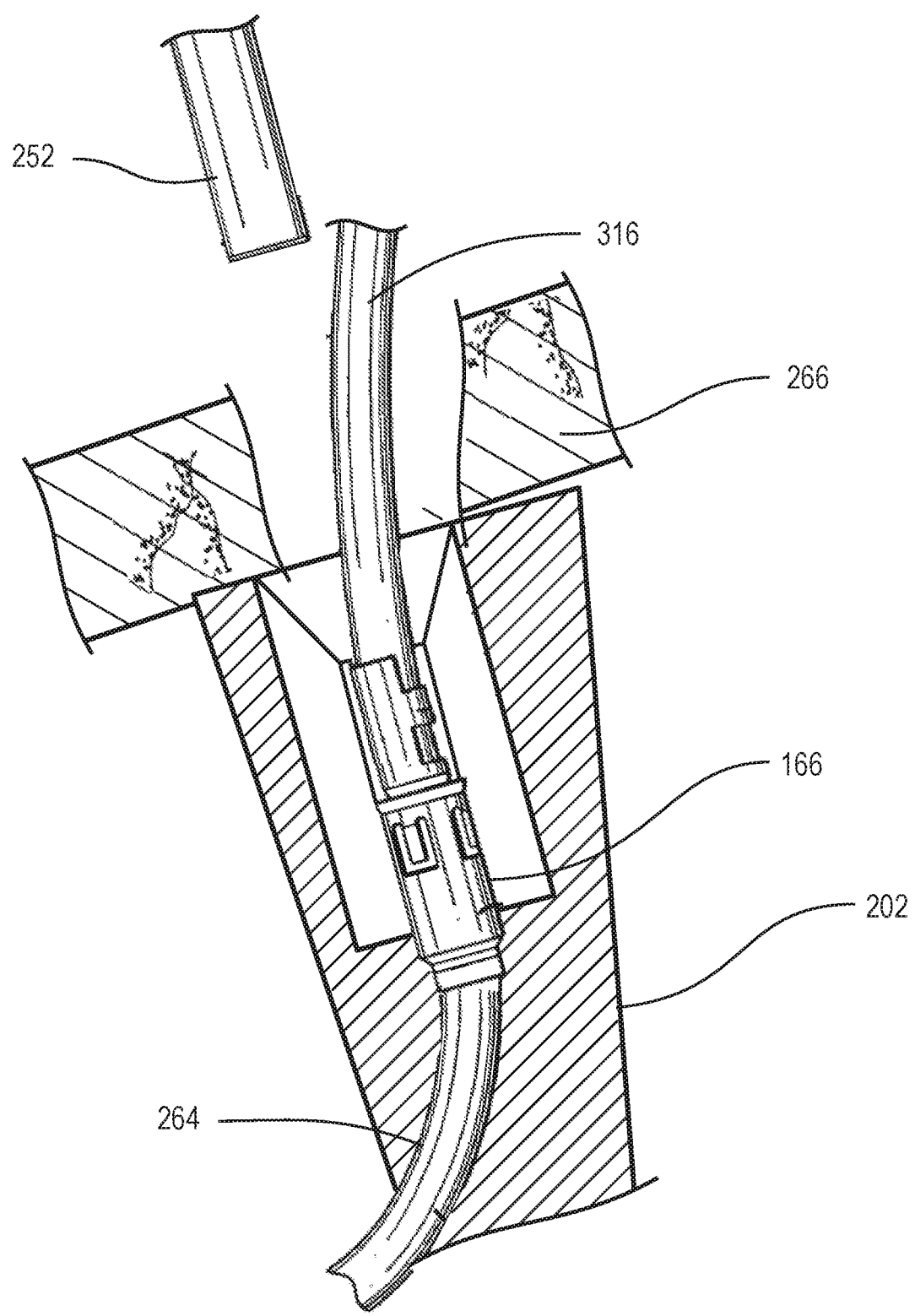

As shown in FIG. 15D, after penetrator tip 256 detaches from penetrator shank 252, penetrator shank 252 retracts from penetrator tip 256 and cuff 166, leaving suture 316 attached to cuff 166. Then, when suture link 264 is pulled across the tissue opening by the penetrator on the other side of the tissue locator (not shown), cuff 166 and attached suture 316 will follow, as discussed in the second method above.

Figure 16A:
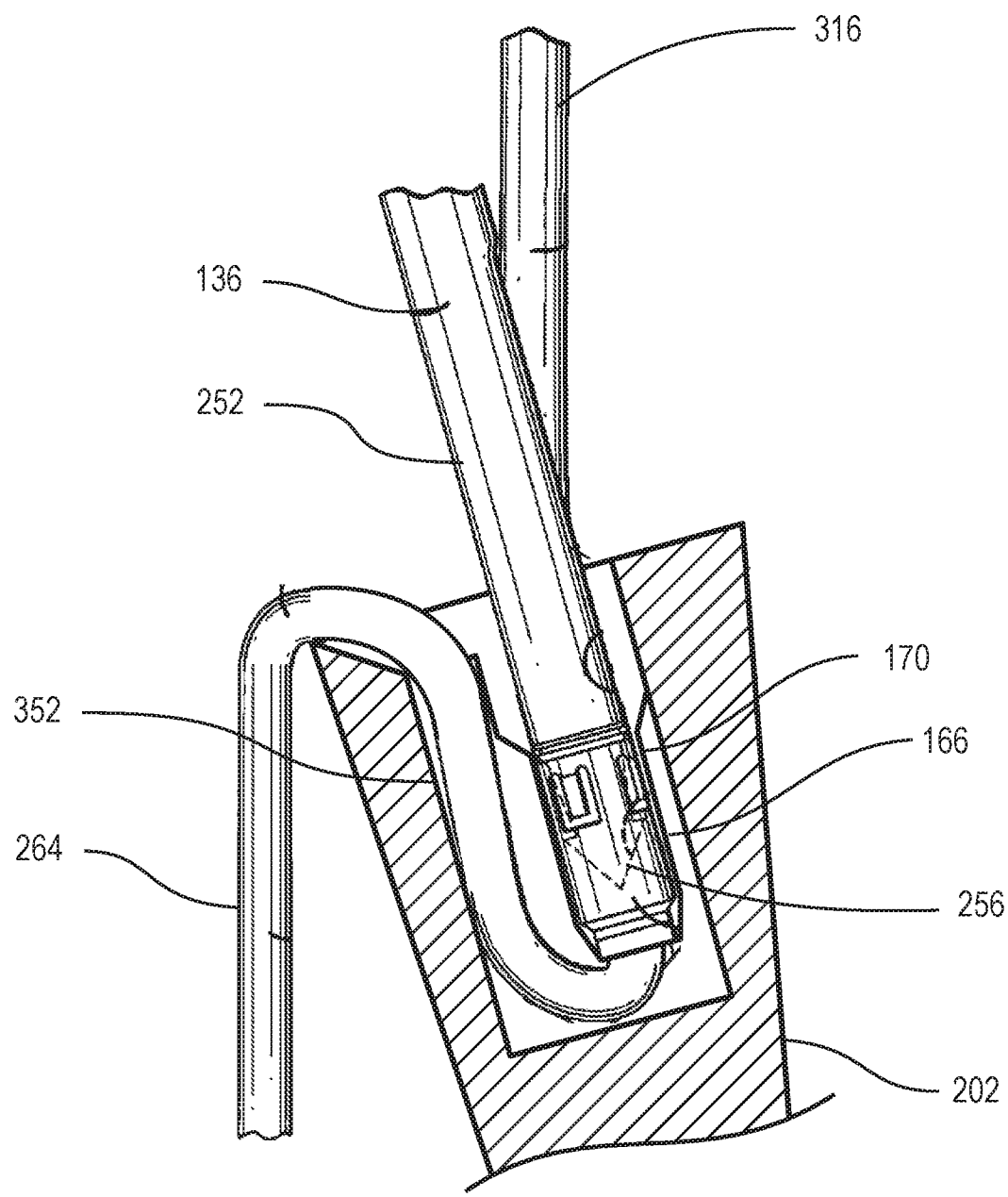
FIGS. 16A and 16B illustrate an alternative embodiment for releasing the cuff from the arm.
Figure 16B:
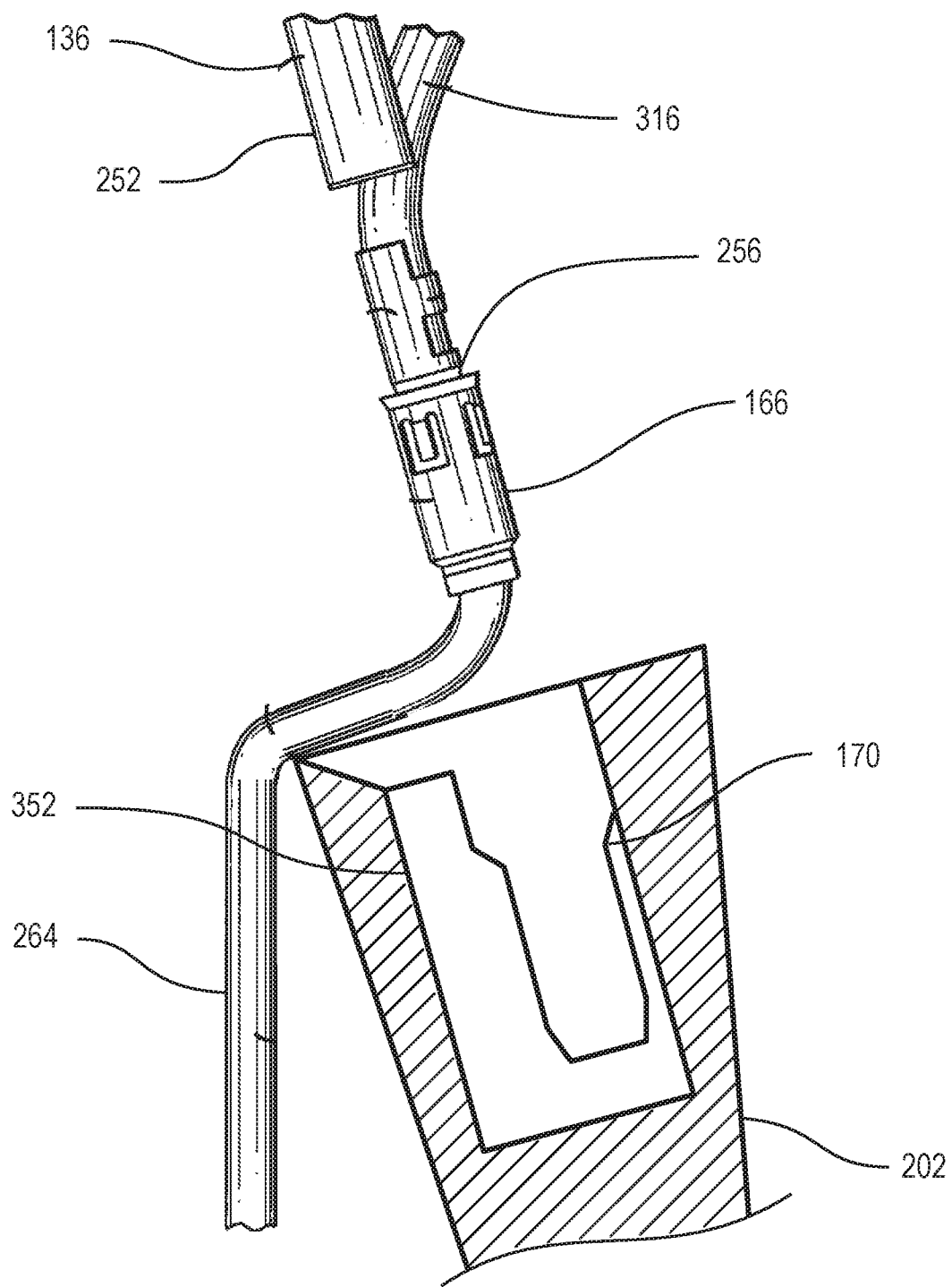

FIGS. 16A and 16B illustrate an alternative embodiment for releasing cuff 166 from arm 202. In this embodiment, arm 202 includes link passageway 352 through which link 264 passes. After penetrator shank 252 engages penetrator tip 256 with cuff 166, penetrator shank 252, during retraction from arm 202, removes cuff 166 and penetrator tip 256 from the arm. The force holding penetrator tip 256 on penetrator shank 252 overcomes the force holding cuff 166 in cuff pocket 170. Once cuff 166 clears arm 202 and attains the orientation shown with reference to FIG. 16B, the previously described push mandrel (not shown) can detach penetrator tip 256 from penetrator shank 252. Upon detachment of penetrator tip 256 from penetrator shank 252, cuff 166 and attached suture 316 are free to be pulled across the tissue opening by link 264, as discussed above. In an alternate embodiment, cuff 166 and penetrator tip 256 may be pulled off elongated shank 252 by tension in link 264. Alternatively, cuff 166 and penetrator tip 256 may be detached from penetrator shank 252 before being removed from cuff pocket 170.

Figure 17A:
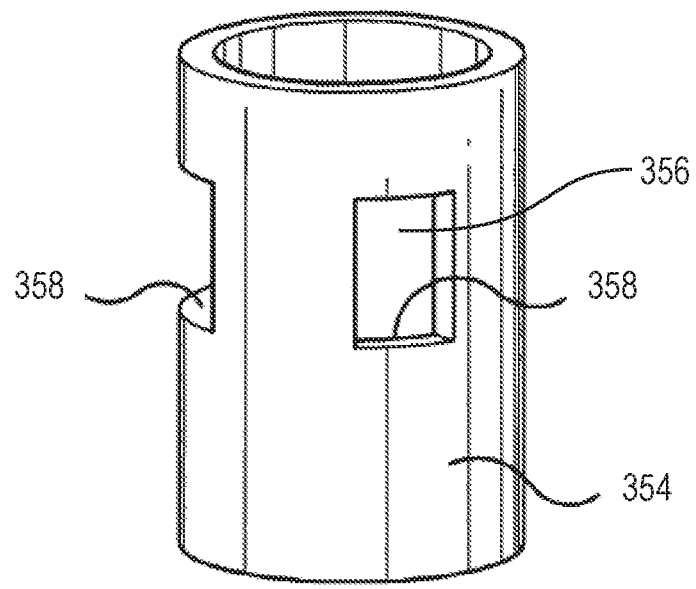
FIGS. 17A and 17B are perspective views of an alternative embodiment of a penetrator tip.
Figure 17B:
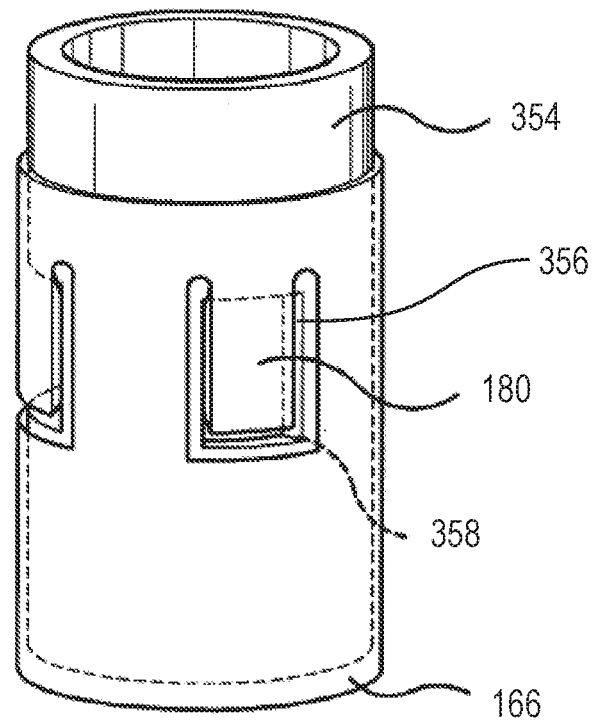

Alternative cuff configurations may be used that facilitate engagement of penetrator bodies 252 with link 264. For example, FIG. 17A illustrates a perspective view of an alternative embodiment of a penetrator tip 354 that can be used with cuff 166. In this embodiment, penetrator tip 354 includes windows 356 with proximal facing mating surfaces 358 which engage with tabs 180 of cuff 166 when penetrator tip 354 engages with cuff 166, as shown in FIG. 17B. As such, a user can detach penetrator shank 252 from penetrator tip 196 with push mandrel 350 after engagement of penetrator tip windows 356 with cuff tabs 180, as discussed with reference to penetrator tip 256 and cuff 166.

Figure 18A:
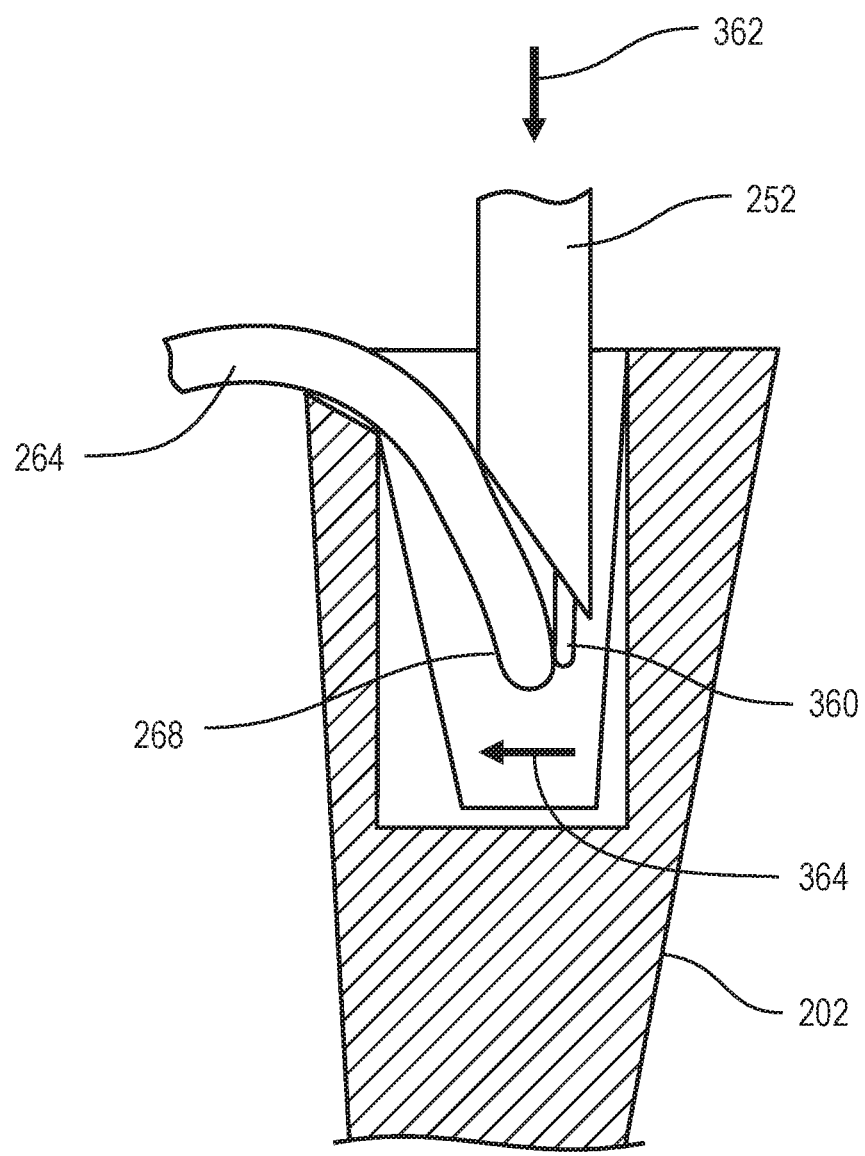
FIGS. 18A through 18C are schematic views of an alternate embodiment of a penetrator and how it can be used to engage with a link.
Figure 18B:
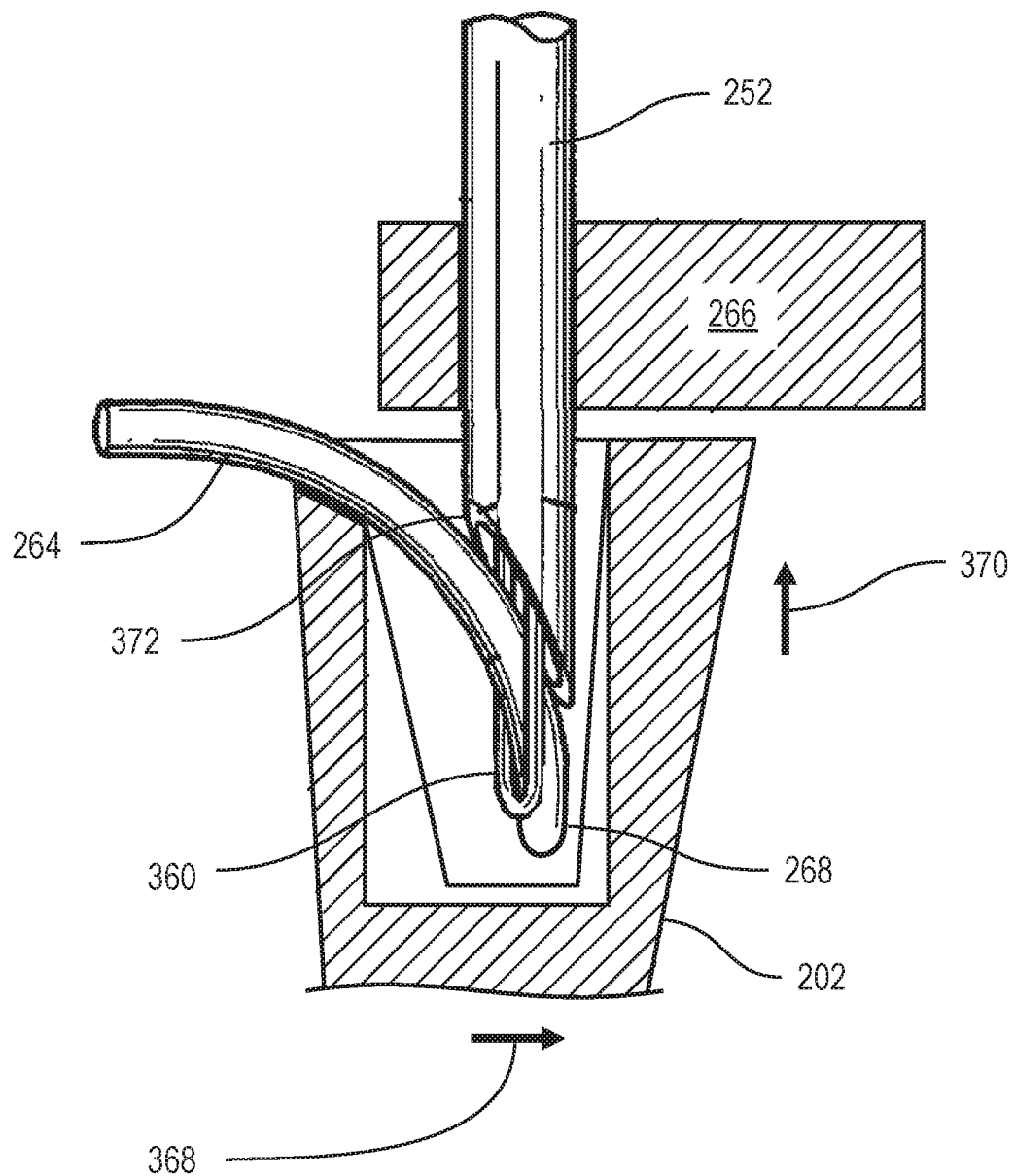
Figure 18C:
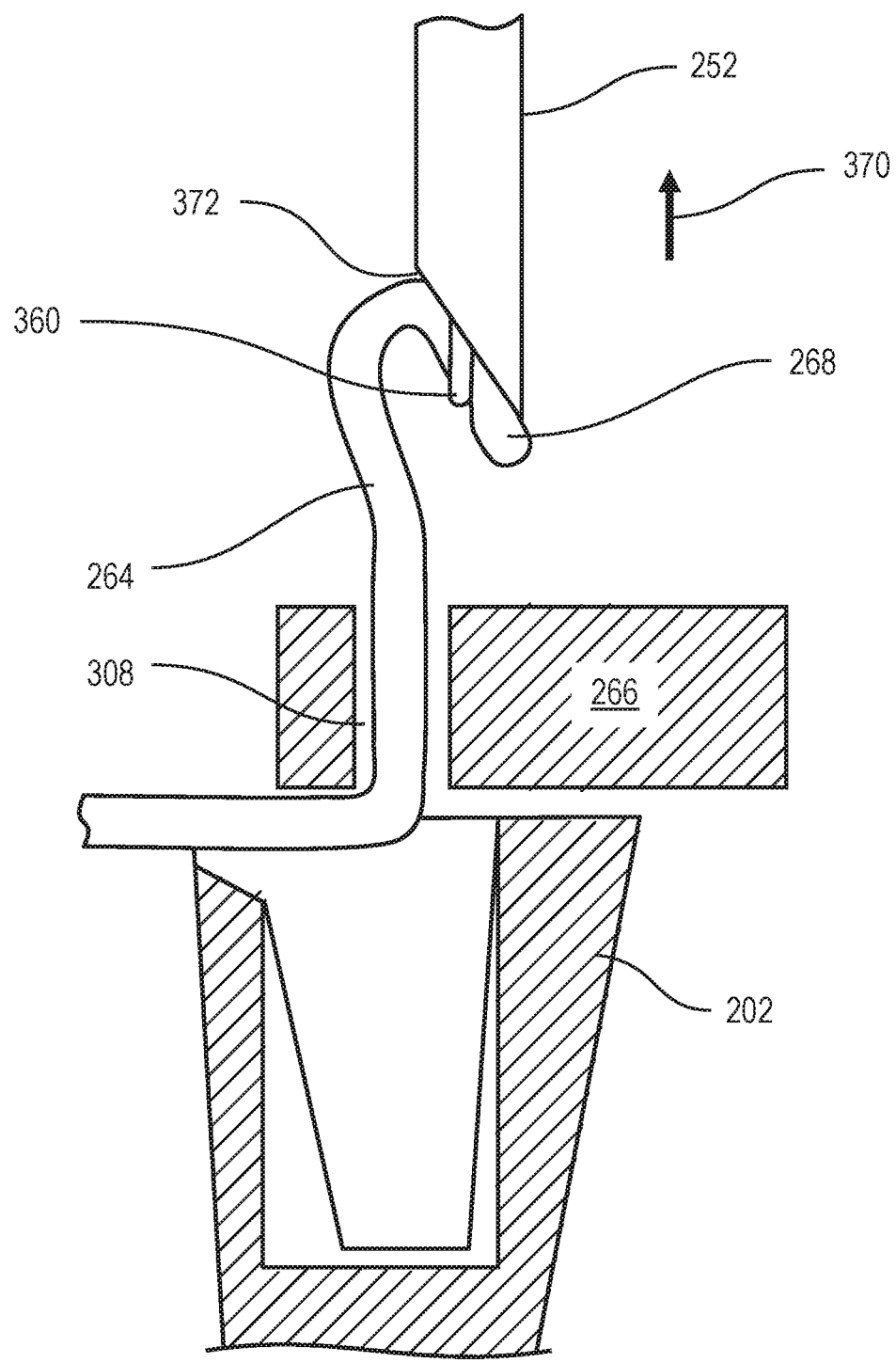

FIGS. 18A-C show an alternative method of coupling penetrator shank 252 with link 264. In this embodiment, penetrator shank 252 includes a loop 360 which engages with link 264 as penetrator shank 252 enters arm 202. To facilitate the engagement, link 264 is constructed of a resilient material capable of flexing in response to loop 360 contacting link 264, such as polypropylene or any other material having spring-like characteristics.

As shown in FIG. 18A, penetrator shank 252 moves distally into arm 202 in the direction indicated by directional arrow 362 until loop 360 comes into contact with an end 268 of link 264. When loop 360 contacts the end 268, loop 360 moves the end 268 in the direction indicated by directional arrow 364. As penetrator shank 252 continues to distally advance, loop 360 continues to move the end 268 of link 264 in the direction 364 until loop 360 advances beyond the end 268 of link 264.

As noted above, link 264 can be constructed of a material having spring like properties. As such, when loop 360 advances beyond the end 268 of link 264, the resilient properties of link 264 move the end 268 in the direction indicated by directional arrow 368 in FIG. 18B. The end 268 of link 264 moves in the direction 368 such that the end 268 of link 264 moves into loop 360, as shown in FIG. 18B. Once the end 268 of link 264 moves into loop 360, loop 360 can be retracted into the penetrator shank 252 in the direction indicated by directional arrow 370. In some embodiments the end 268 of link 264 also moves into penetrator shank 252 with loop 360. In some embodiments, the end 268 of link 264 remains outside of penetrator shank 252.

As shown in FIG. 18C, as loop 360 moves in the direction 370, loop 360 clamps link 264 against a surface 372 of the elongate shank 252. As a result, during retraction of the penetrator from arm 202, link 264 remains engaged with penetrator shank 252. As penetrator shank 252 and loop 360 retract from arm 202, loop 360 pulls link 264 through penetrator path 308, as shown in FIG. 18C. While loop 360 pulls link 264, cuff 166 (not shown) and the suture 152 (not shown) also can move through penetrator path 308 in order to enable closure of a tissue opening.

Figure 19A:
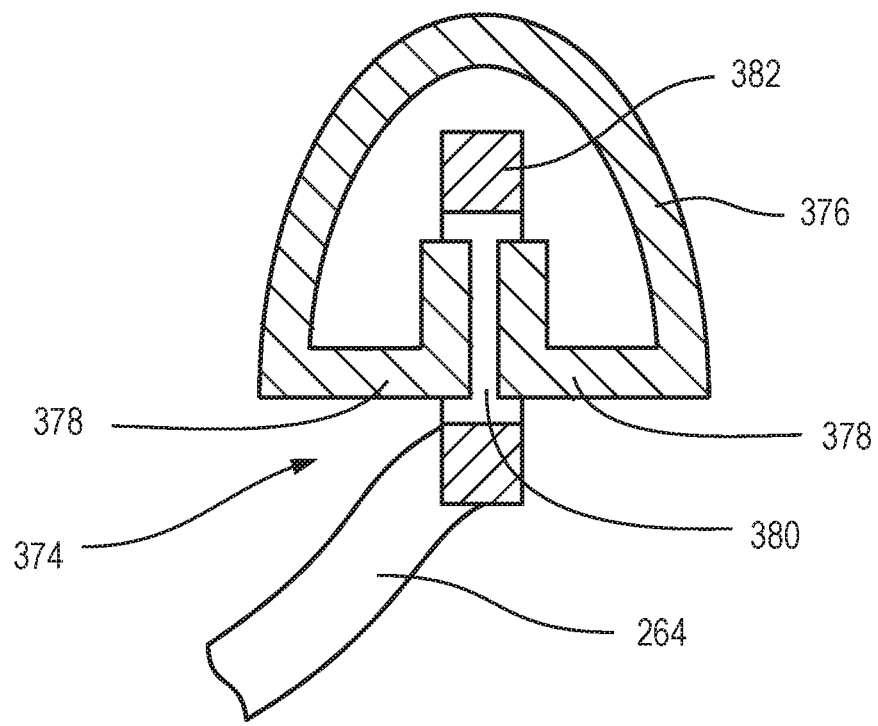
FIGS. 19A through 19G are schematic views of an alternate embodiment of a penetrator that includes a clamp and ring assembly.
Figure 19B:
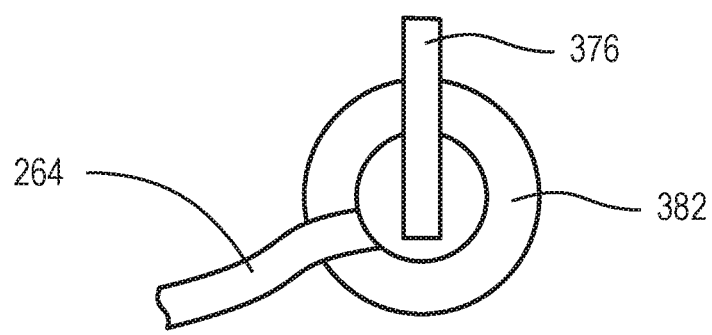
Figure 19C:
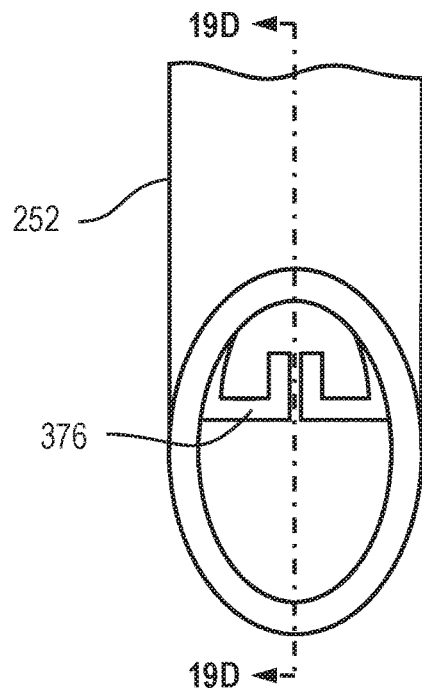
Figure 19D:
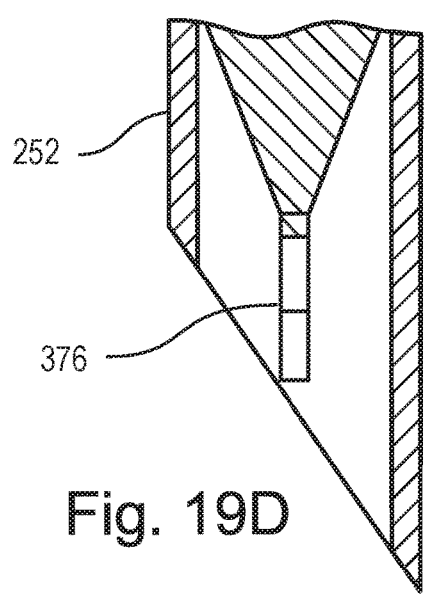
Figure 19E:
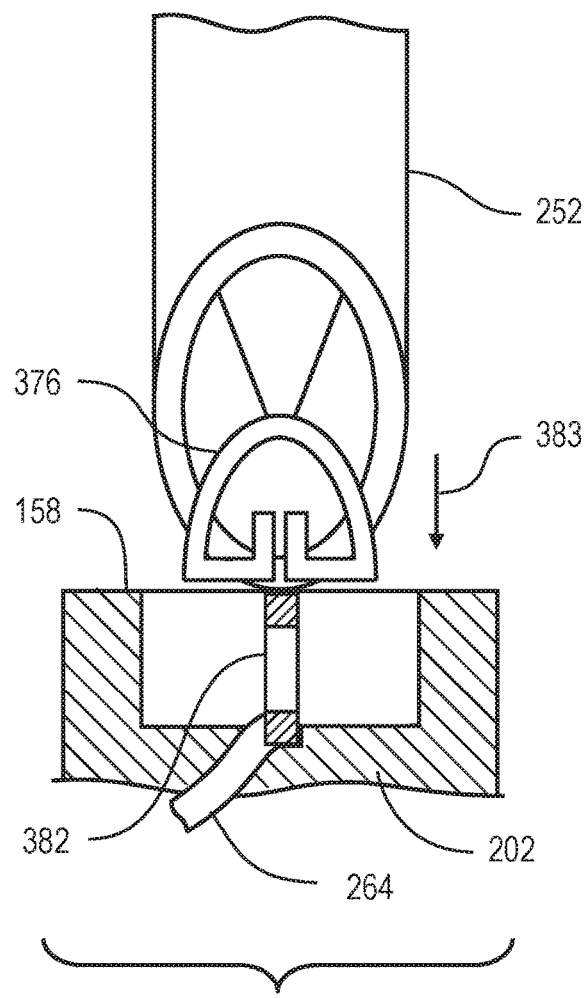

In another embodiment, the suturing device 150 may also employ a clip and ring assembly 374 to couple the penetrator bodies 252 with link 264, as shown with reference to FIGS. 19A-G. FIGS. 19A and 19B illustrate clip and ring assembly 374 in an attached configuration. Clip and ring assembly 374 comprises a clip 376 and a ring 382 that engages with clip 376. Each clip 376 can include flexible arms 378 and a passageway 380 between the arms 378. Ring 382 can have a circular configuration as shown with respect to FIG. 19B. Initially, the clip 376 can be incorporated into penetrator shank 252 in place of penetrator tip 256 or needle tip 314. Alternatively, clip 376 can be initially positioned within penetrator 252 and extendable therefrom, as shown in FIGS. 19C and 19D. Ring 382 can initially be positioned within arm 202 and coupled to link 264, as shown in FIG. 19E. Link 264 can couple with the ring 382 using any suitable technique, such as tying or the like.

Figure 19F:
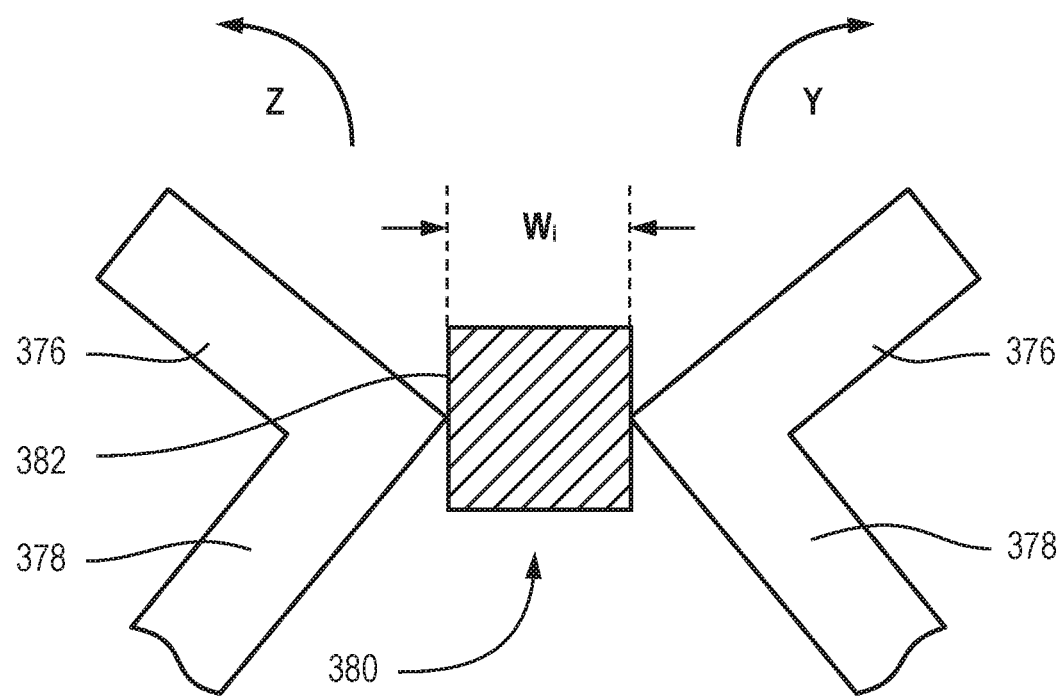

As shown in FIG. 19E, as the elongate shank 252 engages with arm 202, clip 376 can be advanced, as indicated by arrow 383, to couple with ring 382. As illustrated in FIG. 19F, as clip 376 engages with ring 382, flexible arms 378 flex in a direction indicated by directional arrows Y and Z thereby increasing a width $W_i$ of passageway 380 in order to allow passage of ring 382 through passageway 380 of clip 376.

Figure 19G:
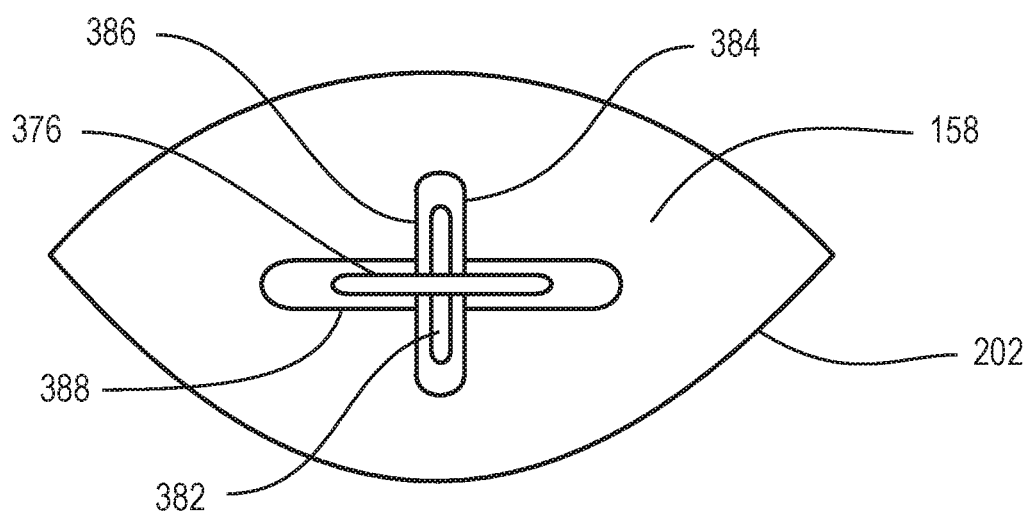

Referring to FIG. 19G, there is shown a top view of end face 158 of arm 202 where arm 202 can include a cuff pocket 384 having a pair of elongated openings 386 and 388 that intersect in the middle to form a cross. Cuff pocket 384 holds ring 382 such that ring 382 is general positioned in opening 386 prior to engagement with clip 376. Cuff pocket 384 is configured such that as penetrator shank 252 engages arm 202, clip 376 can enter opening 388 and engage with ring 382 as shown. Once clip 376 engages with ring 382, ring 382, which is coupled with link 264, can detach from cuff pocket 384 while penetrator shank 252 remains engaged with clip 376.

Figure 20:
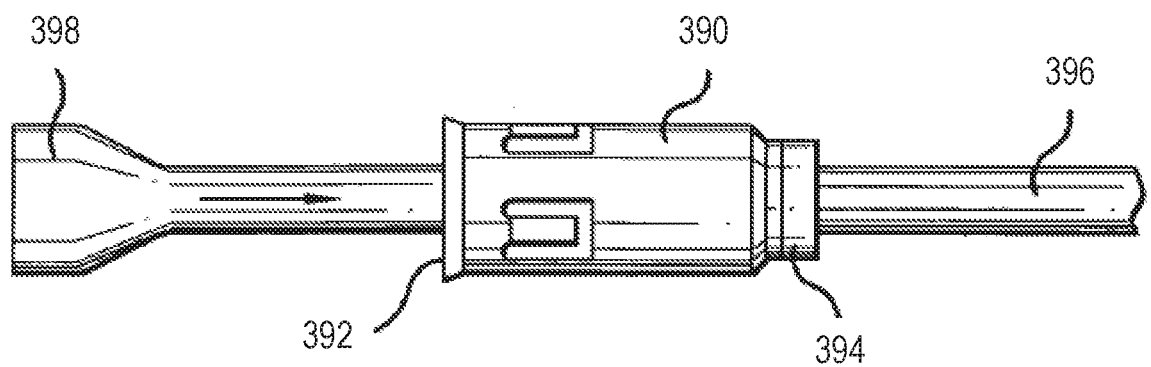
FIG. 20 shows a schematic view of one embodiment of a cuff and link assembly.

FIG. 20 shows an embodiment of a cuff and link assembly that may be used with various embodiments. Cuff 390 has a penetrator tip receiving end 392 and a tapered end 394. Link 396 has two ends 398 (only one shown in FIG. 20). An example of a preferred link material is expanded Polytetrafluoroethylene (ePTFE), more commonly referred to as teflon. ePTFE is particularly suited for use as the link material in the vessel closure devices described herein because of its low friction, high strength properties.

To assemble the link and cuff assembly, a length of link 396 is first threaded through cuff 390. The end 398 of link 396 extending from penetrator tip receiving end 392 of cuff 390 is then heated so that end 398 of link 396 expands. Link 396 is then pulled through cuff 390 such that the expanded end portion 398 is seated in the interior tapered end 394 of cuff 390.

In some embodiments it may be advantageous to provide multiple suture loops across the tissue opening. For example, closure of a large opening may require two three or more pairs of loops. To accommodate this, tissue closure devices can incorporate more than two arms.

Tissue locators envisioned herein may contain any number of arms. For example, tissue locators having four, six, eight, ten or more arms are possible. Independent of the number of arms, all of the arms can be essentially identical and positioned on the tissue locator so as to be radially spaced about the tissue opening. The arms can be equidistantly placed about the tissue opening or can have varying distances between them.

By using more arms, multiple suture links can be formed using the cuffs in the arms. For example, for any even number of arms, a number of links equal to half the number of arms can be formed, where each link spans between two of the cuffs. For example for tissue locators having four, six, eight, and ten arms, two, three, four, and five links can be formed, respectively. The links can be formed between diametrically opposed cuffs or between any of the cuffs, as discussed below. Each link and corresponding cuffs can be employed in any of the manners discussed above.

Figures 21A, 21B:
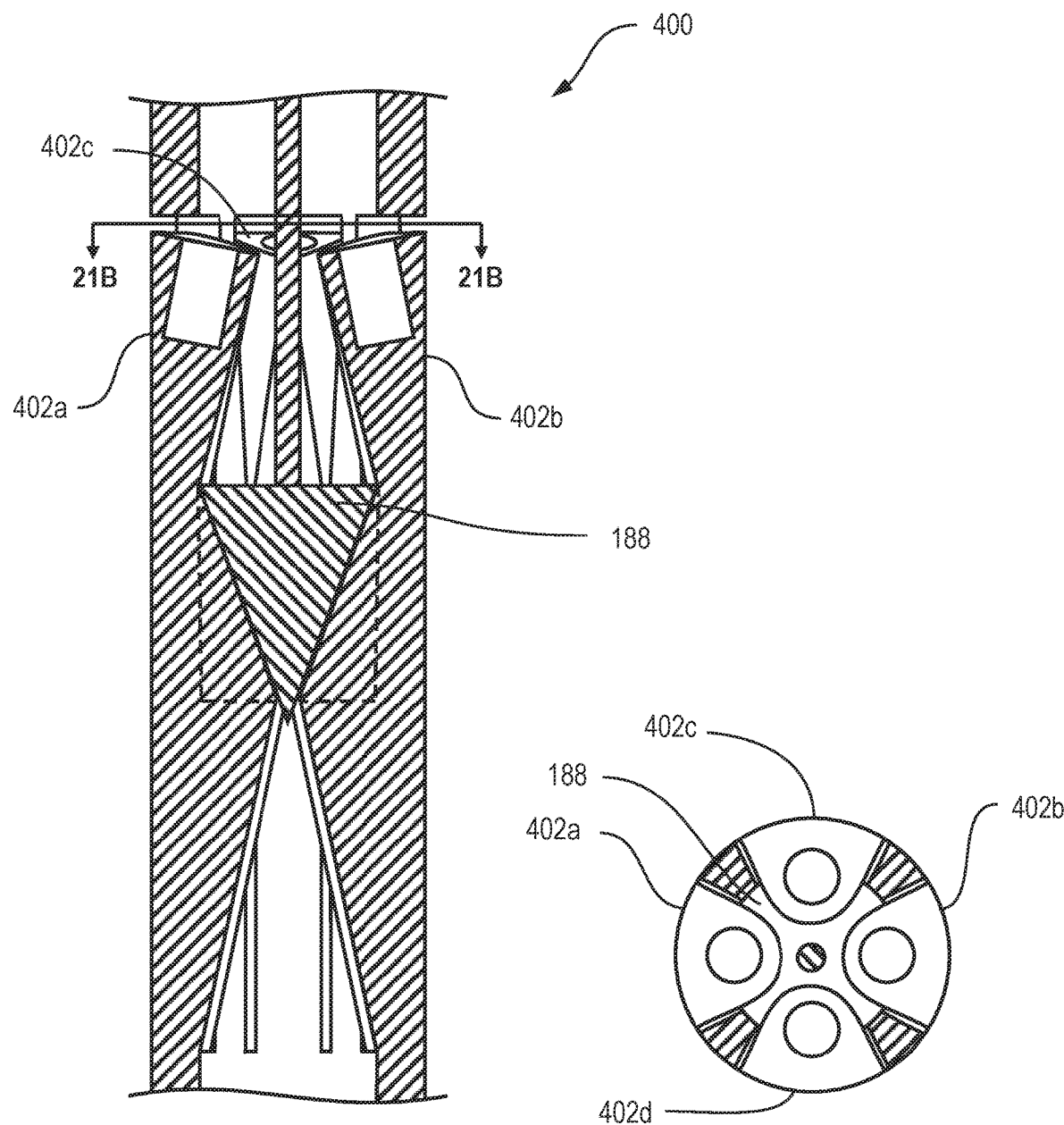
FIGS. 21A-21D are cross-sectional side and top views of another embodiment of a tissue locator that can be used in the tissue closure devices shown in FIGS. 1 and 2 showing the arms in the retracted position (FIGS. 21A and 21B) and in the deployed position (FIGS. 21C and 21D).
Figure 21C:
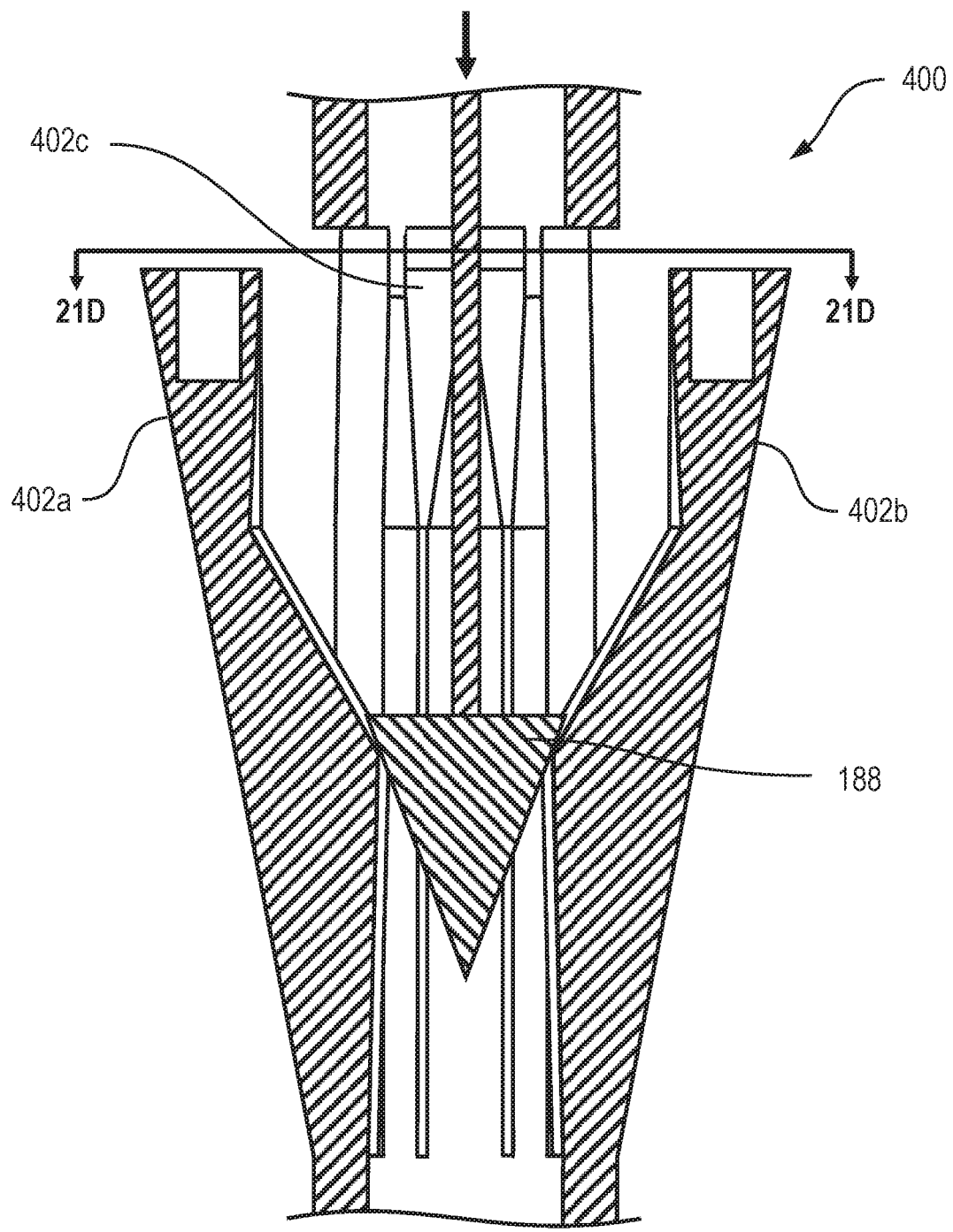
Figure 21D:
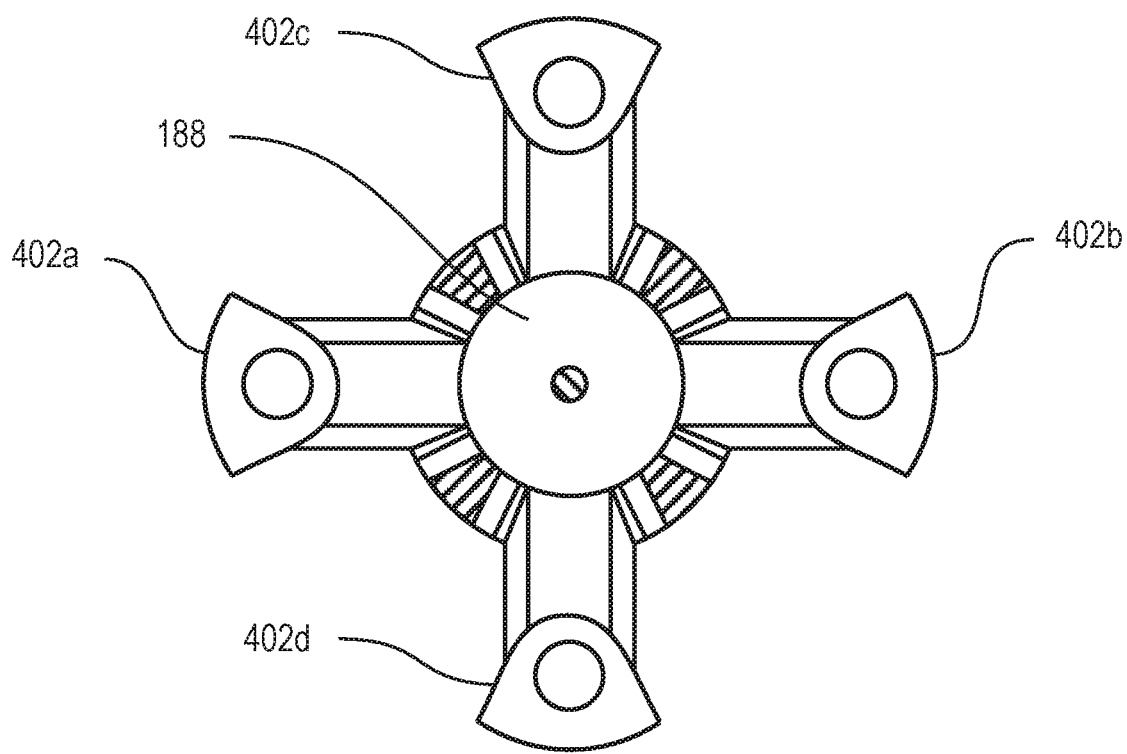

FIGS. 21A through 21D show one embodiment of a tissue locator 400 that incorporates four arms. Tissue locator 400 is similar to tissue locator 200 (see FIGS. 5A-5D), except for the additional arms. That is, similar to tissue locator 200, tissue locator 400 has a pair of arms 402a and 402b diametrically opposed to each other with respect to central axis 122. However, unlike tissue locator 200, tissue locator 400 also has a second pair of arms 402c and 402d, also diametrically opposed to each other with respect to central axis 122. As such, there are four arms 402 arranged radially about central axis 122, as particularly shown in FIGS. 21B and 21D. Similar to the embodiments discussed above, each arm 402 can include a penetrator receptacle 164 and a cuff 166 releasably positioned therein. Also similar to the tissue locators discussed above, each arm 402 can pivot about its distal end 152 between the retracted position, as shown in FIGS. 21A and 21B, and the deployed position shown in FIGS. 21C and 21D by distal movement of expander 188.

Figures 22A, 22B:
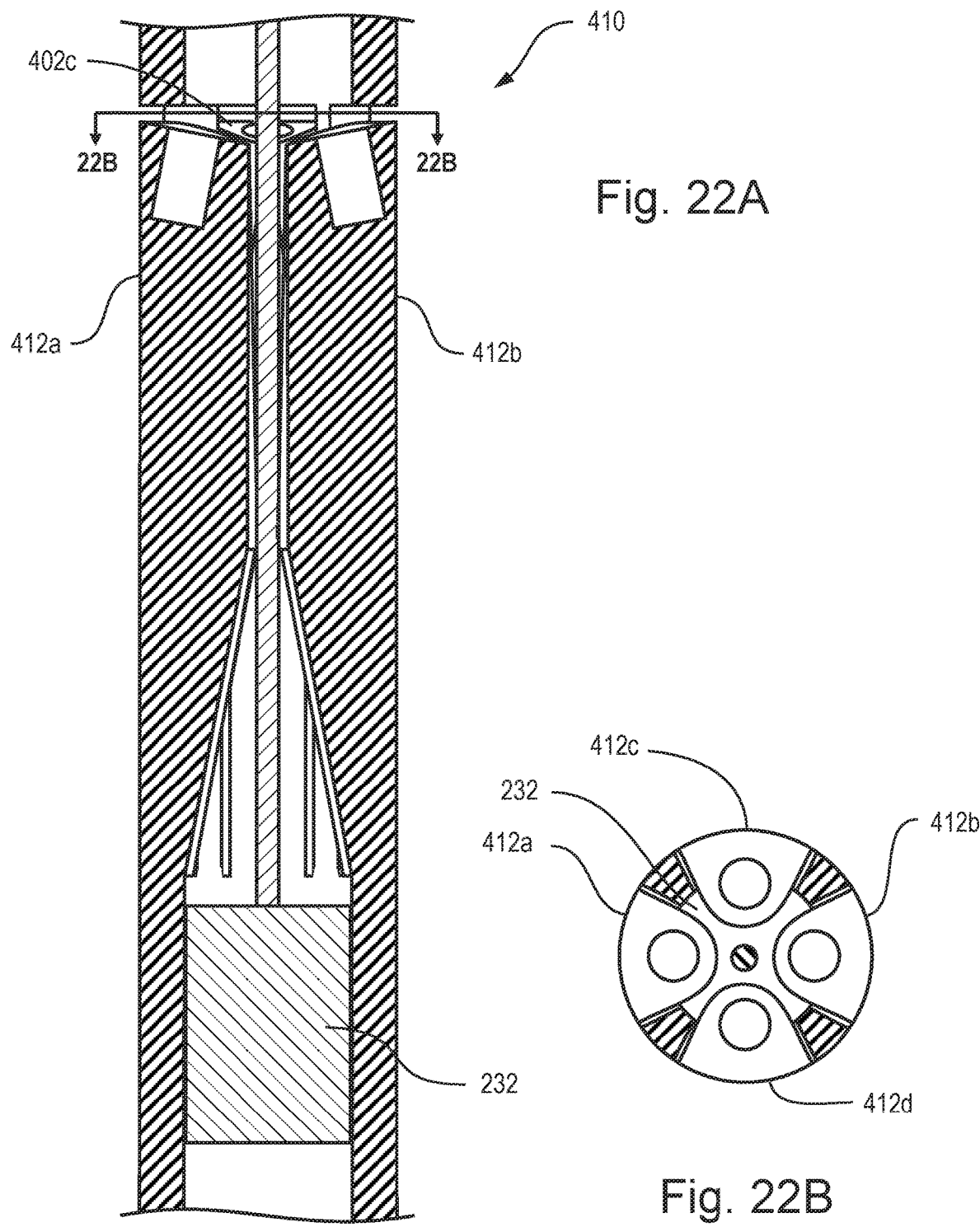
FIGS. 22A-22D are cross-sectional side and top views of another embodiment of a tissue locator that can be used in the tissue closure devices shown in FIGS. 1 and 2 showing the arms in the retracted position (FIGS. 22A and 22B) and in the deployed position (FIGS. 22C and 22D).
Figure 22C:
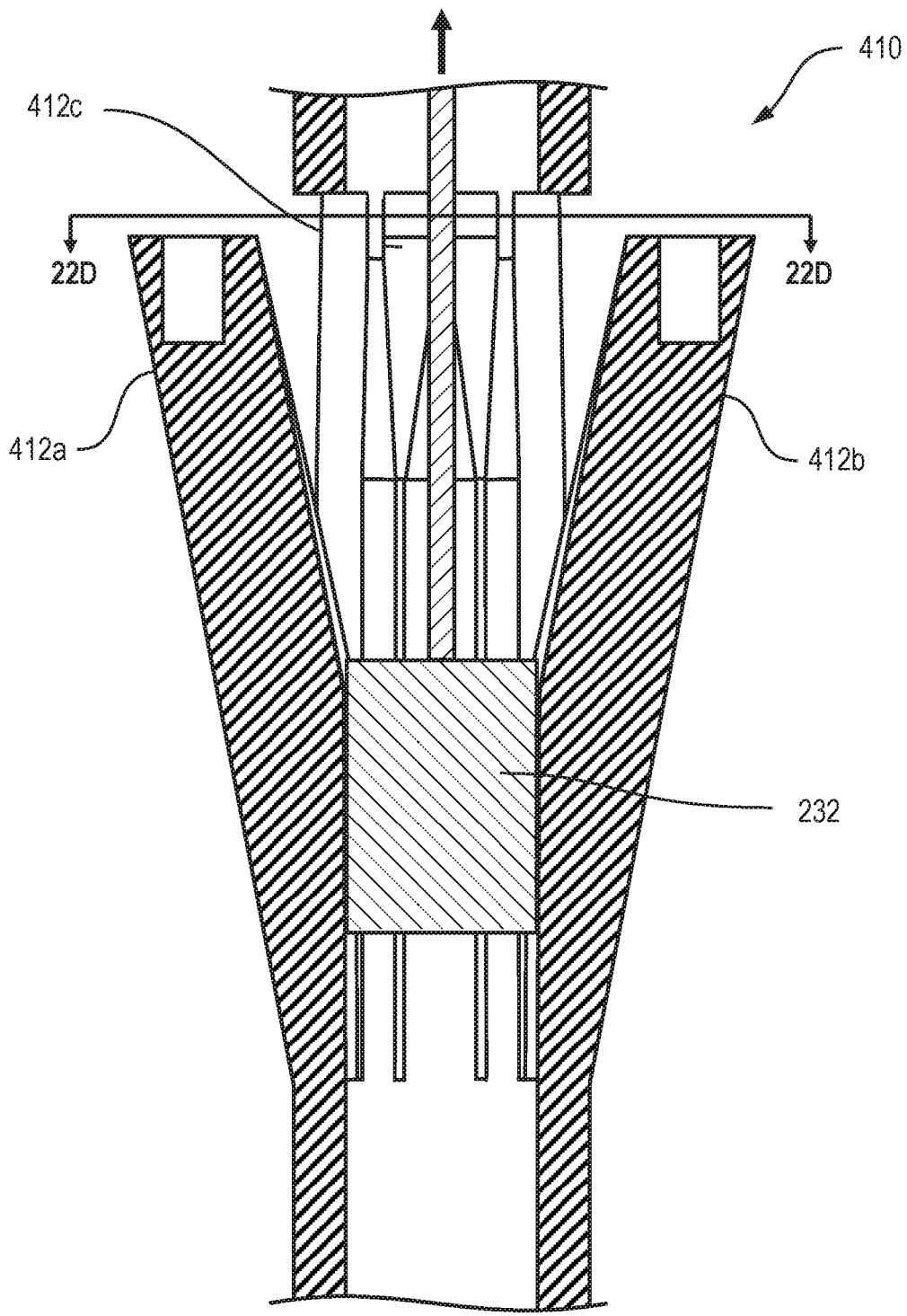
Figure 22D:
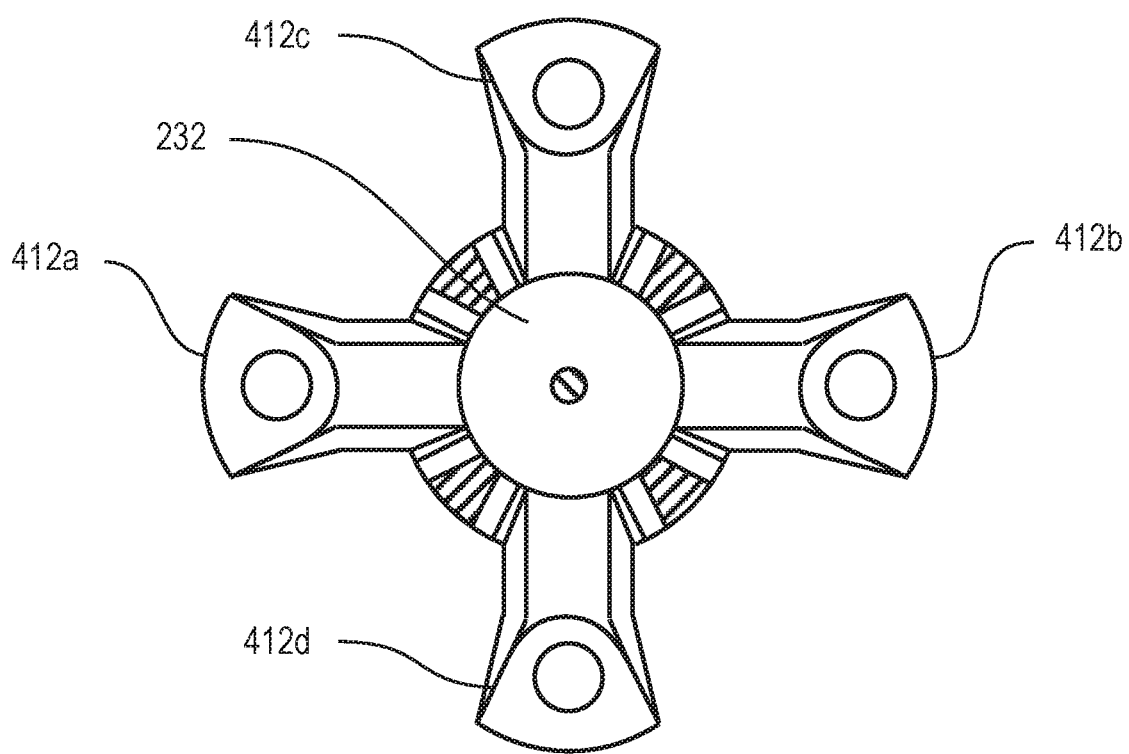

FIGS. 22A through 22D show another embodiment of a tissue locator 410 that incorporates four arms 412 (412a-412d). Tissue locator 410 is similar to tissue locator 400, except that instead of using expander 188 to deploy the arms, tissue locator 410 uses expander 232 that is moved proximally instead of distally to deploy the arms, similar to tissue locator 230 (see FIGS. 6A-6D). As such, similar to arms 234 of tissue locator 230, arms 412 are initially in a retracted position, as shown in FIGS. 22A and 22B, and can be pivoted laterally outward to the deployed position by proximal movement of expander 232, as shown in FIGS. 22C and 22D.

Tissue locators 400 and 410 can be used with any of the tissue closure devices discussed or envisioned herein and penetrators 136 can be employed therewith in any of the manners discussed above. To take advantage of all four arms 402 or 412, four penetrators 136 can be positioned within shaft 104, with each penetrator 136 being substantially aligned with one of the arms so as to be able to advance into the four cuffs. Although only two and four arms have been discussed herein, it is appreciated that more than four arms can also be used, along with the same number of corresponding cuffs, penetrators, etc.

In many respects, a tissue closure device with four arms works in a similar manner as a tissue closure device with only two arms, such as those discussed above, except for the use of the four arms instead of two. For example, regardless of the number of arms used, the tissue locator can be inserted through the tissue opening with the arms in the retracted position; the arms can be deployed and positioned against the distal wall of the tissue; the penetrators can be advanced through the tissue wall until attached to the cuffs and thereafter withdrawn; suture links and/or the cuffs can be withdrawn with the penetrators; the arms can be retracted back to the retracted position so that the tissue closure device can be withdrawn from the tissue opening, and the withdrawn suture can can be used to seal the tissue opening.

However, tissue closure devices having more than two arms can provide unique benefits over those that do not, and these benefits will be discussed below. For ease of discussion, reference numeral "500" will be used to delineate the arms when referring to the multiple arms below. In addition, each arm 500 will be referred to as "first" arm, "second" arm, "third" arm, "fourth" arm, etc., in a clockwise manner about central axis 122. Each penetrator, penetrator receptacle, cuff, etc. that corresponds with the particular arm 500 will also be referred to using the same identifier (e.g., "first", "second", "third", and "fourth"). To help in the drawings, each of the items may also include a lower-case letter, appended to the reference numeral, corresponding to the identifier, with "a" representing the "first" identifier, "b" representing the "second" identifier, and so forth. Thus, the first, second, third, and fourth arms will have designations of "500a", "500b", "500c", and "500d", as shown in FIGS. 21B and 22B.

As noted above, a penetrator 136 can be associated with each of the four arms 500. In some embodiments, penetrators 136 can be "paired" by being associated with a pair of cuffs linked together by a suture link in a similar manner to the embodiments discussed above. For example, if first and third cuffs are linked together by a suture link and second and fourth cuffs are linked together by a separate suture link, then first and third penetrators are considered to be paired with each other and second and fourth penetrators are considered to be paired with each other.

In some embodiments, each penetrator pair can be advanced and/or withdrawn independently from the other linked penetrator pairs. In other embodiments, each penetrator can be advanced and/or withdrawn independently from the other penetrators. To facilitate these options, the tissue closure device can have a plurality of penetrator actuation handles. Alternatively, the penetrator actuation handle can be divided into different portions, one for each penetrator or penetrator pair.

Figure 23A:
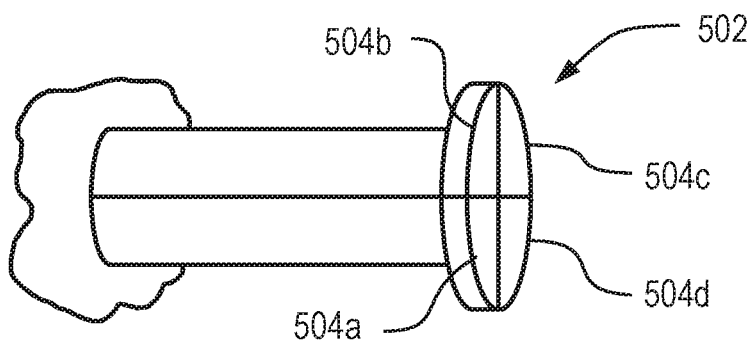
FIGS. 23A through 23D are perspective views of a penetrator actuation handle in various modes of operation.

For example, FIGS. 23A-D show an embodiment of a penetrator actuation handle 502 that can be used with either of tissue closure devices 410 or 412. As shown in FIG. 23A, penetrator actuation handle 502 can be divided into four separate penetrator actuators 504 (504a-504d). Each penetrator actuator 504 can be coupled with one of the penetrators 136 so as to direct the movements of the respective penetrator 136. For example, first, second, third, and fourth penetrator actuators 504a, 504b, 504c, and 504d can be respectively attached to first, second, third, and fourth penetrators 136a, 136b, 136c, and 136d.

Figure 23B:
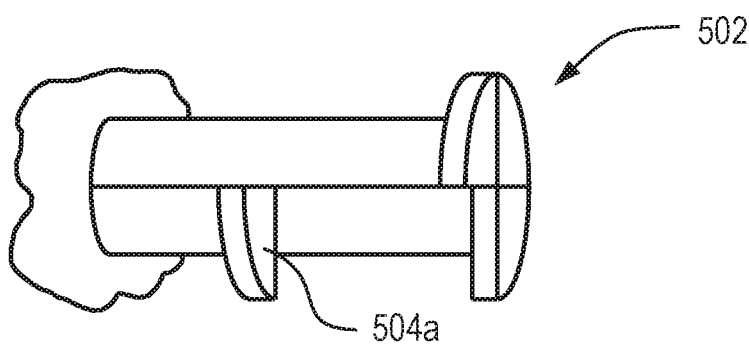
Figure 23C:
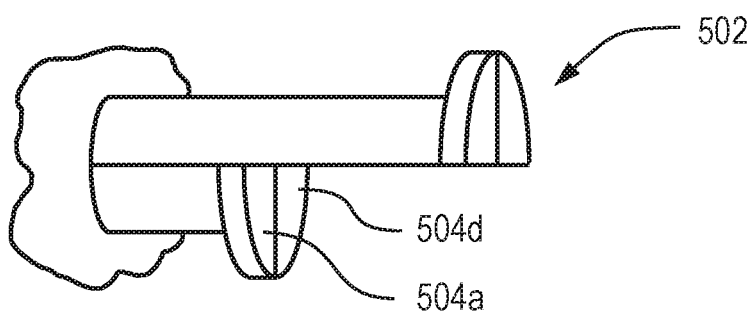
Figure 23D:
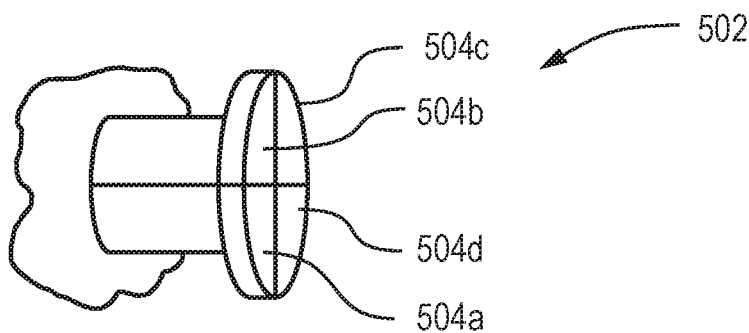

When it is desired to advance or withdraw a particular penetrator, the penetrator actuator corresponding to the desired penetrator can be advanced or withdrawn, respectively. For example, to advance first penetrator 136a distally without advancing the other penetrators, first penetrator actuator 504a can be distally advanced, as shown in FIG. 23B. If two or more penetrators are to be moved concurrently, such as, e.g., any paired penetrators, penetrator actuators 504 corresponding to the desired penetrators can be used. For example, to concurrently advance first and fourth penetrators 504a and 504d distally, first and fourth penetrator actuators 504a and 504d can be advanced, as shown in FIG. 23C. If all of the penetrators are to be moved concurrently, all of the penetrator actuators can be used. For example, to advance all of the penetrators distally at the same time, penetrator actuators 504a-504d can be advanced, as shown in FIG. 23D. Penetrator actuation handle 502 can be adapted to be used with any number of arms by simply dividing the handle 502 into the desired number of penetrator actuators 504. Other penetrator actuators can also be used.

FIGS. 24A-32C are schematic representations that illustrate examples of various link combinations and link nets that can be used to close tissue openings according to the present invention. In the examples, the ends of each link can extend into a cuff disposed within a penetrator receptacle in any of the manners discussed above. To close the tissue openings with any of the following link combinations and link nets, penetrators can be used in any of the manners discussed above to attach to the cuffs and pull the links proximally out of the body where they can be tightened, then tied off or clipped.

Although each link in FIGS. 24A-32C is shown as extending in a generally shortest route between cuffs or between cuff and hub, Applicant notes that those figures are schematic representations to illustrate a particular manner of link and that the actual links may instead be longer and may take a circuitous route between the respective cuffs, if desired, similar to the various embodiments discussed above.

Figure 24A:
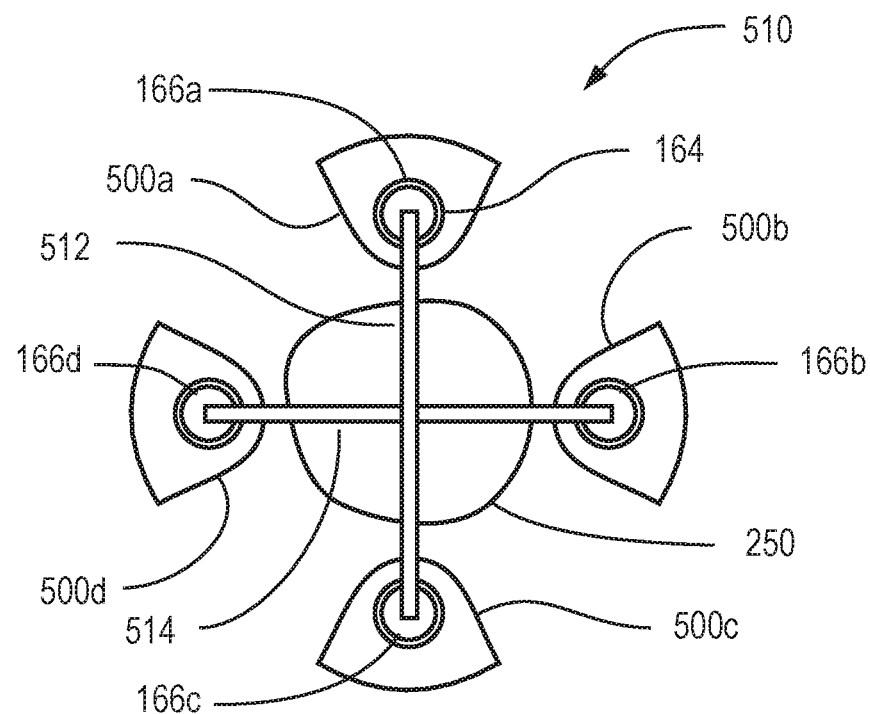
FIGS. 24A and 24B are schematic views, respectively, of a link combination and a corresponding tissue closure formed thereby, according to one embodiment.
Figure 24B:
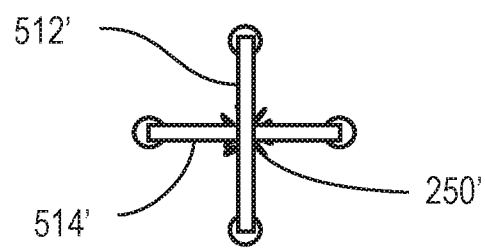

FIG. 24A illustrates one embodiment of a link combination 510 that can be used with tissue closure devices having four arms, such as tissue locators 400 and 410, discussed above. Link combination 510 includes two links 512 and 514 whose ends are attached to different cuffs. Links 512, 514 can cross each other as they span across tissue opening 250 to link diametrically opposed cuffs. For example, in the depicted embodiment the first and third cuffs 166a and 166c are linked by first link 512 and the second and fourth cuffs 166b and 166d are linked by second link 514. As such, correspondingly formed loops 512' and 514' can intersect across tissue opening 250 in a cross pattern when the opening 250' is closed thereby, as illustrated in FIG. 24B.

Although first and second links 512 and 514 intersect each other, they can be unattached to each other and therefore free to longitudinally move independent of each other.

Figure 25A:
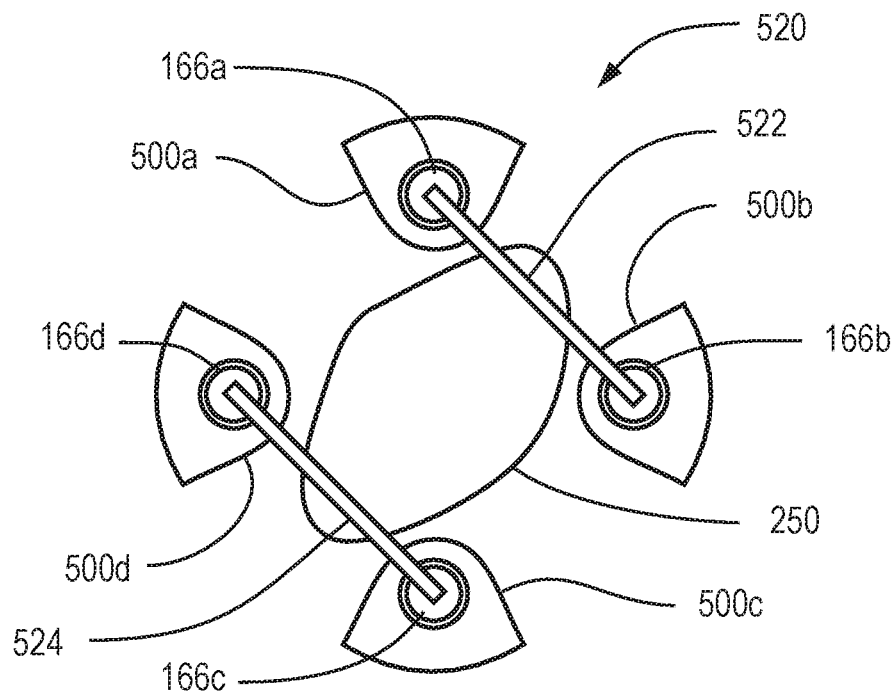
FIGS. 25A and 25B are schematic views, respectively, of a link combination and a corresponding tissue closure formed thereby, according to another embodiment.
Figure 25B:
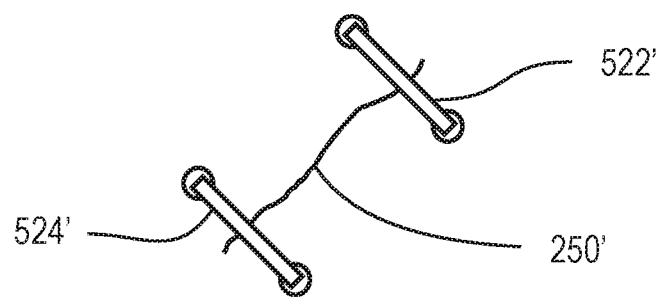

FIG. 25A illustrates another embodiment of a link combination 520 that can be used with tissue closure devices having four arms. Similar to link combination 510, link combination 520 includes two links 522 and 524 whose ends are attached to different cuffs. However, instead of being attached to diametrically opposed cuffs, the ends of each link 522, 524 attach to cuffs on adjacent arms. For example, in the depicted embodiment the first and second cuffs 166a and 166b are linked by first link 522 and the third and fourth cuffs 166c and 166d are linked by second link 524. As such, correspondingly formed loops 522' and 524' can span across tissue opening 250 without intersecting each other when the opening 250' is closed thereby, as illustrated in FIG. 25B. Link combination 520 may be especially useful for closing openings that are elongated, but may be used to close any type of tissue opening.

Figure 26A:
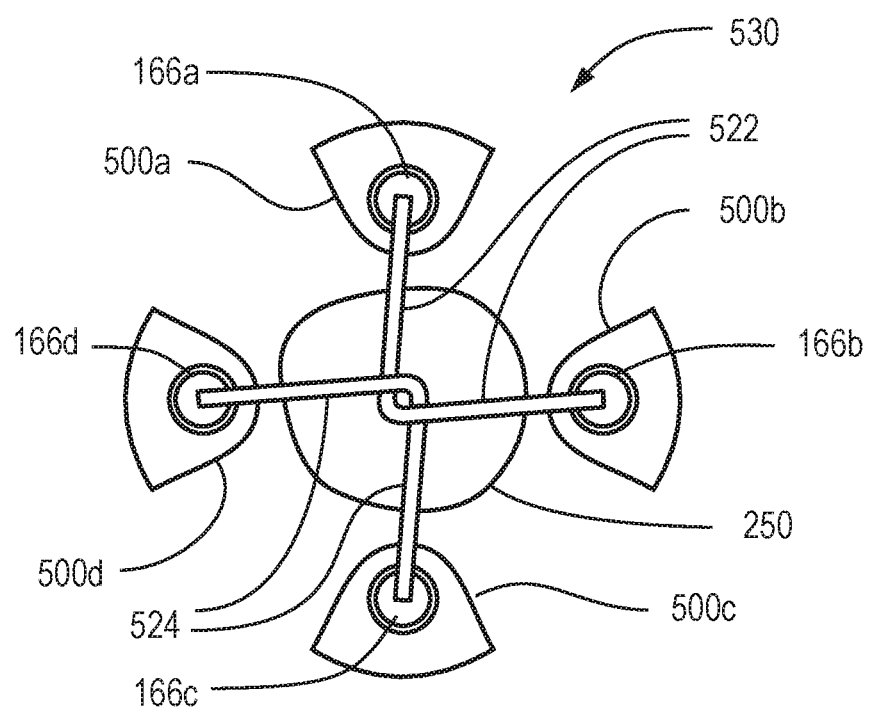
FIGS. 26A and 26B are schematic views, respectively, of a link combination and a corresponding tissue closure formed thereby, according to another embodiment.
Figure 26B:
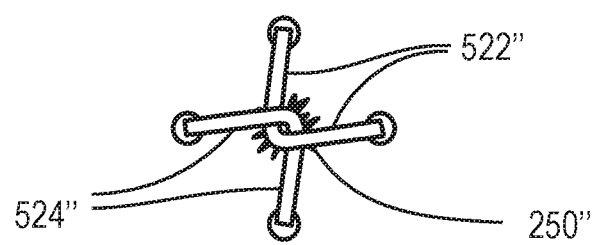

Alternatively, first and second links 522 and 524 can cross over each other as each link extends between its respective cuff, as depicted in link combination 530 in FIG. 26A. In particular, first and second links 522 and 524 can be looped through each other, as shown in FIG. 26A. As such, the correspondingly formed loops 522" and 524" can pull laterally against each other when tightened to close tissue opening 250", as illustrated in FIG. 26B. Similar to links 512 and 514, first and second links 522 and 524 can be unattached to each other and therefore free to longitudinally move independent of each other in either embodiment.

As noted above, each linked cuff pair can be attached to a different suture loop which can be closed about tissue opening 250 using one or more of the methods discussed above. For example, for link combinations 510, 520, and 530 shown respectively in FIGS. 24A, 25A, and 26A, once arms 500 have been deployed and positioned against the distal surface of the tissue, any of the methods discussed herein can be performed for any of the links.

For example, for the embodiment shown in FIG. 24A, any of the methods can be employed using linked first and third cuffs 500a and 500c and corresponding first and third penetrators to pull the corresponding link 512 proximally through the tissue and any of the methods can be employed using linked second and fourth cuffs 500b and 500d and corresponding second and fourth penetrators to pull the corresponding link 514 proximally through the tissue. In some embodiments, the same method can be used for both linked cuff pairs, and in other embodiments, different methods can be used for each linked cuff pair.

As discussed above, once links 512 and 514 have been pulled through the tissue, the corresponding suture loops can be tightened about tissue opening 250 to close the opening as shown in FIG. 24B. In a similar manner, the linked cuff pairs shown in FIGS. 25A and 26A can also be attached to suture loops to tighten about and close tissue opening 250 using any of the methods discussed herein.

The methods can be employed in parallel (i.e., the pairs of penetrators corresponding to each linked cuff pair being advanced and subsequently withdrawn concurrently) or serially (i.e., each pair of penetrators being advanced and subsequently withdrawn at different times from each other) using, e.g., penetrator actuators 504 shown in FIGS. 23A-23D.

Figure 27A:
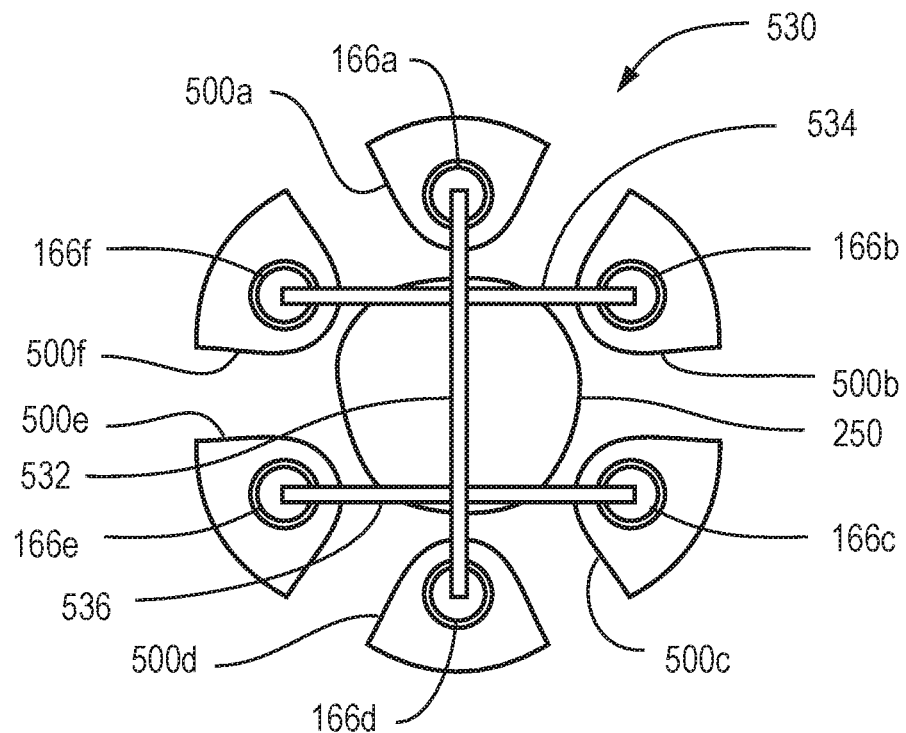
FIGS. 27A and 27B are schematic views, respectively, of a link combination and a corresponding tissue closure formed thereby, according to another embodiment.
Figure 27B:
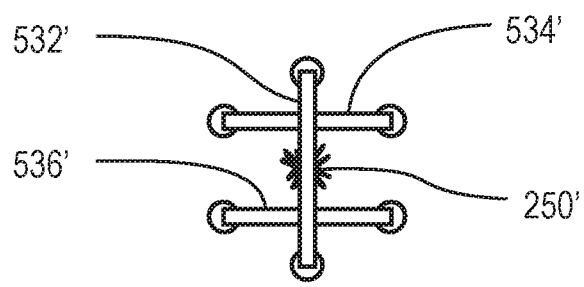

It is appreciated that the above discussion of suture links can be adapted to be used with any number of suture links. For example, FIG. 27A illustrates one embodiment of a link combination 530 that can be used with a tissue closure device having six arms. Link combination 530 includes three links 532, 534, and 536 whose ends are attached to different cuffs. First link 532 spans between diametrically opposed cuffs, while links 534 and 536 span between cuffs on either side of first link 532. Specifically, first link 532 spans between first and fourth cuffs 166a and 166d, second link 534 spans between second and sixth cuffs 166b and 166f, and third link 536 spans between third and fifth cuffs 166c and 166e, as depicted in FIG. 27A. As a result, correspondingly formed loops 532', 534', and 536' can close tissue opening 520' in the manner illustrated in FIG. 27B. Similar to other embodiments discussed herein, first, second, and third links 532, 534, and 536 can be unattached to each other and therefore free to longitudinally move independent of each other. Other link combinations are also possible. For example, along with link 532, links 534 and 536 can also span between diametrically opposed cuffs.

When using multiple suture loops or other type of filament loops to close a tissue opening, some or all of the loops can be coupled together if desired to form a filament or suture net that closes the opening in the tissue. By coupling filament or suture loops together, the resulting filament or suture net can provide a more complete closure of the tissue opening and can be used to assure the loops are positioned correctly during the closure procedure. FIGS. 28A-32B illustrate various embodiments of net links that can be used with a tissue closure device to produce a filament or suture net.

Figure 28A:
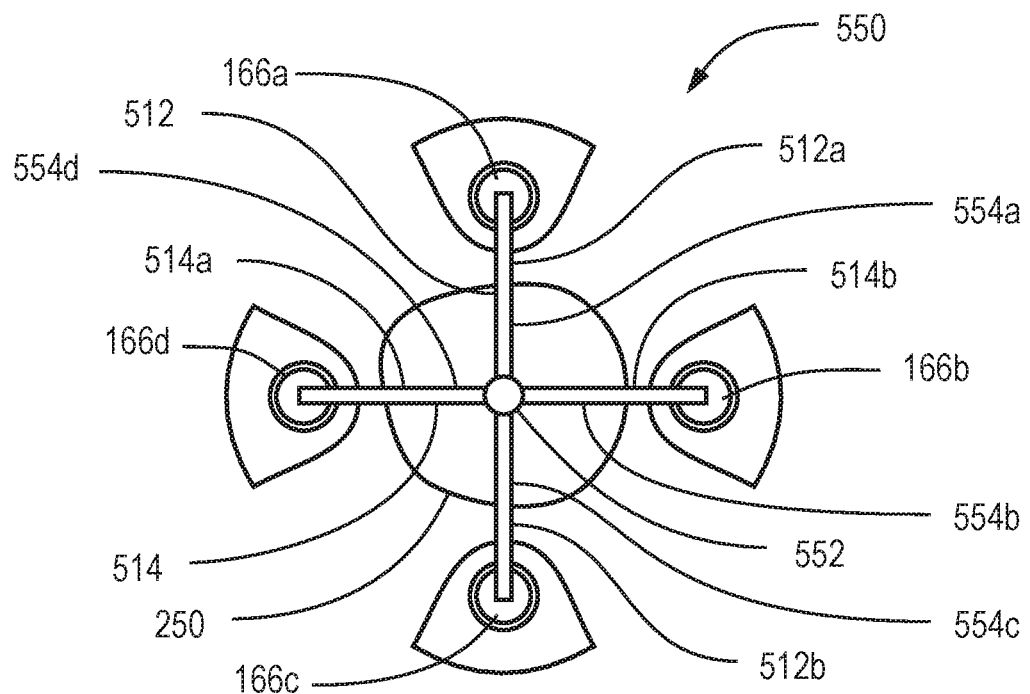
FIGS. 28A and 28B are schematic views of a suture net and corresponding tissue closure formed thereby, according to one embodiment.

In one type of suture net, the individual links can be rigidly secured to each other to form a net link. For example, FIG. 28A illustrates one embodiment of a net link 550 that can be used with tissue closure devices having four arms. Net link 550 is similar to link combination 510 shown in FIG. 24A, except that in net link 550, links 512 and 514 are rigidly secured to each other at their point of intersection to form a central hub 552. As a result, central hub 552 divides link 512 into two separate portions 512a and 512b and link 514 into two separate portions 514a and 514b. As such, net link 550 has four separate link portions 554a-554d, consisting of link portions 512a, 512b, 514a, and 514b, each extending radially outward from central hub 552 to be secured to corresponding cuffs 166a-166d. Links 512 and 514 can be secured to each other at hub 552 by adhesive, welding, fastener, or the like, or can be integrally formed together as a link assembly.

Figure 28B:
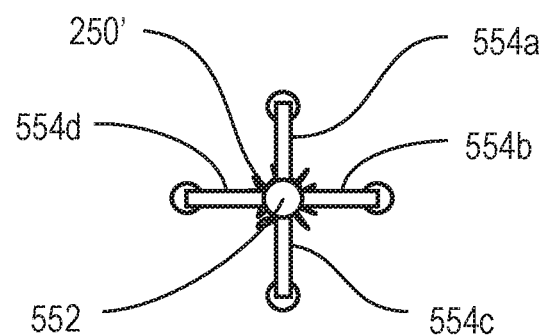

During use, each link portion 554 can remain attached to its corresponding cuff 166 when cuffs 166 are retracted proximally through the tissue by the penetrators, e.g., in a similar manner to that discussed above with respect to the method shown in FIGS. 11A-11G. As a result, all of the formed suture loop portions corresponding to link portions 554 can be pulled proximally outward through the tissue while hub 552 remains distal of the tissue wall (e.g., within a blood vessel). This produces a suture net or web. When the suture ends corresponding to the suture net are tied off to close tissue opening 250', hub 552 can remain aligned with tissue opening 250' as shown in FIG. 28B, thereby ensuring that the suture loops of the suture web properly come together on the inside of the tissue, while also providing structural strength due to the securing of the individual links at hub 552.

Figure 29A:
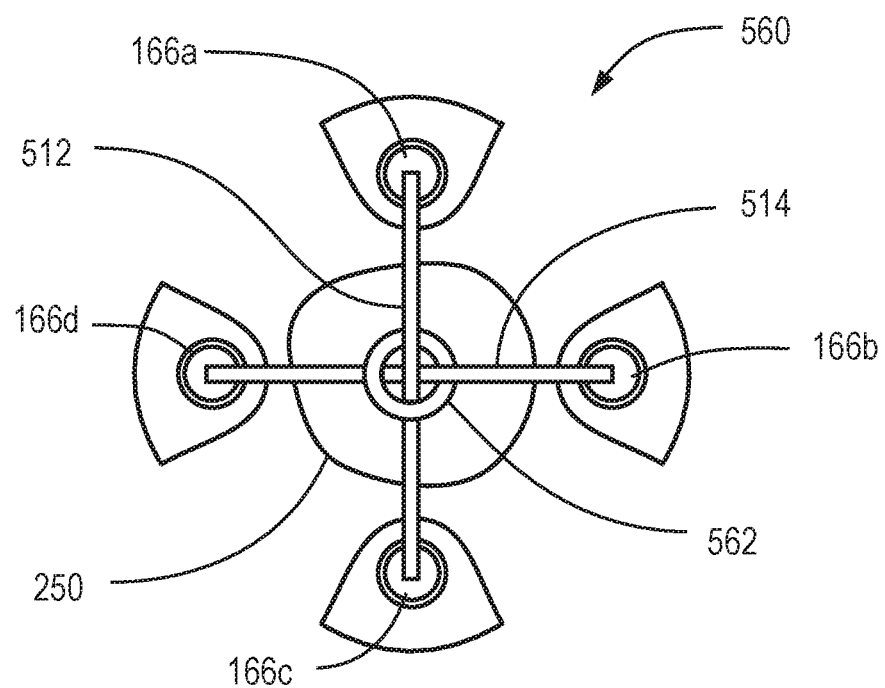
FIGS. 29A and 29B are schematic views of a suture net and corresponding tissue closure formed thereby, according to another embodiment.
Figure 29B:
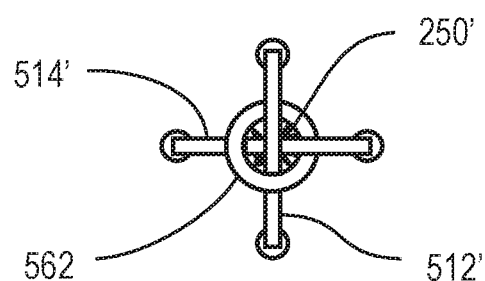

In another type of suture net, the suture loops can be loosely coupled together instead of being rigidly secured to each other. For example, FIG. 29A illustrates an alternative embodiment of a net link 560 that can be used with tissue closure devices having four arms. Net link 560 is similar to net link 550, except that individual links 512 and 514 are not rigidly secured to each other at their point of intersection. Instead, a ring 562 can be used to form the central hub where the individual links 512 and 514 intersect. Each link 512, 514 can extend through ring 562 so the correspondingly formed suture loops 512' and 514' intersect one another where they pass through ring 562, as shown in FIG. 29B. Ring 562 can allow links 512 and 514 ('and therefore, the correspondingly formed suture loops 512' and 514') to move longitudinally with respect to each other while still intersecting at hub 562. Ring 562 can be rigid or flexible. In one embodiment, ring 562 is at least large enough for cuffs 166 to pass therethrough.

In an alternative embodiment, ring 562 can be rigidly attached to one of the links 512 or 514 while the other link passes through ring 562 without being attached thereto. This can allow the link to which ring 562 is unattached to longitudinally move with respect to the link to which ring 562 is attached. Ring 562 can be comprised of a loop of suture or any other biocompatible material.

Net link 560 can be used to close a tissue opening in a similar manner as net link 550. That is, each link portion can remain attached to its corresponding cuff 166 when the cuffs are retracted proximally back through the tissue by the penetrators. Alternatively, if ring 562 is large enough for cuffs 166 to pass therethrough, the method shown in FIGS. 12A-12D can be used for either link 512 or 514. That is, one or more of the cuffs 166 can become detached from the corresponding penetrator and be pulled across the opening and proximally through the tissue by being pulled by the cuff coupled to the opposite end of the individual link. To do so, the cuff can pass through ring 562 before passing proximally through the tissue. Regardless of the manner of use, suture loops 512' and 514' of the suture net formed from net link 560 can be pulled proximally outward through the tissue and tied off while loop 562 remains over the tissue opening 250', as shown in FIG. 29B.

Figure 30A:
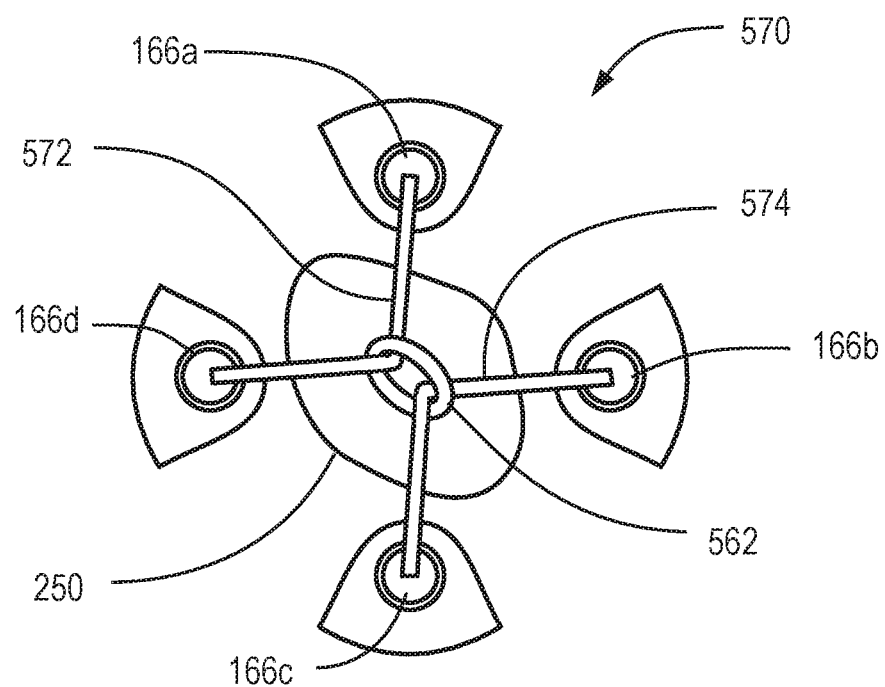
FIGS. 30A and 30B are schematic views of a suture net and corresponding tissue closure formed thereby, according to another embodiments.

FIG. 30A illustrates another embodiment of a net link 570 in which the links pass through ring 562. However, instead of extending between cuffs on diametrically opposed arms, the individual links in net link 570 extend between cuffs on adjacent arms. For example, in the depicted embodiment, first and fourth cuffs 166a and 166d are linked by first link 572 and second and third cuffs 166b and 166c are linked by second link 574. Because links 572 and 574 extend through ring 562, however, links 572 and 574 extend inward towards each other as they pass between the cuffs, as shown in FIG. 30A.

When cuffs 166 corresponding to links 572 and 574 have been pulled proximally through the tissue and corresponding suture loops 572' and 574' are tightened about tissue opening 250', the tightening force of each suture loop attempts to pull the suture loop away from the center of the opening and toward the corresponding adjacent penetrator pathway holes in the tissue.

Figure 30B:
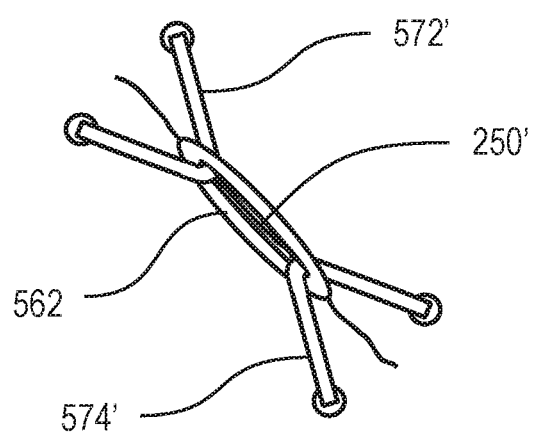

However, while allowing each suture loop 572' and 574' some movement away from the center of opening 250', ring 562 prevents suture loops 572' and 574' from moving completely away from the center of the opening, as depicted in FIG. 30B. Net link 570 may be especially useful for closing openings that are elongated, but may be used to close any type of tissue opening. If desired, ring 562 can have some elasticity to allow further movement of suture loops 572' and 574' away from each other with greater tightening force.

Figure 31A:
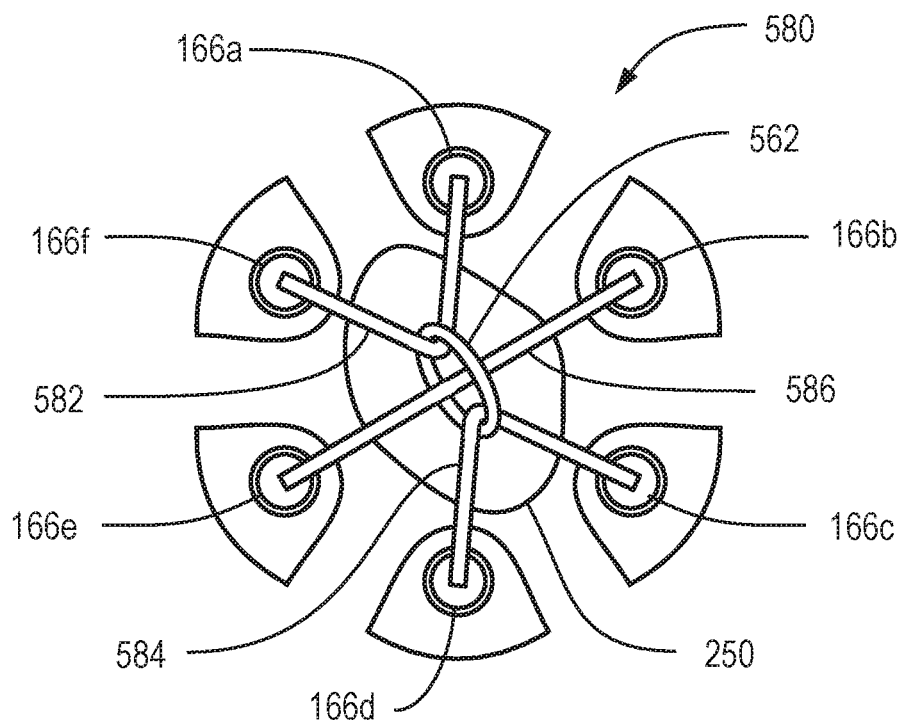
FIGS. 31A and 31B are schematic views of a suture link used in conjunction with a suture net and a corresponding tissue closure formed thereby, according to another embodiment.

FIG. 31A illustrates an embodiment of a net link 580 that can be used with a tissue closure device having six arms. Similar to net link 570, net link 580 also includes a pair of individual links that attach to cuffs on adjacent arms and pass through a ring. However, because six arms are present, net link 570 can also have another link passing between the two unused cuffs on the two additional arms.

For example, in the depicted embodiment, first and second links 582 and 584 pass through ring 562 as they respectively extend between cuff pairs 166a/166f and 166c/166d. A third link 586 is positioned between links 582 and 584 and extends across tissue opening 250 between diametrically opposed cuffs 166b and 166e. Link 586 extends through ring 562, although this is not required. That is, link 586 may or may not pass through the ring. As such, it is clear that net links can be used by themselves or in conjunction with other individual links or link combinations that are not a part of the net link.

Figure 31B:
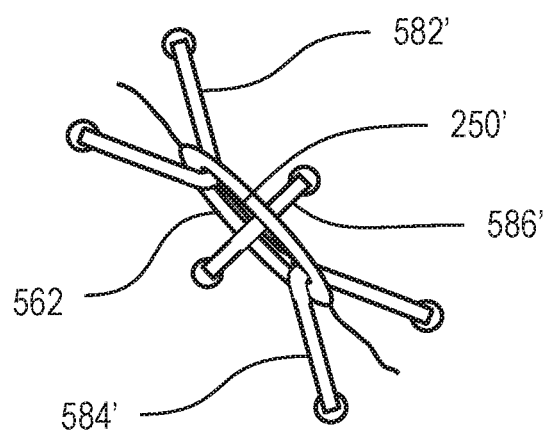

Similar to net link 570, when corresponding suture loops 582' and 584' are tightened about tissue opening 250', the tightening force of each suture loop 582' and 584' attempts to pull the suture loop away from the center of the opening and toward the corresponding adjacent penetrator pathway holes in the tissue, as shown in FIG. 31B. The additional suture loop 586' can provide additional closure across opening 250'.

In some situations, portions of the tissue surrounding opening 250 may be hardened or otherwise impenetrable due to various causes, e.g., due to scar tissue. In those cases, one or more of the penetrators may be unable to penetrate through the tissue. Suture nets can be adapted to be used in those situations.

For example, after positioning a tissue locator over the opening in the tissue and extending the arms in one of the manners discussed above, it may become apparent during the penetration phase that one or more of the penetrators cannot penetrate through the tissue. For example, if during the use of penetrator actuation handle 502 (FIG. 23A), one or more of the penetrator actuators 504 are unable to be completely advanced distally, this may signify that the penetrators corresponding to the un-advanced penetrator actuators are unable to penetrate through the tissue.

If the rest of the penetrators were allowed to continue distally through the tissue and attach to their corresponding cuffs, the un-advanced penetrators would not advance through the tissue and therefore would not attach to their corresponding cuffs. As a result, the links associated with the unattached cuffs would not become attached to the penetrators and would therefore not become attached to the suture loops coupled with the corresponding penetrators. Thus, the closure of the opening could be detrimentally affected. In one scenario, a portion of a suture loop could remain within a vessel, not tied off or attached to anything else.

To prevent this from happening, the tissue locator can be withdrawn from the body after it has been determined which penetrators cannot penetrate through the tissue and before any of the penetrators have attached to the cuffs. A suture net or web can then be formed and attached to the cuffs in the tissue locator corresponding to the penetrators that can penetrate through the tissue. The cuffs corresponding to the un-penetrating penetrators can be left unattached or can be removed from the arms. The tissue locator can then be re-inserted into the body and the suture net or web can be used to close the opening.

Figure 32A:
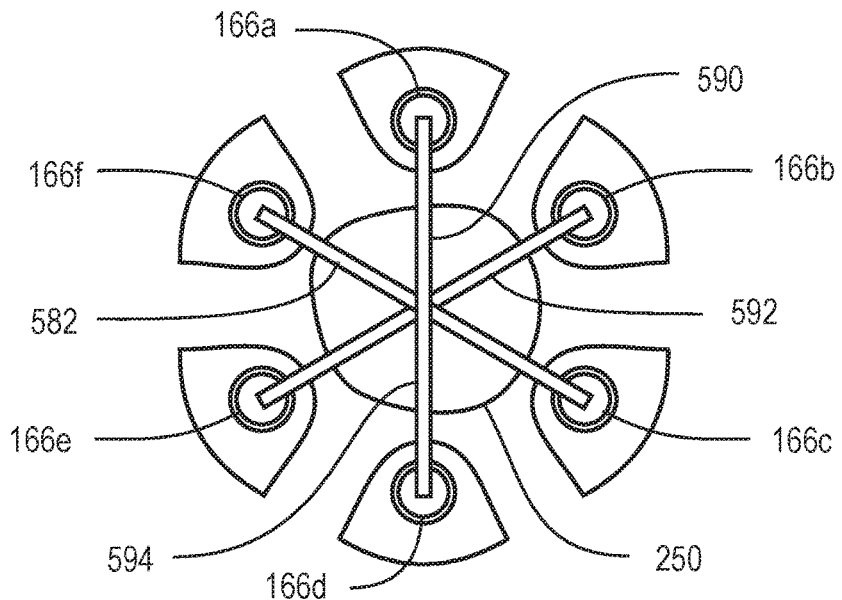
FIGS. 32A through 32C illustrate a method of using a suture net to close a tissue opening when one portion of the suture net is unusable, according to one embodiment.

For example, let us assume that a tissue locator having six arms is used to attempt to position three suture loops about tissue opening 250 using links 590, 592, and 594 configured as shown in FIG. 32A. After the tissue locator has been positioned over the opening and the arms extended, however, it becomes apparent during the penetration phase that the sixth penetrator cannot penetrate through the tissue. Before the other penetrators have been extended far enough to attach to their corresponding cuffs, the penetrators can be withdrawn back into the tissue locator, the arms rotated back to the retracted position and the tissue locator withdrawn through the opening and from the body.

Figure 32B:
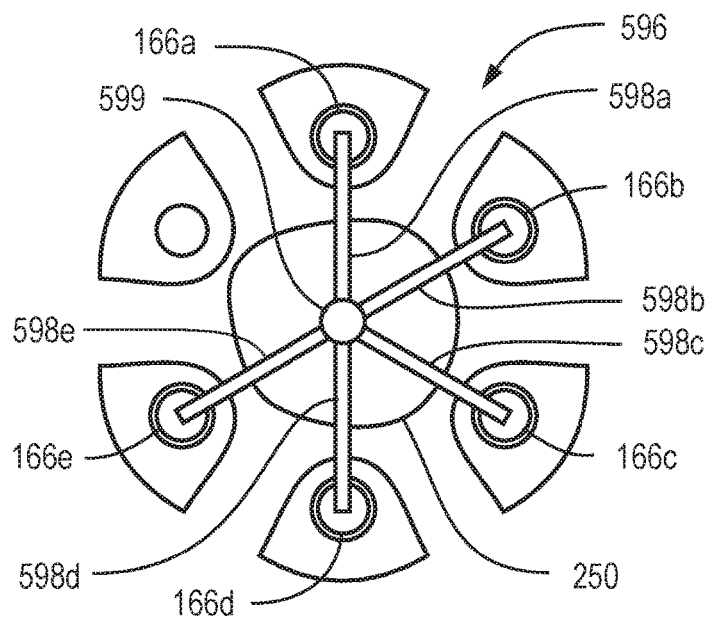

The original three links can then be replaced by a net link 596 having five link portions 598a-598e extending radially outward from a hub 599 to respectively attach to the first through fifth cuffs 166a-166e corresponding to the penetrating first through fifth penetrators; the sixth cuff 166f corresponding to the un-penetrating sixth penetrator can be left unattached or can be removed from the corresponding sixth arm, as shown in FIG. 32B. As such, in the embodiment depicted in FIG. 32B, only five of the six cuffs 166 are used to form net link 596.

Figure 32C:
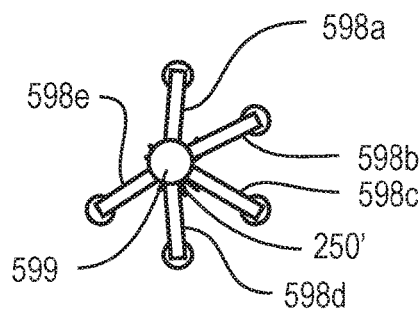

The tissue locator can then be re-inserted through the opening 250 and net link 596 can be deployed in one of the manners discussed above using only the penetrating first through fifth penetrators. The suture ends associated with net link can then be used to secure and close the opening as shown in FIG. 32C.

It is appreciated that the suture nets discussed above can be adapted for use with tissue closure devices having any number of arms. It is also appreciated that suture nets and suture loops can be mixed and matched with each other in the same tissue closure device, as desired.

Although the discussion with respect to tissue locators has been directed to the use of two, four, and six arms and associated cuffs and penetrators, it is appreciated that the discussion can be applied the use of any number of arms and associated cuffs and penetrators. For example, three, or five or more arms may be used. In some embodiments, six, eight, ten, or more arms may be used. In some embodiments an odd number of arms may be used, e.g., where one or more cuffs have a plurality of suture ends extending therefrom. As such, the present invention encompasses the use of more than two needles and associated receptacles, cuffs, sutures, and the like. Also as a result, a wide variety of stitching patterns can be provided by such multiple loop probes.

Because the arms are radially spaced about the opening, multiple suture links can be formed as well as one or more suture nets using the cuffs in the arms. In general, for any even number n of arms, a number l of links equal to half the number of arms can be formed. For example for tissue locators having six, eight, and ten arms, three, four, and five links can be formed, respectively. The links can be formed between diametrically opposed cuffs or between any of the cuffs, in the manner discussed above. Similarly, any number of arms can be used in forming a suture net.

Although various embodiments of penetrators, penetrator receptacles, cuffs, means for releasably attaching the penetrator to the cuff, bights, knots, etc. have been discussed herein, it is appreciated that other configurations of said components are also encompassed by the present invention.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method for closing an opening extending through a tissue wall, the method comprising:

inserting a distal end of a tissue locator through the opening, the tissue locator comprising a shaft formed with a first arm and a second arm, each of the first arm and the second arm comprising a first end and a second end and being resiliently bendable at the second end that is formed with the shaft, the first arm and the second arm being aligned along the shaft of the tissue locator in a retracted configuration, the tissue locator being inserted far enough through the opening that the first and second arms are positioned distal of the tissue wall, first and second ends of a filament respectively being removably coupled with the first and second arms;

advancing an elongate expander from a first position axially separated from the first arm and the second arm to a second position contacting a portion of the first arm and the second arm;

pivoting the first end of each of the first and second arms of the tissue locator about the second end of the respective arm to move the first ends of the first and second arms from the retracted configuration to a deployed configuration in which the first ends of the first and second arms extend laterally away from the shaft;

advancing a first penetrator and a second penetrator through the tissue wall, and to end faces of the first and second arms, such that the first and second penetrators respectively couple with the first and second ends of the filament, each end face comprising an opening configured to receive a tip of one of the first penetrator and the second penetrator, each end face facing generally proximally in both the deployed configuration and the retracted configuration; and withdrawing the first and second penetrators through the tissue wall, thereby causing the first and second ends of the filament to uncouple from the first and second arms, the first end of the filament remaining coupled with the first penetrator such that the first end of the filament withdraws through the tissue wall with the first penetrator.

2. The method recited in claim 1, wherein second ends of the first and second arms remain aligned along the shaft of the tissue locator in the deployed configuration.

3. The method recited in claim 1, wherein the second ends of the first and second arms are integrally formed with the shaft of the tissue locator.

4. The method recited in claim 1, wherein the second ends of the arms flex outward when the proximal ends of the arms move to the deployed configuration.

5. The method recited in claim 1, wherein the second end of the filament remains coupled with the second penetrator such that the second end of the filament withdraws proximally through the tissue wall with the second penetrator.

6. The method recited in claim 1, wherein pivoting the first ends of the arms comprises moving the elongate expander axially along the shaft so as to cause a laterally outward force to occur on the arms.

7. The method recited in claim 6, wherein moving the elongate expander axially comprises moving the elongate expander proximally to cause the laterally outward force to occur on the arms.

8. The method recited in claim 1, wherein the tissue locator further comprises a third arm and a fourth arm, first and second ends of a second filament respectively being removably coupled with the third and fourth arms, and wherein the third and fourth arms are also each aligned along the shaft of the tissue locator in the retracted configuration and the third and fourth arms are positioned distal of the tissue wall when the tissue locator is inserted through the opening, and wherein the method further comprises:

pivoting ends of each of the third and fourth arms of the tissue locator to move the ends of the third and fourth arms from the retracted configuration to a deployed configuration in which the ends of the third and fourth arms extend laterally away from the shaft;

advancing a third penetrator and a fourth penetrator through the tissue wall such that the third and fourth penetrators respectively couple with the first and second ends of the second filament; and withdrawing the third and fourth penetrators through the tissue wall, thereby causing the first and second ends of the second filament to uncouple from the third and fourth arms, the first end of the second filament remaining coupled with the third penetrator such that the first end of the second filament withdraws proximally through the tissue wall with the third penetrator.

9. The method recited in claim 8, wherein the second end of the second filament remains coupled with the fourth penetrator such that the second end of the second filament withdraws through the tissue wall with the fourth penetrator.

10. The method recited in claim 8, wherein the ends of the third and fourth arms extend in opposite lateral directions from each other and in lateral directions different than the lateral directions of the ends of the first and second arms when the third and fourth arms are in the deployed configuration.

11. The method recited in claim 8, wherein moving the elongate expander axially along the shaft also causes a laterally outward force to occur on the third and fourth arms to pivot the third and fourth arms laterally outward.

12. A method for closing an opening extending through a tissue wall, the method comprising:

inserting a distal end of a tissue locator distally through the opening, the tissue locator comprising a shaft with a plurality of arms formed with the shaft, each of the plurality of arms comprising a first end and a second end and being resiliently bendable at the second end that is formed with the shaft, the first arm and the second arm being aligned along the shaft of the tissue locator in a retracted configuration, the tissue locator being inserted far enough through the opening that the plurality of arms are positioned distal of the tissue wall, at least one filament or web being removably coupled with the plurality of arms;

advancing an elongate expander from a first position axially separated from the first arm and the second arm to a second position contacting a portion of the first arm and the second arm;

moving the plurality of arms from the retracted configuration to a deployed configuration in which the plurality of arms extend laterally away from the shaft;

for each arm, advancing a penetrator through the tissue wall toward an end face of the arm, having an opening configured to receive a tip of the penetrator, to couple with the at least one filament or web associated with the arm, the penetrators being movable independent of each other and the end face facing generally proximally in both the deployed configuration and the retracted configuration; and withdrawing the penetrators through the tissue wall, thereby causing the at least one filament or web to uncouple from the plurality of arms and withdraw through the tissue wall with the penetrators.

13. The method recited in claim 12, wherein each penetrator is advanced at different times from each other.

14. The method recited in claim 12, wherein each penetrator has a separate penetrator actuator associated therewith, and each penetrator is advanced and withdrawn by manually manipulating the associated penetrator actuator.

* * * * *